(12) United States Patent
Voytik-Harbin et al.

(10) Patent No.: US 9,315,778 B2
(45) Date of Patent: Apr. 19, 2016

(54) ENGINEERED EXTRACELLULAR MATRICES CONTROL STEM CELL BEHAVIOR

(75) Inventors: Sherry L. Voytik-Harbin, Zionsville, IN (US); Beverly Z. Waisner, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 241 days.

(21) Appl. No.: 13/236,100

(22) Filed: Sep. 19, 2011

(65) Prior Publication Data

US 2012/0094376 A1  Apr. 19, 2012

Related U.S. Application Data

(63) Continuation of application No. 11/435,635, filed on May 16, 2006.

(51) Int. Cl.
| | | |
|---|---|---|
| C12N 5/00 | (2006.01) | |
| A61K 35/12 | (2015.01) | |
| A61L 27/24 | (2006.01) | |
| C12N 5/077 | (2010.01) | |
| A61L 27/38 | (2006.01) | |
| C12N 5/0775 | (2010.01) | |

(52) U.S. Cl.
CPC ............... *C12N 5/0656* (2013.01); *A61L 27/24* (2013.01); *A61L 27/3817* (2013.01); *A61L 27/3834* (2013.01); *C12N 5/0663* (2013.01); *C12N 5/0667* (2013.01); *A61K 35/12* (2013.01); *C12N 2533/54* (2013.01); *C12N 2533/70* (2013.01); *C12N 2533/90* (2013.01)

(58) Field of Classification Search
None
See application file for complete search history.

(56) References Cited

U.S. PATENT DOCUMENTS

| | | |
|---|---|---|
| 3,949,073 A | 4/1976 | Daniels et al. |
| 4,233,360 A | 11/1980 | Luck et al. |
| 4,544,516 A | 10/1985 | Hughes et al. |
| 4,582,640 A | 4/1986 | Smestad et al. |
| 4,789,663 A | 12/1988 | Wallace et al. |
| 4,902,508 A | 2/1990 | Badylak et al. |
| 4,956,178 A | 9/1990 | Badylak et al. |
| 5,163,955 A | 11/1992 | Love et al. |
| 5,204,382 A | 4/1993 | Wallace et al. |
| 5,275,826 A | 1/1994 | Badylak et al. |
| 5,281,422 A | 1/1994 | Badylak et al. |
| 5,420,248 A | 5/1995 | Devictor et al. |
| 5,460,962 A | 10/1995 | Kemp et al. |
| 5,554,389 A | 9/1996 | Badylak et al. |
| 5,885,619 A | 3/1999 | Patel et al. |
| 5,948,429 A | 9/1999 | Bell et al. |
| 5,955,110 A | 9/1999 | Patel et al. |
| 6,099,567 A | 8/2000 | Badylak et al. |
| 6,187,047 B1 | 2/2001 | Kwan et al. |
| 6,206,931 B1 | 3/2001 | Cook et al. |
| 6,248,587 B1 | 6/2001 | Rodgers et al. |
| 6,264,992 B1 | 7/2001 | Voytik-Harbin et al. |
| 6,375,989 B1 | 4/2002 | Badylak et al. |
| 6,384,196 B1 | 5/2002 | Weis et al. |
| 6,444,229 B2 | 9/2002 | Voytik-Harbin et al. |
| 6,497,875 B1 | 12/2002 | Sorrell et al. |
| 6,576,265 B1 | 6/2003 | Spievack |
| 6,586,493 B1 | 7/2003 | Massia et al. |
| 6,592,623 B1 | 7/2003 | Bowlin et al. |
| 6,592,794 B1 | 7/2003 | Bachrach |
| 6,666,892 B2 | 12/2003 | Hiles et al. |
| 6,793,939 B2 | 9/2004 | Badylak |
| 6,893,812 B2 | 5/2005 | Woltering et al. |
| 7,029,689 B2 | 4/2006 | Berglund et al. |
| 8,241,905 B2 | 8/2012 | Forgacs et al. |
| 8,512,756 B2 | 8/2013 | Voytik-Harbin et al. |
| 2002/0076816 A1 | 6/2002 | Dai et al. |
| 2002/0170120 A1 | 11/2002 | Eckmayer et al. |
| 2002/0172705 A1 | 11/2002 | Murphy et al. |
| 2004/0037813 A1 | 2/2004 | Simpson et al. |
| 2004/0078076 A1 | 4/2004 | Badylak et al. |
| 2004/0137616 A1 | 7/2004 | Isseroff et al. |
| 2005/0014181 A1 | 1/2005 | Galis et al. |
| 2005/0019419 A1 | 1/2005 | Badylak et al. |
| 2005/0153442 A1 | 7/2005 | Katz et al. |
| 2005/0226856 A1 | 10/2005 | Ahlfors |

(Continued)

FOREIGN PATENT DOCUMENTS

| | | |
|---|---|---|
| DE | 201 15 753 U1 | 1/2002 |
| EP | 0443094 | 8/1991 |

(Continued)

OTHER PUBLICATIONS

Pizzo et al., "Extracellular matrix (ECM) microstructural composition regulates local cell-ECM biomechanics and fundamental fibroblast behavior: a multidimensional perspective," J. Appl. Physiol. 98:1909-1921 (2005; first published online Dec. 23, 2004).*
Fischbach et al., "Three-dimensional in vitro model of adipogenesis: comparison of culture conditions," Tiss. Eng'g. 10:215-229 (2004).*
Yang, et al., "The application of recombinant human collagen in tissue engineering," Biodrugs 18:103-119 (2004).*
Young et al., "Adult Stem Cells", Anat. Record Pt. A: Disc. Mol. Cell. Evol. Biol. 276A:75-102 (2004).*
Mizuno et al., "Osteogenesis by bone marrow stromal cells maintained on type I Collagen matrix gels in vivo," Bone 20:101-107 (1997).*
Young et al., "Use of mesechymal stem cells in a collagen matrix for achilles tendon repair," J. Ortopaedic Res. 16:406-413 (1998).*
McBeath et al., "Cell Shape, Cytoskeletal Tension, and RhoA Regulate Stem Cell Lineage Commitment," Developmental Cell 6:483-495 (2004).*

(Continued)

*Primary Examiner* — Julie Ha
*Assistant Examiner* — Kristina M Hellman
(74) *Attorney, Agent, or Firm* — Barnes & Thornburg LLP

(57) ABSTRACT

A composition for culturing stem cells is provided. The composition comprises an engineered purified collagen based matrix that has been formed under controlled conditions to have the desired microstructure and mechanical properties. The engineered purified collagen based matrix compositions of the present invention can be used alone or in combination with cells as a tissue graft construct to enhance the repair of damaged or diseased tissues.

25 Claims, 14 Drawing Sheets

(56) References Cited

U.S. PATENT DOCUMENTS

| | | |
|---|---|---|
| 2005/0260748 A1 | 11/2005 | Chang et al. |
| 2005/0266556 A1 | 12/2005 | Yoder et al. |
| 2006/0147501 A1 | 7/2006 | Hillas et al. |
| 2006/0165667 A1 | 7/2006 | Laughlin et al. |
| 2006/0235511 A1 | 10/2006 | Osborne |
| 2007/0026518 A1 | 2/2007 | Healy et al. |
| 2007/0077652 A1 | 4/2007 | Peled et al. |
| 2007/0190646 A1 | 8/2007 | Engler et al. |
| 2007/0269476 A1 | 11/2007 | Voytik-Harbin et al. |
| 2008/0025956 A1 | 1/2008 | Yoder et al. |
| 2008/0107750 A1 | 5/2008 | Hodde et al. |
| 2008/0181935 A1 | 7/2008 | Bhatia et al. |
| 2008/0199441 A1 | 8/2008 | Peled |
| 2008/0268052 A1 | 10/2008 | Voytik-Harbin et al. |
| 2009/0011021 A1 | 1/2009 | Voytik-Harbin et al. |
| 2009/0069893 A1 | 3/2009 | Paukshto et al. |
| 2009/0175922 A1 | 7/2009 | Voytik-Harbin et al. |
| 2009/0280180 A1 | 11/2009 | Voytik-Harbin et al. |
| 2012/0027732 A1 | 2/2012 | Voytik-Harbin et al. |
| 2012/0115222 A1 | 5/2012 | Voytik-Harbin et al. |

FOREIGN PATENT DOCUMENTS

| | | |
|---|---|---|
| EP | 1264878 | 12/2002 |
| EP | 1 270 672 A1 | 1/2003 |
| EP | 1 674 116 A2 | 6/2006 |
| GB | 2366736 | 3/2002 |
| JP | 07 074239 B | 8/1995 |
| WO | WO 94/03119 | 2/1994 |
| WO | WO 01/23529 | 4/2001 |
| WO | WO 01/45765 | 6/2001 |
| WO | WO 02/102237 | 12/2002 |
| WO | WO 03/068287 | 8/2003 |
| WO | WO 03/071991 | 9/2003 |
| WO | WO 03/087337 | 10/2003 |
| WO | WO 03/097694 | 11/2003 |
| WO | WO 2004/028404 | 4/2004 |
| WO | WO 2004/060426 | 7/2004 |
| WO | WO 2004/078120 | 9/2004 |
| WO | WO 2006/003442 | 1/2006 |
| WO | WO 2006/124946 | 11/2006 |
| WO | WO 2006/125025 | 11/2006 |
| WO | WO 2007/028079 | 3/2007 |
| WO | WO 2007/136634 | 11/2007 |
| WO | WO 2008/036393 | 3/2008 |
| WO | WO 2009/076441 | 6/2009 |
| WO | WO 2010/123928 | 10/2010 |
| WO | WO 2011/009054 | 1/2011 |

OTHER PUBLICATIONS

Kong et al. "FRET measurements of cell-traction forces and nanoscale clustering of adhesion ligands varied by substrate stiffness," PNAS 102:4300-4305 (2005).*

Settleman, "Tension Precedes Commitment—Even for a Stem Cell," Molecular Cell 14:148-150 (2004).*

Engler et al., "Substrate Elasticity Directs Adult Mesenchymal Stem Cell Differentiation," Abstract 783, The 37th Middle Atlantic Regional Meeting (May 22-25, 2005) New Brunswick, NJ—accessed Jan. 22, 2015 at URL acs.confex.com/acs/marm05/techprogram/P17320.htm.*

"Basement Membrane" accessed online at http://en.wikipedia.org/wiki/Basement_membrane#Composition on Jun. 11, 2010.

"Extracellular Matrix" accessed at http://en.wikipedia.org/wiki/Extracellular_matrix on Jun. 11, 2010.

Bell, Brett J. et al., "Cell Density and Extracellular Matrix (ECM) Microstructure Control Mechanical Behavior of Engineered Tissue Constructs", *2005 Summer Bioengineering conference*, (Jun. 22-26, 2005).

Bjornsson, S., "Simultaneous Preparation and Quantitation of Proteoglycans by Precipitation with Alcian Blue", Analytical Biochemistry, vol. 210, 1993, pp. 282-291.

Brightman et al., "Time-Lapse Confocal Reflection Microscopy of Collagen Fibrillogenesis and Extracellular Matrix Assembly In Vitro", *Biopolymers*, vol. 54, 222-234, (2000).

Callister, W. D, Jr., Materials Science and Engineering: an Introduction, 3$^{rd}$ edition, New York, NY, John Wiley & Sons, Inc., 1994.

Chandrakasan et al. J. Biol. Chem., 1976, 251:6062-67.

Ciovacco et al., Bone, 2009, 44(1):80-86.

Comper, W. D., and A. Veis, "Characterization of Nuclei in in Vitro Collagen Fibril Formation", Biopolymers, vol. 16, 1977, pp. 2133-2142.

Compston, "Bone marrow and bone: a functional unit," Journal of Endocrinology, 173: 387-394, 2002.

Davis, et al., "Injectable Self-Assembling Peptide Nanofibers Create Intramyocardial Microenvironments for Endothelial Cells", *Circulation*, 111, 442-50, (Feb. 1, 2005).

Fulzele, S. V., P. M. Satturwar, A. K. Doyle, "Study of the Biodegradation and in Vivo Biocompatibility of Novel Biomaterials", European Journal of Pharmaceutical Sciences, vol. 20, 2003, pp. 53-61.

Gallop, P. M., and S. Seifter, "Preparation and Properties of Soluble Collagens", Soluble Collagens, 1963, pp. 635-641.

Gelman et al., "Collagen Fibril Formation in Vitro," J. Biol. Chem., 1979, 254(22): 11741-11745.

Gelman et al., "Collagen Fibril Formation," J. Biol. Chem., 1979, 254(1):180-186.

Griffey, S., N. D. Schwade, C. G. Wright, "Particulate Dermal Matrix as an Injectable Soft Tissue Replacement Material", J. Biomed. Mater. Res. vol. 58, 2001, pp. 10-15.

Hou, et al., "Radiolabeled Cell Distribution After Intramyocardial, Intracoronary, and Interstitial Retrograde Coronary Venous Delivery", *Circulation*, 112, 150-6, (Aug. 30, 2005).

Hunt, T. K., P. Twomey, B. Zederfeldt, and J. E. Dunphy, "Respiratory Gas Tensions and PH in Healing Wounds", American Journal of Surgery, vol. 114, 1967, pp. 302-307.

Ingram, D. A., et al., "Identification of a Novel Hierarchy of Endothelial Progenitor Cells Using Human Peripheral and Umbilical Cord Blood", Blood, 104, 2752-2760, (2004).

International Search Report and Written Opinion Nov 29, 2007 for PCT/US2006/019130.

Kacena et al., J. of Histotechnology, 2004, 27:119-130.

Knott et al., "Collagen Cross-Links in Mineralizing Tissues: A Review of Their Chemistry, Function, and Clinical Relevance," 1998, 22(3):181-187.

Kondo et al., "Biology of Hematopoietic Stem Cells and Progenitors: Implications for Clinical Application," Annu. Rev. Immunol., 2003, 21:759-806.

Korff et al., Jour. of Cell Science, vol. 112: 3249-3258 (1999).

Kreger et al., "Hyaluronan concentration within a 3D collagen matrix modulates matrix viscoelasticity, but not fibroblast response," Matrix Biol., 2009, 28(6):336-46.

Kreger, "Design of 3D Collagen Matrices for Cell Delivery and Guidance in Tissue Engineering," Thesis Submitted to the Faculty of Purdue University in Partial Fulfillment of the Requirements for the Degree of Doctor of Philosophy, May 2009, Purdue University.

Lin et al., "Comparison of Physical-Chemistry Properties of Type I Collagen from Different Species," *Food Chemistry*, 99(2): 244-251 (2005).

Malvern, *Introduction to the Mechanics of a Continuous Medium.* Upper Saddle River, NJ: Prentice-Hall, 1969.

Marotta, M., G. Martino, "Sensitive Spectrophotometric Method for the Quantitative Estimation of Collagen", Analytical Biochemistry, vol. 150, 1985, pp. 86-90.

Miller et al., "Preparation and Characterization of the Different Types of Collagen," *Methods in Enzymology*, 82: 33-64 (1982).

Miller, E. J., E. H. Epstein, Jr., and K. A. Piez, "Identification of Three Genetically Distinct Collagens by Cyanogen Bromide Cleavage of Insoluble Human Skin and Cartilage Collagen", Biochemical and Biophysical Research Communications, vol. 42, No. 6, 1971, pp. 1024-1029.

Na, "Monomer and Oligomer of Type I Collagen: Molecular Properties and Fibril Assembly," 1989, 28(18):7161-67.

Narmoneva et al., "Endothelial Cells Promote Cardiac Myocyte Survival and Spatial Reorganization", *Circulation*, 110, 962-968, (Aug. 24, 2004).

(56) References Cited

OTHER PUBLICATIONS

Nguyen et al., "Comparison of the Amino Acid Composition of Two Commercial Porcine Skins (Rind)," *Journal of Agricultural and Food Chemistry*, 34(3): 565-572 (1986).

Nielsen, T. B. and J. A. Reynolds, "Measurements of Molecular Weights by Gel Electrophoresis", Methods in Enzymology, vol. 48, Hirs and Temasheff, Eds., Academic Press, New York, 1978, pp. 3-10.

Orschell-Traycoff et al., Blood, 2000, 96:1380-1387.

Osborne, et al., "Investigation into the tensile properties of collagen/chondroitin-6-sulphate gels: the effect of crosslinking agents and diamines", *Medical & Biological Engineering & Computing*, vol. 36, 129-134, (1998).

Ozerdem, et al., "Physical Response of Collagen Gels to Tensile Strain", *Journal of Biomechanical Engineering*, vol. 117, 397-401, (Nov. 1995).

Pizzo et al., "Cell-Extracellular Matrix (ECM) Micro-Mechanical Behavior Depends on ECM Microstructure and Cell Type", *2005 Summer Bioengineering Conference*, (Jun. 22-26, 2005).

Pizzo et al., "Extracellular matrix (ECM) microstructural composition regulates local cell-ECM biomechanics and fundamental fibroblast behaviour: a multidimensional perspective", *J Appl Physiol*, 98: 1909-1921, (2005).

Pizzo et al., "Long-term Production of Choline Acetylatransferase in the CNS After Transplantation of Fibroblasts Modified with a Regulatable Vector", *Mol Brain Res*, 126, 1-13 (2004).

Rehman, et al., "Secretion of Angiogenic and Antiapoptotic Factors by Human Adipose Stromal Cells", *Circulation*, 109: 1292-8, (Mar. 16, 2004).

Reinlib, et al., "Cell Transplantation as Future Therapy for Cardiovascular Disease?", *Circulation*, 101: e182-e187, (2000).

Roeder B. A., K. Kokini, J. E. Sturgis, J. P. Robinson, S. L. Voytik-Harbin, "Tensile Mechanical Properties of Three-Dimensional Type 1 Collagen Extracellular Matrices with Varied Microstructure", J. Biomech. Eng., vol. 124, 2002, pp. 214-222.

Roeder et al., "Local, Three-Dimensional Strain Measurements Within Largely Deformed Extracellular Matrix Constructs", *J Biomech Eng*, 126, 699-708, (2004).

Scadden, "The stem cell niche as an entity of action," Nature, 441: 1075-1079, 2006.

Schechner et al., "In vivo formation of complex microvessels lined by human endothelial cells in an immunodeficient mouse," *PNAS*, Aug. 1, 2000, vol. 97, No. 16, 9191-9196.

Schilling, J. A., W. Joel, H. M. Shurley, "Wound Healing: A Comparative Study of the Histochemical Changes in Granulation Tissue Contained in Stainless Steel Wire Mesh and Polyvinyl Sponge Cylinders", Surgery, vol. 46, No. 4, Oct. 1959, pp. 702-710.

Shiozawa et al., "The bone marrow niche: habitat to hematopoietic and mesenchymal stem cells, and unwitting host to molecular parasites," Leukemia, 22(5): 941-950, 2008.

Sieminski et al., Expt. Cell Res., vol. 297, pp. 574-584 (2004).

Spradling et al., "Stem Cells Find Their Niche," Nature, 414: 98-104, 2001.

Strang, et al., *Linear Algebra and Its Applications*. 3rd edition. San Diego, CA: Academic Press, 1988.

Sykes, B., B. Puddle, M. Francis, and R. Smith, "The Estimation of Two Collagens from Human Dermis by Interrupted Gel Electrophoresis", Biochemical and Biophysical Research Communications, vol. 72, No. 4, 1976, pp. 1472-1480.

Veis, Arthur, et al., "Fundamentals of Interstitial; Collagen Self-Assembly", 1994, Extracellular Matrix Assembly and Structure, Academic Press, pp. 15-45.

Voytik-Harbin et al., "Application and Evaluation of the Alamarblue Assay for Cell Growth and Survival of Fibroblasts", *In Vitro Cell Dev Biol Anim*, 34, 239-246, (1998).

Voytik-Harbin et al., "Simultaneous Mechanical Loading and Confocal Reflection Microscopy for Three-Dimensional Microbiomechanical Analysis of Biomaterials and Tissue Constructs", *Microsc Microanal*, 9, 74-85, (2003).

Voytik-Harbin et al., Small Intestinal Submucosa: A Tissue-Derived Extracellular Matrix That Promotes Tissue-Specific Growth and Differentiation of Cells in Vitro, *Tissue Engineering*, 4, 2, 157-174, (1998).

Voytik-Harbin et al., "Three-Dimensional Imaging of Extracellular Matrix and Extracellular Matrix-Cell Interactions", *Methods in Cell Biology*, 63, 583-597, (2001).

Wess, Collagen fibrillar structure and hierarchies in P. Fratzl (ed.), Collagen: Structure and Mechanics, Springer Science+Business Media, LLC, New York, 2008, 53-60.

Yoder et al., "Redefining endothelial progenitor cells via clonal analysis and hematopoietic stem/progenitor cell principals," Blood, 2007, 109:1801-1809.

Bailey JL et al., "Collagen Oligomers Modulate Physical and Biological Properties of Three-Dimensional Self-Assembled Matrices," Biopolymers, 2010; 95(2): 77-93.

Na et al., "In Vitro Collagen Fibril Assembly in Glycerol Solution: Evidence for a Helical Cooperative Mechanism Involving Microfibrils," Biochemistry, 1986; 25: 958-966.

Na et al., "Mechanism of in Vitro Collagen Fibril Assembly," Journal of Biological Chemistry, 1986; 261(26): 12290-12299.

Voytik-Harbin et al., "Identification of Extractable Growth Factors from Small Intestine Submucosa," J Cell. Biochemistry, 1997; 67: 478-491.

Condell RA et al., "Analysis of Native Collagen Monomers and Oligomers by Size-Exclusion High-Performance Liquid Chromatography and its Application," *Analytical Biochemistry*, 1993; 212: 436-445.

"Density" form Merriam-Webster online, accessed on Feb. 1, 2011.

Kim, J. Food Science, 2004, 69: 637-642.

Munakata, et al., Glycobiology, vol. 9, 1023-1027 (1999).

Billiar, Cellular and Biomolecular Mechanics and Mechanobiology, Amit Gefen, Ed., p. 210 (2011).

Ho et al., "Characterization of Collagen Isolation and Application of Collagen Gel as a Drug Carrier", J. of Controlled Release, vol. 44, pp. 103-112 (1997).

Liu, Asian-Aust J. Anim. Sci, 2001; 14(11):1638-1644.

Lynn et al., "Antigenicity and immunogenicity of collagen," J Biomed Mater Res, Part B: Appl Biomater, 2004; 71B: 343-354.

Taichman et al., "Human Osteoblasts Support Hematopoiesis through the Production of Granulocyte Colony-stimulating Factor," Journal of Experimental Medicine, 1994; 179:1677-1682.

TeBmar et al., "Hydrogels for tissue engineering," *Fundamentals of Tissue Engineering and Regenerative Medicine*, 2009; p. 495-517.

Koken, "About Collagen," Technical information, Support webpage, 2006.

Taqvi et al., "Influence of scaffold physical properties and stromal cell coculture on hematopoietic differentiation of mouse embryonic stem cells," *Biomaterials*, 2006; 24:6024-6031.

Engler et al., "Matrix elasticity directs stem cell lineage specification," *Cell*, 2006; 126:677-689.

Reinisch et al, "Humanized large-scale expanded endothelial colony-forming cells function in vitro and in vivo," *Blood*, 2009; 113:6716-6725.

Silver et al., "Collagen self-assembly and the development of tendon mechanical properties," *Journal of Biomechanics*, 2003; 36:1529-1553.

Product information: Collagen Solution—Type I from rat tail, Sigma, http://www.sigmaaldrich.com/etc/medialib/docs/Sigma/Datasheet/3/c3867dat.Par.0001.File.tmp/c3867dat.pdf.

Gallagher D, "Stem cells being made from blood," available at www.bbc.co.uk/news/health-20539835.

Ingram D et al., "Vessel wall-derived endothelial cells rapidly proliferate because they contain a complete hierarchy of endothelial progenitor cells," *Blood*, 2005; 105(7):2783-6 (Epub Dec. 7, 2004).

Ingram D et al., "Unresolved questions, changing definitions, and novel paradigms for defining endothelial progenitor cells via clonal analysis and hematopoietic stem/progenitor cell principals," *Blood*, 2007; 109(5):1801-9 (Epub Oct 19.

Prater DN et al., "Working hypothesis to redefine endothelial progenitor cells," *Leukemia*, 2007; 21(6):1141-9 (Epub Mar. 29, 2007).

(56) References Cited

OTHER PUBLICATIONS

Case J et al., "Human CD34+AC133+VEGFR-2+ cells are not endothelial progenitor cells but distinct, primitive hematopoietic progenitors," *Exp Hematol.*, 2007; 35(7):1109-18.
Hirschi KK et al, "Assessing identify, phenotype, and fate of endothelial progenitor cells," *Arterioscler Thromb Vasc Biol*, 2008; 28(9):1584-95 (Epub Jul. 31, 2008).
Timmermans F et al., "Endothelial progenitor cells: identify defined?", *J Cell Mol Med*, 2009; 13(1):87-102.
Mund JA et al, "Endothelial progenitor cells and cardiovascular cell-based therapies," *Cytotherapy*, 2009; 11(2):103-13.
Chor Wing Tam et al. EWMA Journal, 2012; 12(2).
Boyd et al. Atlas and Text of Corneal Pathology and Surgery; 2011.
Vasiliev and Gelfand (Neoplastic and Normal Cells in Culture, Cambridge University Press (1981), p. 19.
"Stem Cells and the Future of Regenerative Medicine" m published by the National Academy of Sciences (2002), p. 19.
Stem Cell Differentiation (science and global issues/biology, cell biology), 2013.
Shimizu, "Fabrication of pulsatile cardiac tissue grafts using a novel 3-dimensional cell sheet manipulation technique and temperature-responsive cell culture surfaces," *Circ Res.*, 2002, 90:e40-48.
Engler et al., "Myotubes differentiate optimally on substrates with tissue-like stiffness: pathological implications for soft or stiff microenvironments," *Journal of Cell Biology*, 2004; 165:877-887.

\* cited by examiner

_US 9,315,778 B2_

ENGINEERED EXTRACELLULAR MATRICES CONTROL STEM CELL BEHAVIOR

CROSS REFERENCE TO RELATED APPLICATIONS

This application is a continuation of U.S. application Ser. No. 11/435,635, filed May 16, 2006, which is incorporated herein by reference.

GOVERNMENT RIGHTS

This invention was made with government support under Grant No. EB000165awarded by National Institutes of Health. The government has certain rights in the invention.

FIELD OF THE INVENTION

This invention relates to the preparation of a collagen based matrix for culturing and differentiating stem cells and progenitor cells and the use of such compositions as tissue graft constructs.

BACKGROUND

The interaction of cells with their extracellular matrix (ECM) as it occurs in vivo plays a crucial role in the organization, homeostasis, and function of tissues and organs. Continuous communication between cells and their surrounding ECM environment orchestrates critical processes such as the acquisition and maintenance of differentiated phenotypes during embryogenesis, the development of form (morphogenesis), angiogenesis, wound healing, and even tumor metastasis. Both biochemical and biophysical signals from the ECM modulate fundamental cellular activities including adhesion, migration, proliferation, differential gene expression, and programmed cell death.

In turn, the cell can modify its ECM environment by modulating the synthesis and degradation of specific matrix components. The realization of the significance of cell-ECM interaction has led to a renewed interest in characterizing ECM constituents and the basic mechanisms of cell-ECM interaction.

Tissue culture allows the study in vitro of animal cell behavior in an investigator-controlled physiochemical environment. Presumably cultured cells function best (i.e., proliferate and perform their natural in vivo functions) when cultured on substrates that closely mimic their natural environment. Currently, studies in vitro of cellular function are limited by the availability of cell growth substrates that present the appropriate physiological environment for proliferation and development of the cultured cells. Complex scaffolds representing combinations of ECM components in a natural or processed form are commercially available, such as Human Extracellular Matrix (Becton Dickinson) and MATRIGEL®. However, none of the existing scaffolds have been prepared under conditions that regulate the polymerization of the scaffold in a controlled manner so as to produce a composition having mechanical properties and a predetermined 3D microstructure of collagen fibrils and/or soluble ECM components that optimizes cell-substrate interactions to yield predictable and reproducible cellular outcomes. Applicants have discovered that the physical state of an ECM scaffold and not just its molecular composition should be considered in the design of new and improved scaffolds.

As reported herein, modifying the conditions used to form a collagen based matrix from a solubilized collagen solution allows for the controlled alteration of the micro-structural and subsequent mechanical properties of the resulting ECM scaffold. Furthermore, the micro-structural and mechanical properties of the ECM scaffold directly impact fundamental cell behavior including survival, adhesion, proliferation, migration and differentiation of cells cultured within the scaffold.

Basement membrane tissues and submucosal material harvested from warm blooded vertebrates have shown great promise as unique graft materials for inducing the repair of damaged or diseased tissues in vivo, and for supporting fundamental cell behavior (e.g., cell proliferation, growth, maturation, differentiation, migration, adhesion, gene expression, apoptosis and other cell behaviors) of cell populations in vitro. Submucosal material can be extracted or fluidized to provide enriched extracts that can be utilized as additives for tissue culture media, or polymerized to form collagen based scaffolds, to promote in vitro cell growth and proliferation.

As a tissue graft, submucosal tissue undergoes remodeling and induces the growth of endogenous tissues upon implantation into a host. Numerous studies have shown that submucosal tissue is capable of inducing host tissue proliferation, remodeling and regeneration of tissue structures following implantation in a number of in vivo environments, including the urinary tract, the body wall, tendons, ligaments, bone, cardiovascular tissues and other vascular tissues, and the central nervous system. Upon implantation of the submucosal tissues, cellular infiltration and a rapid neovascularization are observed and the submucosa materials are remodeled into host replacement tissue with site-specific structural and functional properties.

Accordingly, submucosa tissue can be used as a tissue graft construct, for example, in its native form, in its fluidized form, in the form of an extract, or as components extracted from submucosa tissue and subsequently purified. The fluidized forms of vertebrate submucosa tissue can be gelled to form a semi-solid composition that can be implanted as a tissue graft construct or utilized as a cell culture substrate. As a tissue graft material, the fluidized form can be injected, or delivered using other methods, to living tissues to enhance tissue remodeling. Furthermore, the fluidized form can be modified, or can be combined with specific proteins, growth factors, drugs, plasmids, vectors, or other therapeutic agents for controlling the enhancement of tissue remodeling at the site of injection. Moreover, the fluidized, solubilized form can be combined with primary cells or cell lines prior to injection to further enhance the remodeling properties that result in the repair or replacement of diseased or damaged tissues.

Because the molecular forces that orchestrate the self assembly of soluble, monomeric collagen into higher ordered structures are weak their assembly can easily turn into an unstructured aggregation of misfolded proteins. In the literature, there are known methods for isolating collagen from a variety of tissues, e.g., placenta and animal tails and using the isolated material to reconstitute collagenous matrices. These known methods rely on the protein's intrinsic ability to retain its secondary structure during protein isolation and assume that, for instance, the alpha helix will retain its helical structure throughout. The end result, even with a homogenous biochemical composition, can be a heterogeneous secondary structure. Controlling the assembly of the constituting monomers into tertiary or quaternary multimeric arrangements is very hard to achieve under such conditions. One embodiment of the present invention is directed to controlling the polymerization of a composition comprising solubilized collagen to form a collagen based scaffold that has the requisite microstructure and composition to allow for the expansion, differentiation and/or clonal isolation of stem cells in a highly reproducible and predictable manner.

SUMMARY

The present invention relates to compositions comprising a three dimensional matrix that is formed to have the requisite composition and microstructure to enhance the proliferation and/or differentiation of stem cells or progenitor cells cultured within such a matrix. In accordance with one embodiment an improved method for culturing stem cells is provided. The method comprises preparing a solubilized collagen composition from a source of collagen, adding cells to the solubilized collagen composition and polymerizing the collagen composition under controlled conditions to provide a matrix formed from collagen fibrils and having the desired microstructure. In one embodiment cells are added to the collagen based matrix at a cell density within two orders of magnitude of the minimum cell number required to maintain cell viability, and the cells are cultured under conditions suitable for proliferation of the cells. In one embodiment the three dimensional matrix has a fibril area fraction (defined as the percent area of the total area occupied by fibrils in a cross-sectional surface of the matrix; providing an estimate of fibril density) of about 8% to about 26% and an elastic or linear modulus (defined by the slope of the linear region of the stress-strain curve) of about 0.5 to about 40 kPa. In one embodiment the three dimensional matrix is further provided with an exogenous source of glucose and calcium chloride.

In accordance with one embodiment, stem cell seeded engineered purified collagen based matrices are used as novel compositions for inducing the repair of damaged or disease tissues in vivo. In one embodiment the tissue graft construct comprises an engineered purified collagen based matrix, wherein the matrix is formed by contacting purified collagen with hydrochloric acid to produce a solubilized collagen composition and subsequently polymerizing the solubilized collagen composition under controlled conditions and in the presence of a population of cells to produce the engineered purified collagen based matrix containing cells entrapped within the matrix. In one embodiment the population of cells comprises stem cells initially added to the composition at a density of less than $10^5$ cells per milliliter, or the progeny of such stem cells. In one embodiment the stem cell seeded engineered purified collagen based matrices are implanted into a host without culturing the seeded stem cells in vitro. In another embodiment the stem cell seeded engineered purified collagen based matrix is further incubated under conditions suitable for inducing the proliferation and/or differentiation of the seeded stem cells.

In another embodiment the stem cells are added to the engineered purified collagen based matrices at densities of less than $10^3$ cells per milliliter and the cells are cultured under conditions that are minimally permissive for stem cell functionality. These conditions result in the production of localized populations of stem cells and thus allow for the isolation of clonal populations of stem cells. Accordingly, in one embodiment, a method of isolating clonal populations of individual stem cells is provided. The method comprises the steps of contacting a collagen based matrix with a low density of stem cells wherein said collagen matrix is formed by contacting a source of collagen with HCl to prepare a solubilized collagen composition, polymerizing the solubilized collagen composition using a final collagen concentration of 1.0 to 3.0 mg/ml, at a pH of about 6.5 to about 7.0. In one embodiment the initial seeded population of stem cells ranges from about 10 to about $10^3$ cells per milliliter. The seeded stem cells are cultured under conditions suitable for proliferation of the cells and individual populations of stem cells are isolated.

BRIEF DESCRIPTION OF THE DRAWINGS

FIG. 1A represents the effect of polymerization temperature on a matrix formed from a solubilized collagen composition comprising 1 mg/ml collagen in 1×PBS at pH 7.4; FIG. 1B represents the effect of the buffer type on a matrix formed from a solubilized collagen composition comprising 1 mg/ml collagen, and about 0.15 M NaCl at 37° C.; FIG. 1C represents the effect of pH (using a phosphate buffer) on a matrix formed from a solubilized collagen composition comprising 1 mg/ml collagen, in 1×PBS at pH 7.4; FIG. 1D represents the effect of pH (using a tris buffer) on a matrix formed from a solubilized collagen composition comprising 1 mg/ml collagen, in 50 mM tris, and about 0.15 M NaCl at 37° C. FIG. 1E represents the effect of ionic strength on a matrix formed from a solubilized collagen composition comprising 1 mg/ml collagen, no buffer, at 37° C.; FIG. 1F represents the effect of phosphate concentration on a matrix formed from a solubilized collagen composition comprising 1 mg/ml collagen, and about 0.15 M NaCl at 37° C.

FIGS. 4A and 4C represent 2D projections of confocal reflection image stacks showing changes to NHDF morphology and collagen fibril microstructure observed 5 hours after polymerization. FIGS. 4B and 4D represent quantified levels of local volumetric strain (matrix deformation) within the 3D tissue construct.

DETAILED DESCRIPTION

Definitions

Figure 1A:
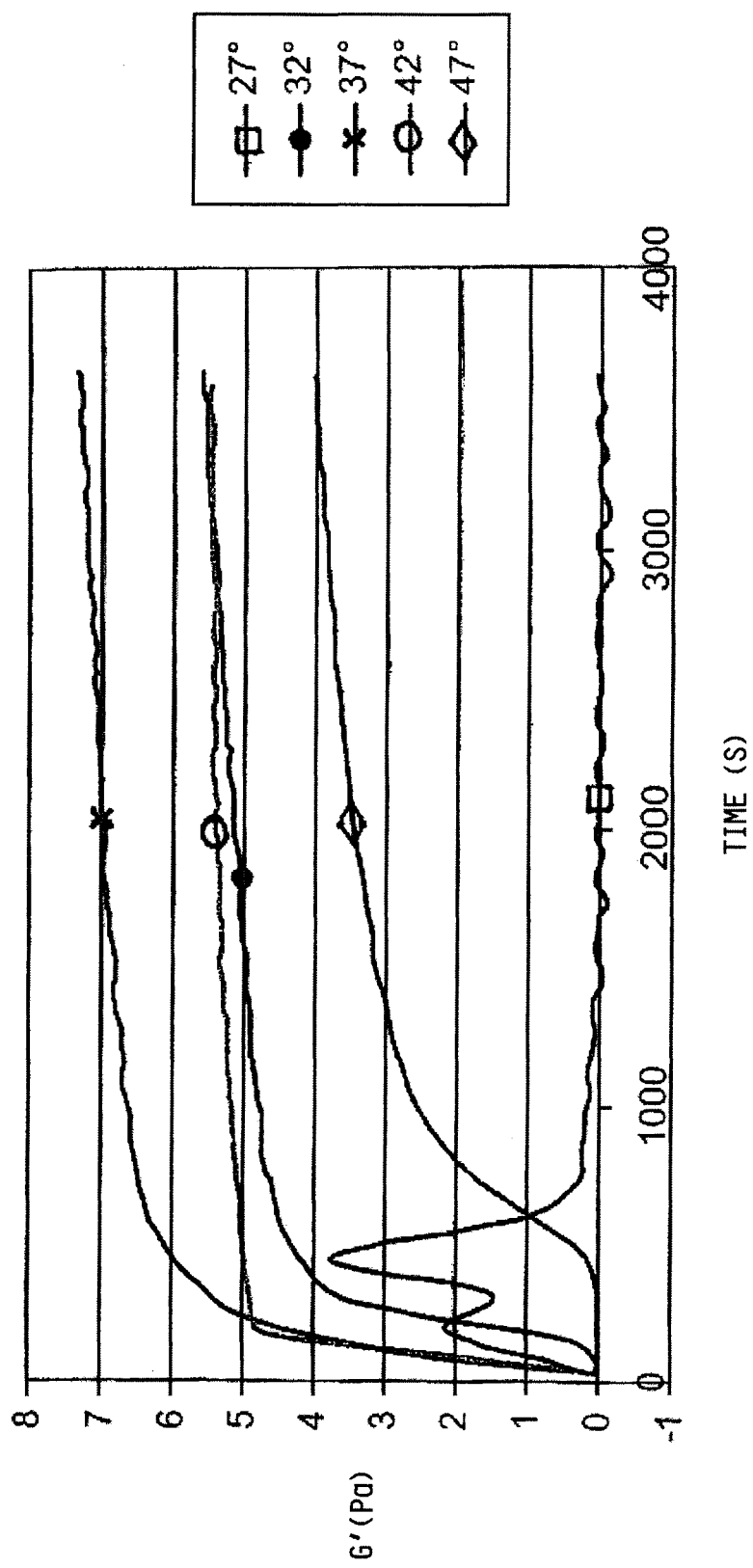
FIGS. 1A-1F present data showing the effect of various parameters on the stiffness (elastic or linear modulus) of the formed matrix.
Figure 1B:
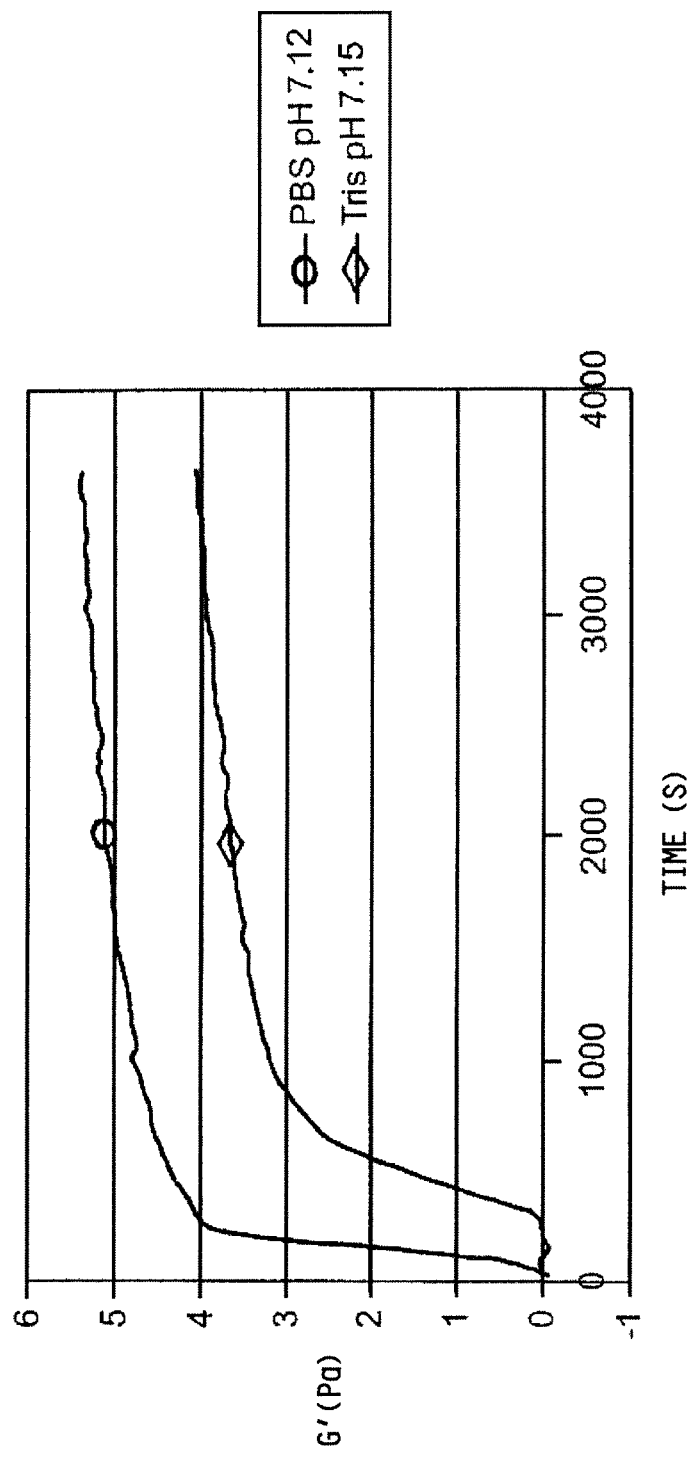
Figure 1C:
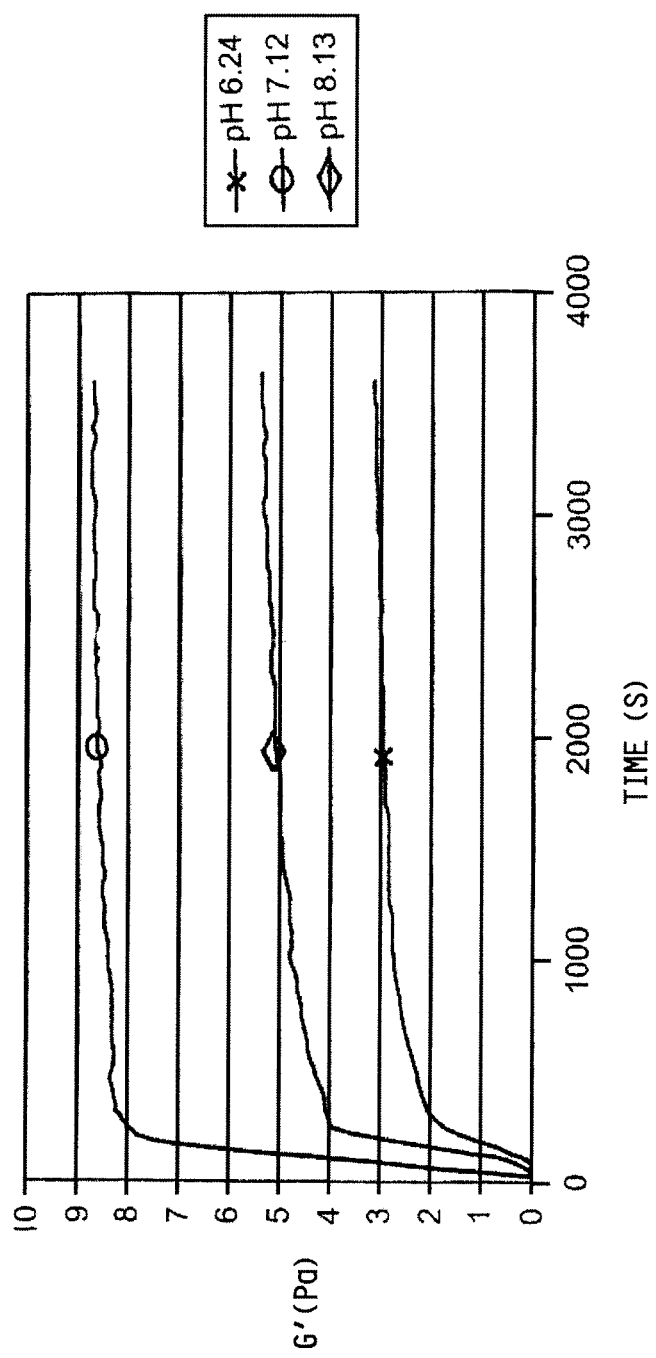
Figure 1D:
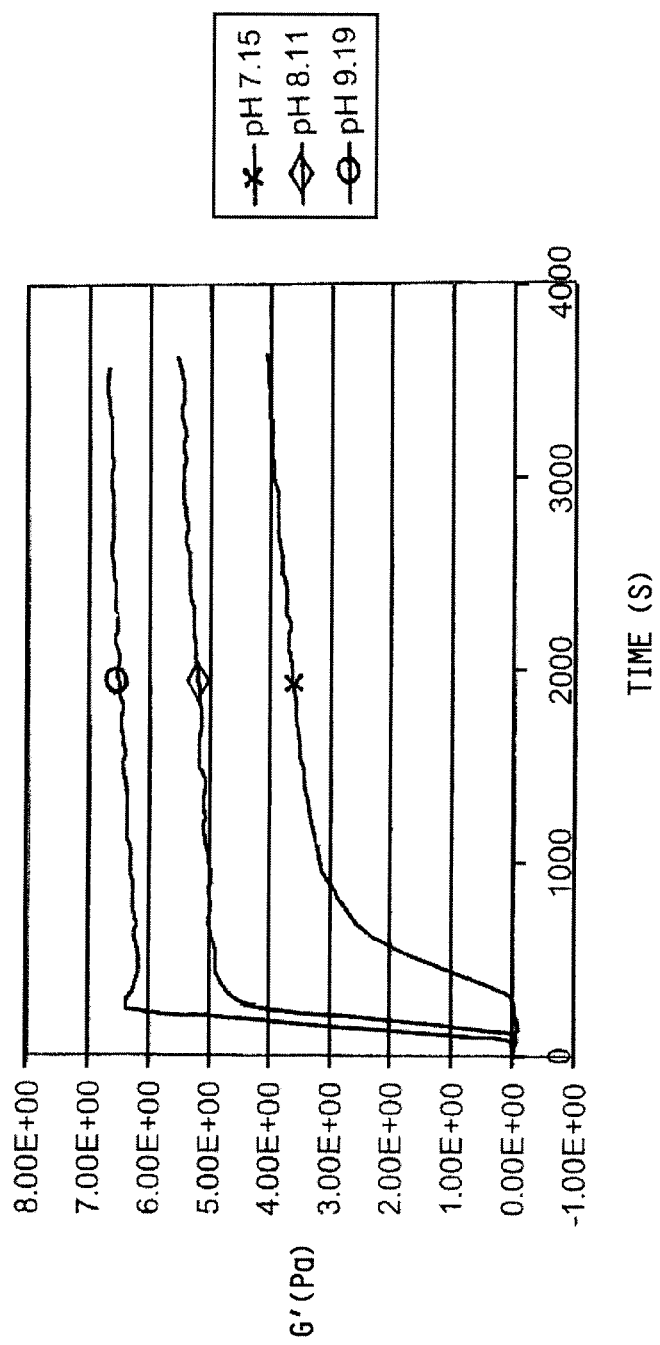
Figure 1E:
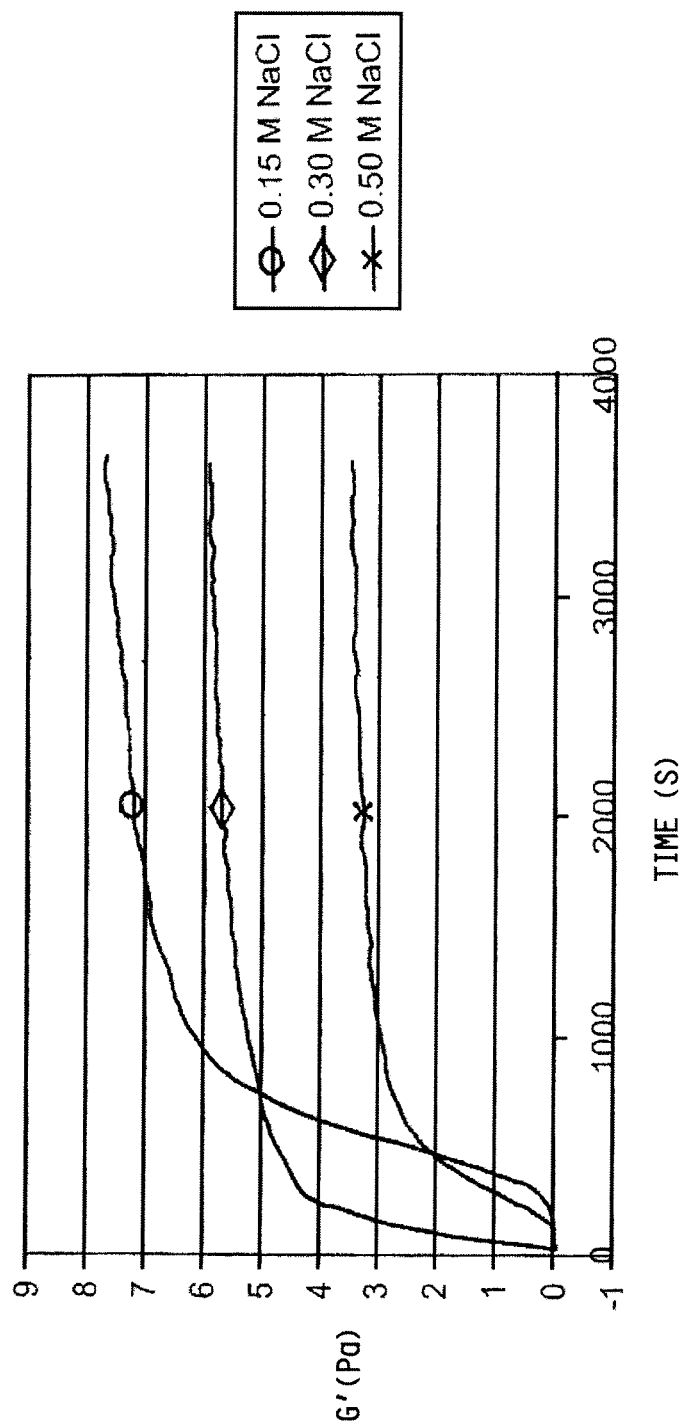
Figure 1F:
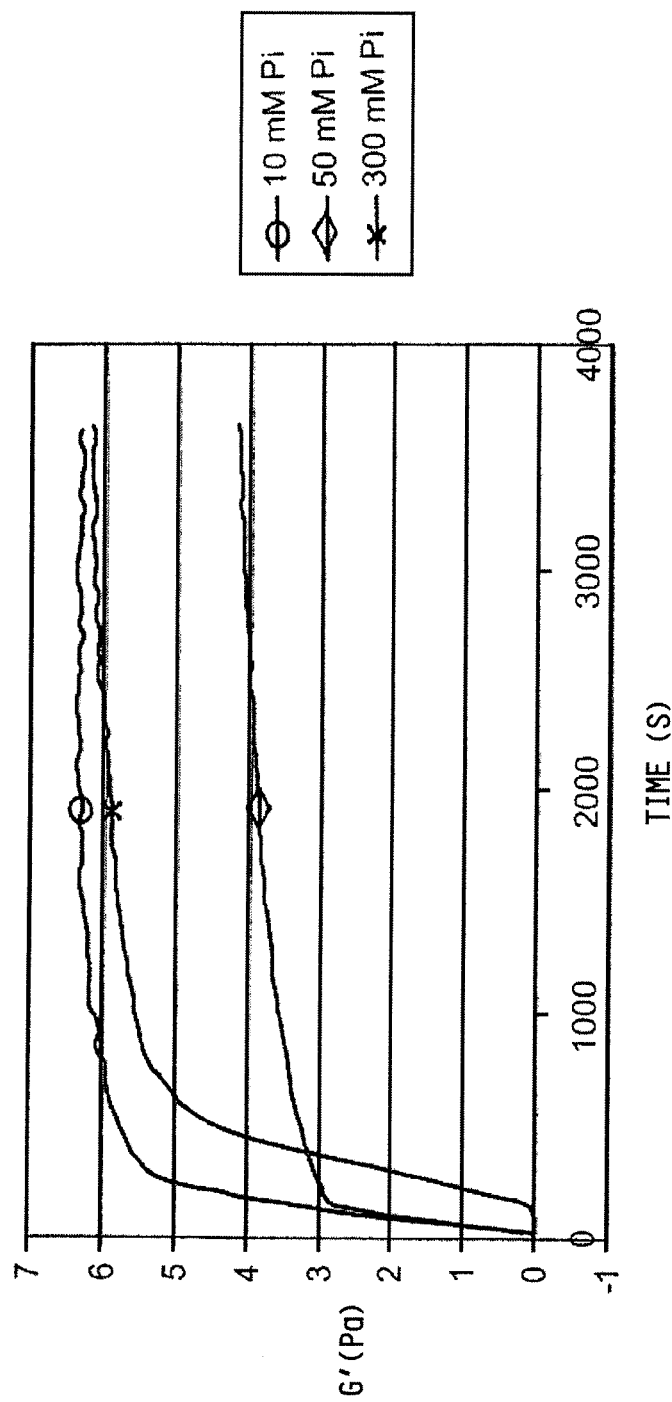
Figure 1G:
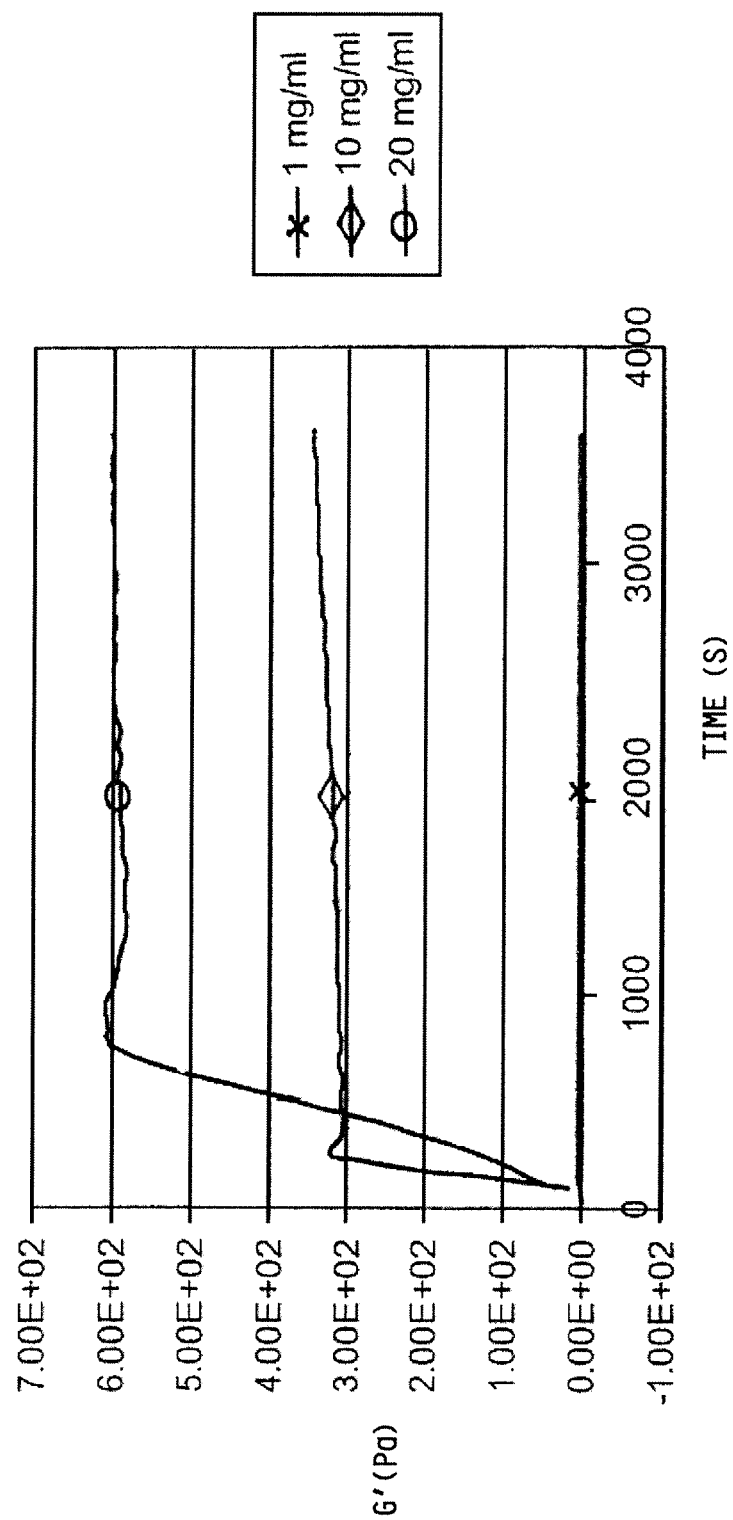
FIG. 1G represents the effect of SIS component concentration on a matrix formed from a solubilized ECM collagen composition in 1×PBS at 37° C.

As used herein, the term "stem cell" refers to an unspecialized cell from an embryo, fetus, or adult that is capable of self-replication or self-renewal and can develop into specialized cell types of a variety of tissues and organs. The term as used herein, unless further specified, encompasses totipotent cells (those cells having the capacity to differentiate into extra-embryonic membranes and tissues, the embryo, and all post-embryonic tissues and organs), pluripotent cells (those cells that can differentiate into cells derived from any of the three germ layers), and multipotent cells (those cells having the capacity to differentiate into a limited range of differentiated cell types).

As used herein the term "progenitor cell" refers to a stem cell with more specialization and less differentiation potential than a totipotent stem cell. For example, progenitor cells include unipotential cells (those cells having the capacity to differentiate along a single cell lineage).

As used herein, the term "lyophilized" relates to the removal of water from a composition, typically by freeze-drying under a vacuum. However, lyophilization can be performed by any method known to the skilled artisan and the method is not limited to freeze-drying under a vacuum. Typically, the lyophilized tissue is lyophilized to dryness, and in one embodiment the water content of the lyophilized tissue is below detectable levels.

As used herein "solubilized collagen composition" refers to a composition that comprises collagen in a predominantly soluble monomeric form (for example wherein less than 20% of the collagen is insoluble, denatured, or assembled in higher ordered structures).

As used herein "solubilized extracellular matrix composition" refers to a naturally occurring extracellular matrix that has been treated, for example, with an acid to reduce the molecular weight of at least some of the components of the extracellular matrix and to produce a composition wherein at least some of the components of the extracellular matrix have been solubilized from the extracellular matrix. The "solubilized extracellular matrix composition" may include insoluble components of the extracellular matrix as well as solubilized components.

As used herein the term "collagen-based matrix" refers to extracellular matrices that comprise collagen. An "engineered purified collagen based matrix" as used herein relates to a composition comprising a collagen fibril scaffold that has been formed under controlled conditions from a solubilized collagen composition, wherein the solubilized collagen composition is prepared from a composition consisting essentially of collagen. The conditions controlled during the polymerization reaction include one or more of the following: pH, phosphate concentration, temperature, buffer composition, ionic strength, and composition and concentration of purified collagen components. Similarly, an "engineered extracellular matrix" relates to a solubilized extracellular matrix composition that is polymerized to form a collagen fibril containing matrix under controlled conditions, wherein the controlled conditions include pH, phosphate concentration, temperature, buffer composition, ionic strength, and composition and concentration of the extracellular matrix components which includes both collagen and non-collagenous molecules. A "bioactive engineered extracellular matrix" composition refers to an engineered extracellular matrix composition that can be polymerized to form a three dimensional scaffold that is capable of remodeling tissues in vivo.

As used herein the term "naturally occurring extracellular matrix" comprises any noncellular material naturally secreted by cells (such as intestinal submucosa) isolated in their native configuration with or without naturally associated cells.

As used herein the term "submucosal matrices" refers to natural extracellular matrices, known to be effective for tissue remodeling, that have been isolated in their native configuration, including submucosa derived from vertebrate intestinal tissue, stomach tissue, bladder tissue, alimentary tissue, respiratory tissue and genital tissue.

As used herein the term "exogenous" or "exogenously added" designates the addition of a new component to a composition, or the supplementation of an existing component already present in the composition, using material from a source external to the composition.

As used herein "sterilization" or "sterilize" or "sterilized" means removing unwanted contaminants including, but not limited to, endotoxins, nucleic acid contaminants, and infectious agents.

As used herein "stiffness" or elastic or linear modulus" refers to the fundamental material property defined by the slope linear portion of a stress-strain curve that results from conventional mechanical testing protocols.

As used herein, the term "purified" and like terms relate to the isolation of a molecule or compound in a form that is substantially free from other components with which they are naturally associated (e.g., the total amount of nondesignated components present in the composition representing less than 5%, or more typically less than 1%, of total dry weight).

As used herein the term "three dimensional purified collagen matrix (3D matrix)" refers to an engineered purified collagen based matrix, as defined above, and the fluid that surrounds the collagen fibril network. A "3D purified collagen matrix populated/seeded with cells" further comprises a viable population of cells contained within the matrix.

As used herein the term "three dimensional extracellular matrix (3D ECM)" refers to an engineered extracellular matrix, as defined above, and the fluid that surrounds the collagen fibril network. A "3D extracellular matrix populated/seeded with cells" further comprises a viable population of cells contained within the matrix.

As used herein the term "three dimensional matrix (3D matrix)" is a generic term that is intended to include both "three dimensional purified collagen matrices (3D purified collagen matrices)" as well as "three dimensional extracellular matrices (3D ECM).

As used herein the term "collagen fibril" refers to a quasi-crystalline, filamentous structure formed by the self-assembly of soluble trimeric collagen molecules. The collagen molecules in a collagen fibril typically pack in a quarter-staggered pattern giving the fibril a characteristic striated appearance or banding pattern along its axis. Solubilized collagen that is assembled in vitro to form collagen fibrils exhibit similarities to collagen structures found in vivo (Veis and George, 1994 Fundamental of interstitial collagen assembly. In: Yurchenco P D, Birk D E, and Mecham R P (eds.), Extracellular Matrix Assembly and Structure, Academic Press, Inc., San Diego, pp. 15-45). Within tissues in vivo, collagen fibrils are organized as bundles in a hierarchical manner to form fibers. Collagen fibers are further organized in a tissue-specific fashion to provide tissues with specific structural-functional properties. Collagen fibrils are distinct from the amorphous aggregates or precipitates of insoluble collagen that can be formed by dehydrating (e.g., lyophilization) collagen suspensions to form porous network scaffolds. Collagen networks formed from amorphous aggregates, or precipitates of insoluble collagen, have characteristics that distinct from those formed from collagen fibrils as defined above.

Embodiments

Cell culture scaffolds presenting a more biologically relevant microenvironment are disclosed. More particularly, these cell culture scaffolds comprise three-dimensional matrices/biomaterials that are created from solubilized collagen compositions. The solubilized collagen compositions are prepared from biological sources, such as naturally occurring extracellular matrices, including for example submucosal matrices. More particularly, the soluble polymers suitable for use in the present invention can be isolated, to varying degrees of purity, from natural tissues and include, but are not limited to, type I collagen, type III collagen, growth factors and glycosaminoglycans. In one embodiment the solubilized collagen composition comprises purified type I collagen or a mixture of purified type I and type III collagen. When provided with the proper conditions, the solubilized collagen composition undergoes polymerization/self assembly to form a three dimensional scaffold/biomaterial comprised of collagen fibrils. In one embodiment the soluble polymers comprise type I collagen monomers, where upon polymerization the resulting scaffolds represent a composite material comprising insoluble collagen fibrils and an interfibrillar fluid component, referred to herein as a three dimensional matrix.

An array of scaffolds/biomaterials can be created by varying the composition of ECM molecules as well as the self-assembly/polymerization conditions. Surprisingly, applicants have discovered that upon seeding progenitor cells or stem cells within engineered purified collagen based matrices (scaffolds) representing different microstructural compositions (e.g., having different dimensioned and organizations of the collagen fibrils and filaments), distinct patterns of cell survival, growth, proliferation, and differentiation are obtained. In particular, applicants have discovered that engineered purified collagen based matrices representing different microstructural compositions (e.g., varied fibril dimensions (length, diameter) and densities) will impact the rate of cell proliferation as well as the pattern of cellular condensation, aggregation, fusion, and cellular differentiation events and their associated time-line. These results are significant because they indicate that engineered purified collagen based matrices can be specifically designed to foster the proliferation of stem cells while maintaining their precursor or multipotential status. Furthermore, engineered purified collagen based matrices can be designed to direct differentiation of cells down a specific cell lineage (such as fat, bone, muscle, or cartilage) to form 3D organotypic tissues (that is reminiscent of in vivo tissue structure and function).

In accordance with one embodiment, stem cells and/or progenitor cells are seeded at relatively low densities on or within the various engineered purified collagen based matrices. It is known that, in general, cell behavior is determined by a combination of signal inputs arising from soluble factors, biophysical factors, the extracellular matrix substrate, and cell-cell interactions. Seeding cells at a relative low cell density on or within the collagen based matrices of the present invention allows ECM-based signaling to predominate over signals derived from cell-cell interactions. In accordance with one embodiment, cells are initially seeded on or within the engineered purified collagen based matrices at a minimal cell density that will allow for cell viability and replication (i.e., the minimal functionality density). This minimal functional density can be easily established for the particular cell type to be cultured and for the specific culture conditions utilized.

In accordance with one embodiment the stem cells or progenitor cells are seeded within the collagen based matrix at a cell density substantially higher than the minimal functionality density but at a relative low density compared to standard cell culture techniques. In one embodiment the cells comprise stem cells, wherein the cells are seeded at a density within 3 orders of magnitude of the minimal functionality density, in another embodiment stem cells are seeded at a density within 2 orders of magnitude of the minimal functionality density, and in another embodiment the stem cells are seeded at a density within an order of magnitude of the minimal functionality density. The stem cells can be seeded at a relatively high density of about $1\times10^6$ to about $1\times10^8$ cells/ml, or at a more typical density of about $1\times10^3$ to about $1\times10^5$ cells/ml. Seeding the cells at the relative high density of about $1\times10^6$ to about $1\times10^8$ cells/ml will promote cell to cell interactions over cell to matrix interactions. Accordingly, stem cells seeded at relatively high densities will develop into fat tissue even when the cells are cultured within 3D matrices of high collagen fibril density. In one embodiment stem cells are seeded at a density of less than $5\times10^4$ cells/ml, more typically at a density of about $5\times10^4$ cells/ml. In another embodiment stem cells are seeded at a density of less than $1\times10^4$ cells/ml, in another embodiment stem cells are seeded at a density selected from a range of about $1\times10^2$ to about $5\times10^3$.

As disclosed herein an improved method for culturing stem cells is provided that uses three dimensional purified collagen based matrices. The improved method allows for enhanced proliferation of stem cells as well as better control over the differentiation of the cultured cells. In one embodiment the method comprises the steps of providing a solubilized collagen composition, adding cells to the collagen composition, and polymerizing the solubilized collagen composition to form collagen fibrils. The solubilized collagen composition comprises collagen that has been isolated with or without additional components from natural tissues.

In accordance with one embodiment the solubilized collagen composition is prepared using purified type I collagen as a starting material. In one embodiment collagen, and more particularly type I or type III collagen, that has been isolated from tissues is subjected to a final purification step that removes any reagents that were used during the isolation steps. In one embodiment the final purification step comprises dialyzing the isolated collagen in an aqueous solution, and in one embodiment the isolated collagen is dialyzed against a dilute acid solution, including for example, hydrochloric acid. In one embodiment the final purification step comprises dialyzing the isolated collagen against a 0.01 N HCl solution. Isolated type I or isolated type III collagen preparations are commercially available, and these commercially available materials are subjected to a further purification step, including for example, dialyzing against a dilute (about 0.001 N to about 0.1 N) hydrochloric acid solution to produce purified collagen suitable for use for forming 3D purified collagen matrices. The dialysate can optionally be filtered and/or centrifuged to remove particulate matter. In accordance with one embodiment, the collagen component of the solubilized collagen composition consists essentially of purified collagen, the majority of which are in monomeric form. In a further embodiment the composition is formed from purified collagen (the majority of which are in monomeric form) that is greater than 75% type I collagen, or greater than 90% type I collagen. In one embodiment a composition consisting essentially of purified collagen is dissolved in an acid solution, such as hydrochloric acid to prepare a solubilized collagen composition of the desired concentration. In one embodiment the purified collagen is dissolved in about 0.001 N to about 0.1 N, from about 0.005 N to about 0.1 N, from about 0.005 N to about 0.01 N, from about 0.01 N to about 0.1 N, from about 0.05 N to about 0.1 N, from about 0.001 N to about 0.05 N, about 0.001 N to about 0.01 N, or from about 0.01 N to about 0.05 N hydrochloric acid solution.

In another embodiment, a three dimensional purified collagen matrix is provided, wherein the matrix is formed from a solubilized collagen composition wherein the collagen components of the solubilized collagen composition consist essentially of purified type I and type III collagen. The component fibrils of such matrices have been found to have a greater degree of flexibility relative to the fibrils of engineered purified collagen matrices that are formed using only type I collagen. In one embodiment the matrix comprises type I collagen and type III collagen in a ratio of 200:1. The method of forming matrices with fibrils that exhibit a higher degree of flexibility comprises the steps of combining in vitro at least 100 ug/ml of type I collagen with at least 0.5 ug/ml of type III collagen to obtain a total amount of collagen, and forming in vitro a three dimensional purified collagen matrix wherein the three dimensional matrix has decreased stiffness compared to a 3D matrix formed in vitro with type I collagen when the total amount of collagen in the two matrices is equivalent.

In another embodiment, a method of preparing an extracellular matrix composition is provided. The method comprises the steps of combining in vitro at least 100 ug/ml of type I collagen with at least 0.5 ug/ml of type III collagen to obtain a total amount of collagen, and forming in vitro a three dimensional matrix. In one embodiment the type I and type III collagen is dissolved in about 0.001 N to about 0.1 N, from about 0.005 N to about 0.1 N, from about 0.005 N to about 0.01 N, from about 0.01 N to about 0.1 N, from about 0.05 N to about 0.1 N, from about 0.001 N to about 0.05 N, about 0.001 N to about 0.01 N, or from about 0.01 N to about 0.05 N hydrochloric acid solution either before or after the combining step.

In another embodiment, an extracellular matrix composition for use in repairing diseased or damaged tissues is provided. The extracellular matrix composition comprises at least 100 ug/ml of type I collagen and at least 0.5 ug/ml of type III collagen, wherein the type I collagen to type III collagen ratio is selected from the group consisting of 200:1, 100:1, 50:1, 15:1, 10:1, 8:1, 6:1, 5:1, 3:1, and 2:1, and a population of cells. The matrix is formed by provided a solubilized collagen composition comprising type I and type III collagen, in a ratio selected from the group consisting of 200:1, 100:1, 50:1, 15:1, 10:1, 8:1, 6:1, 5:1, 3:1, and 2:1, polymerizing the solubilized collagen composition to form collagen fibrils, and adding cells to the collagen composition either before or after the polymerization step. In one embodiment a composition comprising solubilized collagen and stem cells is injected into a host and the polymerization of the solubilized collagen composition occurs in vivo to form a cell entrapping matrix. Alternatively, the solubilized collagen composition can be polymerized in vitro and the polymerized matrix, comprising the population of cells, can be subsequently injected or implanted in a host. In another embodiment the population of cells entrapped within the 3D matrix can be cultured in vitro, for a predetermined length of time, to increase cell numbers and/or induce differentiation of the cell population prior to implantation into a host. In a further embodiment, the population of cells can be cultured in vitro, for a predetermined length of time, to increase cell numbers and/or induce differentiation of the cell population and the cells can be separated from the matrix and implanted into the host in the absence of the polymerized matrix.

In one illustrative embodiment, the engineered purified collagen based matrix comprises type III collagen in the range of about 0.5% to about 33% of total collagen in the matrix. In another illustrative embodiment, the engineered purified collagen based matrix comprises type I collagen in the range of about 66% to about 99.5% of total collagen in the matrix. In yet another illustrative embodiment, the type I collagen to type III collagen ratio is in the range of about 2:1 to about 200:1, wherein the type I collagen to type III collagen ratio may be selected from the group consisting of 200:1, 100:1, 50:1, 15:1, 10:1, 8:1, 6:1, 5:1, 3:1, and 2:1.

In another embodiment, a method of enhancing cell proliferation within an extracellular matrix composition is provided. The method comprises the steps of combining in vitro an amount of type I collagen with an amount of type III collagen to obtain a total amount of collagen wherein the ratio of type III collagen to type I collagen is at least 1:6, and forming in vitro a three-dimensional extracellular matrix wherein the extracellular matrix enhances cell proliferation compared to an extracellular matrix formed in vitro with type I collagen wherein the amount of type I collagen is equivalent to the total amount of type I collagen in the combining step. In yet another embodiment, the method comprises the steps of combining in vitro at least 3 ug/ml of type I collagen with at least 0.5 ug/ml of type III collagen to obtain a total amount of collagen wherein the ratio of type III collagen to type I collagen is at least 1:6, and forming in vitro a three-dimensional extracellular matrix wherein the extracellular matrix enhances cell proliferation compared to an extracellular matrix formed in vitro with type I collagen, wherein the amount of type I collagen is equivalent to the total amount of type I collagen in the combining step.

In another illustrative embodiment, the method of preparing an engineered purified collagen based matrix comprises combining type I and type III collagen wherein the type III collagen is added in the range of about 17% to about 33% of total collagen in the matrix. In another illustrative embodiment, the type I collagen is added in the range of about 66% to about 83% of total collagen in the matrix. In yet another illustrative embodiment, the type I collagen to type III collagen ratio is in the range of about 6:1 to about 1:1, wherein the type I collagen to type III collagen ratio may be selected from the group consisting of 6:1, 5:1, 4:1, 3:1, 2:1, and 1:1.

Applicants have also discovered that the concentration of total collagen present in solubilized collagen composition will impact the microstructure of the matrix, and the behavior of stem cells cultured within a matrix polymerized from such a composition. 3D matrices can be prepared from solubilized collagen compositions having purified collagen concentrations ranging from as little as 0.05 mg/ml to as much as 40 mg/ml. Typically the 3D matrices are prepared from purified solubilized collagen compositions having a collagen concentration selected from a range of about 0.1 mg/ml to about 5.0 mg/ml, and in one embodiment about 1.5 mg/ml to about 3.0 mg/ml. Table 1 summarizes the effect of total collagen concentration on the fibril structure of the matrix:

TABLE 1

Microstructure and Mechanical Properties of 3D Purified Collagen Matrices

| Collagen Concentration | Fibril Area Fraction (Density; %) | Stiffness (Linear Modulus; kPa) | Fibril Diameter (confocal reflection microscopy; nm) | Fibril Diameter (scanning electron microscopy, nm) |
|---|---|---|---|---|
| 0.3 mg/ml, pH 7.4 |  | 1.54 ± 0.507 | 418 ± 121 |  |
| 1 mg/ml, pH 7.4 | 11.5 ± 1.9 | 10.7 ± 1.93 | 446 ± 65 |  |
| 1.5 mg/ml, pH 7.4 | 12 ± 1.4 | 8.5 ± 1.65 | 412.63 ± 76 | 115.16 ± 23.18 |
| 2 mg/ml, pH 7.4 | 14.8 ± 4.25 | 16.6 ± 2.68 | 435 ± 61 | 80.8 ± 18.3 |
| 3 mg/ml, pH 7.4 | 18.4 ± 1.9 | 24.3 ± 4.16 | 430 ± 71 |  |
| 2 mg/ml, pH 6 |  | 1.84 ± 0.701 | 490 ± 96 |  |
| 2 mg/ml, pH 7 |  | 12.7 ± 1.18 | 469 ± 73 |  |
| 2 mg/ml, pH 7.4 |  | 16.6 ± 2.68 | 435 ± 61 |  |
| 2 mg/ml, pH 8 |  | 22.5 ± 3.65 | 421 ± 62 |  |
| 2 mg/ml, pH 9 |  | 33.0 ± 6.93 | 392 ± 65 |  |
| 1.5 mg/ml type I + 0.75 mg/ml type III | 21.5 ± 2.6 | 13.3 ± 1.4 | 385 ± 72 | 87 ± 17 |

Using the data of Table 1 and assuming a linear relationship between collagen concentration and the measure properties, predictions of fibril area fraction and matrix stiffness can be determined as a function of collagen concentration using the following equations:

Fibril Area Fraction=3.6514×Collagen Concentration+7.3286

$R^2$=0.9681

Stiffness=8.1145×Collagen Concentration−0.3306

$R^2$=0.9304

Prediction of Stiffness as a function of Fibril Diameter (Assumption: fibril area fraction does not change; relationship based upon pH data):

Stiffness=−0.2916×Fibril Diameter+146.02

$R^2$=0.9581 (based upon pH data)

The 3D matrices formed in accordance with the present disclosure represent a matrix of collagen fibrils. The fibrils of the matrices are formed at a fibril area fraction (density) of about 7.7% to about 25% total volume. In one embodiment the 3D matrices have a fibril area fraction of about 12.8% to about 18.3% total volume. In another embodiment the 3D matrices have a fibril area fraction of about 18.5% to about 25% total volume. In one embodiment the 3D matrix has a fibril area fraction of about 12.8% to about 18.3% total volume and the fibrils have a hydrated diameter of about 350 to about 475 nm. In another embodiment the 3D matrix has a fibril area fraction of about 18.5% to about 25% total volume and the fibrils have a hydrated diameter of about 375 to about 500 nm.

Three dimensional matrices having low fibril density and low stiffness enhance stem cell proliferation with decreased differentiation of the cells. Accordingly, 3D matrices formed from solubilized collagen compositions having about 0.1 mg/ml to about 3 mg/ml collagen, and more typically about 0.5 mg/ml to about 2.5 mg/ml collagen are utilized to stimulate stem cell proliferation. The 3D matrices so formed will have a fibril predicted fibril area fraction (density) of about 7.7% to about 18.3% total volume and about 9.2% to about 16.5% total volume, respectively. In one embodiment the 3D matrices are formed from solubilized collagen compositions having about 3 mg/ml to about 1.5 mg/ml collagen and in one embodiment the solubilized collagen compositions have about 2.5, 2.0, 1.5, or 1.0 mg/ml of collagen. Alternatively, higher concentrations of total collagen present in the three dimensional matrix leads to differentiation of stem cells. Accordingly, 3D matrices (having a fibril area fraction of at least about 18% total volume) formed from solubilized collagen compositions having more than about 3 mg/ml are utilized to stimulate differentiation of stem cells cultured within the matrix. In one embodiment the 3D matrices are formed from solubilized collagen compositions having about 3.2, 3.4, 3.6, 3.8, 4.0, 4.5 or 5.0 mg/ml of collagen, resulting in 3D matrices having a fibril area fraction of about 19%, 19.7%, 20.5%, 21.2%, 22%, 23.8% and 25.6% total volume, respectively.

As reported herein the relative stiffness (elastic or linear modulus) of a 3D matrix can be modified by controlling the relative proportion of type I to type III collagen, the fibril area fraction (density), or the fibril diameter of the collagen fibrils in the 3D matrix. In accordance with one embodiment 3D matrices are prepared having a relatively low stiffness (elastic or linear modulus) of about 0.48 to about 24.0 kPa. In one embodiment these matrices are used to propagate stem cells and progenitor cells without further differentiation of the cells and/or their progeny. In another embodiment 3D matrices are prepared having a relatively high stiffness of about 25 to about 40 kPa. In one embodiment these relatively stiffer matrices are used to induce the differentiation of stem cells and progenitor cells and/or their progeny. In one embodiment a 3D matrix is provided having a relatively low stiffness of about 0.48 to about 24.0 kPa and a relatively low fibril area fraction (density) of about 7% to about 18% total volume. In an alternative embodiment a 3D matrix is provided having a relatively high stiffness of about 25 to about 40 kPa and a relatively high fibril area fraction (density) of about 19% to about 26% total volume.

In another embodiment the solubilized collagen composition comprises collagen monomers isolated from natural tissues, and includes additional components that are naturally associated with the native tissues and/or exogenously added components. In one embodiment various exogenous materials, such as growth factors are added to the collagen based matrices of the present invention. In one embodiment the solubilized collagen composition represents a solubilized fraction of a naturally occurring extracellular matrix, and in one embodiment the naturally occurring extracellular matrix is a vertebrate submucosal matrix. In one embodiment the solubilized collagen composition represents a solubilized fraction of vertebrate intestinal submucosa.

In other embodiments, acetic acid, formic acid, lactic acid, citric acid, sulfuric acid, ethanoic acid, carbonic acid, nitric acid, or phosphoric acid can be used to solubilize the naturally occurring extracellular matrix (or a purified lyophilized collagen composition) to produce a solubilized collagen composition. The solubilized collagen composition derived from a naturally occurring extracellular matrix, such as vertebrate intestinal submucosa, can then be polymerized to form an engineered extracellular matrix.

The invention also relates to methods of preparation and compositions comprising solubilized extracellular matrix components polymerized in vitro where the extracellular matrix components are solubilized by other methods known in the art. The polymerizing step can be performed under conditions that are systematically varied where the conditions are selected from the group consisting of pH, phosphate concentration, temperature, buffer composition, ionic strength, the extracellular matrix components in the solubilized extracellular matrix composition, and the concentration of the extracellular matrix components in the solubilized extracellular matrix composition.

In accordance with one embodiment a method of forming a 3D matrix comprising stem cells is provided. The method comprises the steps of providing an acid solubilized purified type I collagen composition. In one embodiment the collagen composition further comprises type III collagen. In one embodiment the purified collagen represents a commercially available isolated preparation of collagen that is further subjected to purification, including for example dialyzing against an solution of about 0.005 N to about 0.1 N HCl, more typically about 0.01 N HCl. Typically the solubilized collagen composition comprises purified collagen that is suspended in about 0.005 N to about 0.1 N HCl solution, and in one embodiment suspended in 0.01N HCl. The solubilized collagen composition is also typically sterilized using standard techniques including for example contact with chloroform or peracetic acid. Stem cells are then added to the solubilized collagen composition at a specific density, typically ranging from about $1 \times 10^3$ to about $1 \times 10^8$. In one embodiment the stem cells are added to the solubilized collagen composition at a concentration of less than $5 \times 10^4$ cells per milliliter, and in one embodiment the cells are added at a density of about 10 to about $10^3$ per milliliter. In accordance with one embodiment the collagen/cell suspension is then pipetted into a well plate and allowed to polymerize in a humidified environment at 37° C. for approximately 30 minutes. In an alternative embodiment the collagen/cell suspension is injected into a host and the composition is polymerized in vivo.

As noted above solubilized collagen compositions can be prepared from vertebrate submucosal matrices wherein the collagen compositions comprise additional components besides collagen. Vertebrate submucosal matrices can be obtained from various sources, including intestinal tissue harvested from animals raised for meat production, including, for example, pigs, cattle and sheep or other warm-blooded vertebrates. According to one embodiment the solubilized collagen composition is derived from one or more sources selected from the group consisting of intestinal submucosa, stomach submucosa, urinary bladder submucosa, uterine submucosa, and any other submucosal material that can be used to remodel endogenous tissue.

In one embodiment the submucosa comprises the tunica submucosa delaminated from both the tunica muscularis and at least the luminal portion of the tunica mucosa of a warm-blooded vertebrate. Such constructs can be prepared by mechanically removing the luminal portion of the mucosa and the external muscle layers and lysing resident cells with hypotonic washes.

It is known that compositions comprising the tunica submucosa delaminated from both the tunica muscularis and at least the luminal portion of the tunica mucosa of the submucosal tissue of warm-blooded vertebrates can be used as tissue graft materials (see, for example, U.S. Pat. Nos. 4,902,508 and 5,281,422 incorporated herein by reference). Such submucosal tissue preparations are characterized by excellent mechanical properties, including high compliance, high tensile strength, a high burst pressure point, and tear-resistance.

Submucosa-derived matrices are collagen based biodegradable matrices comprising highly conserved collagens, glycoproteins, proteoglycans, and glycosaminoglycans in their natural configuration and natural concentration. Such submucosal material serves as a matrix for the regrowth of endogenous tissues at the implantation site (e.g., biological remodeling). The submucosal material serves as a rapidly vascularized matrix for support and growth of new endogenous connective tissue. Thus, submucosa matrices have been found to be trophic for host cells of tissues to which it is attached or otherwise associated in its implanted environment. In multiple experiments submucosal tissue has been found to be remodeled (resorbed and replaced with autogenous differentiated tissue) to assume the characterizing features of the tissue(s) with which it is associated at the site of implantation or insertion.

Small intestinal submucosa tissue is an illustrative source of submucosal tissue for use in this invention. Submucosal tissue can be obtained from various sources, for example, intestinal tissue can be harvested from animals raised for meat production, including, pigs, cattle and sheep or other warm-blooded vertebrates. Small intestinal submucosal tissue is a plentiful by-product of commercial meat production operations and is, thus, a low cost material.

Suitable intestinal submucosal tissue typically comprises the tunica submucosa delaminated from both the tunica muscularis and at least the luminal portion of the tunica mucosa, but other tissue constructs can also be used. In one illustrative embodiment the intestinal submucosal tissue comprises the tunica submucosa and basilar portions of the tunica mucosa including the lamina muscularis mucosa and the stratum compactum which layers are known to vary in thickness and in definition dependent on the source vertebrate species.

The preparation of submucosal tissue is described in U.S. Pat. No. 4,902,508, the disclosure of which is expressly incorporated herein by reference. A segment of vertebrate intestine, for example, preferably harvested from porcine, ovine or bovine species, but not excluding other species, is subjected to abrasion using a longitudinal wiping motion to remove the outer layers, comprising smooth muscle tissues, and the innermost layer, i.e., the luminal portion of the tunica mucosa. The submucosal tissue is rinsed under hypotonic conditions, such as with water or with saline under hypotonic conditions, and is optionally sterilized.

The submucosal tissue can be sterilized using conventional sterilization techniques including glutaraldehyde tanning, formaldehyde tanning at acidic pH, propylene oxide or ethylene oxide treatment, gas plasma sterilization, gamma radiation, electron beam, and/or peracetic acid sterilization. Sterilization techniques which do not adversely affect the structure and biotropic properties of the submucosal tissue can be used. An illustrative sterilization technique is exposing the submucosal tissue to peracetic acid, 1-4 Mrads gamma irradiation (or 1-2.5 Mrads of gamma irradiation), ethylene oxide treatment, exposure to chloroform, or gas plasma sterilization. The submucosal tissue can be subjected to one or more sterilization processes. In illustrative embodiments, the intact extracellular matrix material can be sterilized with peracetic acid or the solubilized collagen composition can be sterilized. The submucosal tissue can be subjected to one or more sterilization processes. The submucosal tissue can be stored in a hydrated or dehydrated state prior to solubilization in accordance with the invention.

Extracellular matrix-derived tissues other than intestinal submucosa tissue may be used in accordance with the methods described herein and used as a source for preparing solubilized collagen compositions. Methods of preparing and treating other extracellular matrix-derived tissues are known to those skilled in the art and may be similar to the methods described above. For example, see U.S. Pat. No. 5,163,955 (pericardial tissue), U.S. Pat. No. 5,554,389 (urinary bladder submucosa tissue), U.S. Pat. No. 6,099,567 (stomach submucosa tissues), U.S. Pat. No. 6,576,265 (extracellular matrix tissues generally), U.S. Pat. No. 6,793,939 (liver basement membrane tissues), and U.S. patent application publication no. US 2005/0019419 A1 (liver basement membrane tissues), and WO 01/45765 (extracellular matrix tissues generally), each incorporated herein by reference. The preparation and use of submucosa tissues as graft compositions is also described in U.S. Pat. Nos. 4,902,508, 5,281,422, and 5,275,826, each incorporated herein by reference.

In one illustrative embodiment, the extracellular matrix material is solubilized with an acid and the solubilized fraction is recovered for polymerization to form the collagen based matrices of the present invention. Typically, prior to solubilization, the source extracellular matrix material is comminuted by tearing, cutting, grinding, or shearing the harvested extracellular matrix material. In one illustrative embodiment, the extracellular matrix material can be comminuted by shearing in a high-speed blender, or by grinding the extracellular matrix material in a frozen or freeze-dried state, and then lyophilizing the material to produce a powder having particles ranging in size from about 0.1 mm$^2$ to about 1.0 mm$^2$. The extracellular matrix material powder can thereafter by hydrated with, for example, water or buffered saline to form a fluid or liquid or paste-like consistency. In one illustrative embodiment, the extracellular matrix tissue is comminuted by freezing and pulverizing under liquid nitrogen in an industrial blender. The preparation of fluidized forms of the source extracellular matrix material, such as submucosa tissue, is described in U.S. Pat. No. 5,275,826, the disclosure of which is expressly incorporated herein by reference.

In one illustrative embodiment, an acid, such as hydrochloric acid, acetic acid, formic acid, sulfuric acid, ethanoic acid, carbonic acid, nitric acid, or phosphoric acid, is used to solubilize the source extracellular matrix material. In various illustrative embodiments, the acidic conditions for solubilization can include solubilization at about 0° C. to about 60° C., and incubation periods of about 5 minutes to about 96 hours. In other illustrative embodiments, the concentration of the acid, such as hydrochloric acid, can be from about 0.001 N to about 0.1 N, from about 0.005 N to about 0.1 N, from about 0.01 N to about 0.1 N, from about 0.05 N to about 0.1 N, from about 0.001 N to about 0.05 N, about 0.001 N to about 0.01 N, or from about 0.01 N to about 0.05 M. However, the solubilization can be conducted at any temperature, for any length of time, and at any concentration of acid.

Any of the source extracellular matrix materials described above can be used and the solubilization step can be performed in the presence of an acid or in the presence of an acid and an enzyme. The acid solubilization step results in a solubilized extracellular matrix composition that remains bioactive (i.e., is capable of polymerizing and remodeling tissues in vivo) after lyophilization.

In one illustrative embodiment, the extracellular matrix material is treated with one or more enzymes before, during, or after the acid solubilization step. For enzymes that are inactive at acidic pH, for example, the extracellular matrix material is treated with the enzyme before the acid solubilization step or after the acid solubilization step, but under conditions that are not acidic. Enzymatic digestion of the extracellular matrix material is conducted under conditions that are optimal for the specific enzyme used and under conditions that retain the ability of the solubilized components of the extracellular matrix material to polymerize. The concentration of the enzyme depends on the specific enzyme used, the amount of extracellular matrix material to be digested, the desired time of digestion, and the desired temperature of the reaction. In various illustrative embodiments, about 0.01% to about 0.5% (weight per volume, such that 0.01% is equivalent to 0.01 g/100 ml) of enzyme is used. Exemplary enzymes include pepsin, bromelain, cathepsins, chymotrypsin, elastase, papain, plasmin, subtilisin, thrombin, trypsin, matrix metalloproteinases (e.g., stromelysin, elastase), glycosaminoglycan-specific enzymes (e.g., chondroitinase, hyaluronidase, heparinase) and the like, or combinations thereof. The source extracellular matrix material can be treated with one or more enzymes. In illustrative embodiments, the enzyme digestion can be performed at about 2° C. to about 37° C. However, the digestion can be conducted at any temperature, for any length of time (e.g., about 5 minutes to about 96 hours), and at any enzyme concentration.

In illustrative embodiments, the ratio of the extracellular matrix material (hydrated) to total enzyme (weight/weight) ranges from about 25 to about 2500. If an enzyme is used, it should be removed (e.g., by fractionation) or inactivated after the desired incubation period for the digestion so as to not compromise stability of the components in the solubilized extracellular matrix composition. Enzymes, such as pepsin for example, can be inactivated with protease inhibitors, a shift to neutral pH, a drop in temperature below 0° C., or heat inactivation, or a combination of these methods.

In another illustrative embodiment, the source extracellular matrix material can be extracted in addition to being solubilized with hydrochloric acid. Extraction methods for extracellular matrices are known to those skilled in the art and are described in detail in U.S. Pat. No. 6,375,989, incorporated herein by reference. Illustrative extraction excipients include, for example, chaotropic agents such as urea, guanidine, sodium chloride, magnesium chloride, and non-ionic or ionic surfactants.

In one embodiment, the solubilized collagen composition comprises soluble and insoluble components, and at least a portion of the insoluble components of the solubilized collagen composition can be separated from the soluble components. For example, the insoluble components can be separated from the soluble components by centrifugation (e.g., at 12,000 rpm for 20 minutes at 4° C.). In alternative embodiments, other separation techniques known to those skilled in the art, such as filtration, can be used.

In accordance with one illustrative embodiment, the solubilized extracellular matrix composition, prepared with or without the above-described separation step, is fractionated prior to polymerization. In one illustrative aspect, the solubilized extracellular matrix composition can be fractionated by dialysis. Exemplary molecular weight cut-offs for the dialysis tubing or membrane are from about 3,500 to about 12,000 or about 3,500 to about 5,000. In one embodiment, the solubilized extracellular matrix composition is dialyzed against an acidic solution having a low ionic strength. For example, the solubilized extracellular matrix composition can be dialyzed against a hydrochloric acid solution, however any other acids can be used, including acetic acid, formic acid, citric acid, lactic acid, sulfuric acid, ethanoic acid, carbonic acid, nitric acid, or phosphoric acid. In another example, the extracellular matrix composition can be dialyzed against water as long as the pH is approximately 6 or below.

In various illustrative embodiments, the fractionation, for example by dialysis, can be performed at about 2° C. to about 37° C. for about 1 hour to about 96 hours. In another illustrative embodiment, the concentration of the acid, such as acetic acid, hydrochloric acid, formic acid, citric acid, lactic acid, sulfuric acid, ethanoic acid, carbonic acid, nitric acid, or phosphoric acid, against which the solubilized extracellular matrix composition is dialyzed, can be from about 0.001 N to about 0.1 N, from about 0.005 N to about 0.1 N, from about 0.01 N to about 0.1 N, from about 0.05 N to about 0.1 N, from about 0.001 N to about 0.05 N, about 0.001 N to about 0.01 N, or from about 0.01 N to about 0.05 N. In one illustrative embodiment, the solubilized extracellular matrix composition is dialyzed against 0.01 N HCl. However, the fractionation can be performed at any temperature, for any length of time, and against any concentration of acid.

In accordance with one embodiment the 3D matrix used for culturing stem cells comprises a lyophilized, solubilized collagen composition that is rehydrated prior to contact with the cells. As discussed above, the term "lyophilized" means that water is removed from the composition, typically by freeze-drying under a vacuum (typically to dryness). In one illustrative aspect, a solubilized extracellular matrix composition is lyophilized after solubilization. In another illustrative aspect, the solubilized extracellular matrix composition is lyophilized after the solubilized portions have been separated from the insoluble portions. In yet another illustrative aspect, the solubilized extracellular matrix composition is lyophilized after a fractionation step but prior to polymerization. In another illustrative embodiment, the polymerized matrix is lyophilized. In one illustrative lyophilization embodiment, the solubilized extracellular matrix composition is first frozen, and then placed under a vacuum. In another lyophilization embodiment, the solubilized extracellular matrix composition is freeze-dried under a vacuum. Any method of lyophilization known to the skilled artisan can be used.

In accordance with one embodiment, the solubilized collagen composition is sterilized before polymerization. In one embodiment the source of the solubilized collagen (e.g., a naturally occurring extracellular matrix, or a lyophilized purified collagen composition) is sterilized prior to the solubilization step. Sterilization of the extracellular matrix material can be performed, for example, as described in U.S. Pat. Nos. 4,902,508 and 6,206,931, incorporated herein by reference. In another embodiment, the solubilized collagen composition is directly sterilized, for example, with peracetic acid. In one embodiment wherein an extracellular matrix is solubilized with an acid and the resulting material is fractionated to isolate a fraction comprising solubilized collagen, sterilization can be carried out either before or after the fractionation step. In another illustrative embodiment, the lyophilized composition itself is sterilized before rehydration, for example using an e-beam sterilization technique. In yet another illustrative embodiment, the polymerized matrix formed from the components of the solubilized collagen matrix composition is sterilized.

In one illustrative embodiment, the solubilized extracellular matrix composition is directly sterilized before the fractionation/separation step, for example, with peracetic acid or with peracetic acid and ethanol (e.g., by the addition of 0.18% peracetic acid and 4.8% ethanol to the solubilized extracellular matrix composition before the separation step). In another embodiment, sterilization can be carried out during the fractionation step. For example, the solubilized extracellular matrix composition can be dialyzed against chloroform, peracetic acid, or a solution of peracetic acid and ethanol to disinfect or sterilize the solubilized extracellular matrix composition. For example, the solubilized extracellular matrix composition can be sterilized by dialysis against a solution of peracetic acid and ethanol (e.g., 0.18% peracetic acid and 4.8% ethanol). The chloroform, peracetic acid, or peracetic acid/ethanol can be removed prior to polymerization of the solubilized collagen composition, for example by dialysis against an acid, such as 0.01 N HCl.

If the solubilized collagen composition is lyophilized, the lyophilized collagen matrix composition can be stored frozen or at room temperature (for example, at about −80° C. to about 25° C.). Storage temperatures are selected to stabilize the components of the solubilized collagen matrix composition. The compositions can be stored for about 1-26 weeks, or longer. In one illustrative embodiment, the storage solvent is hydrochloric acid. As described herein, "storage solvent" means the solvent that the solubilized collagen matrix composition is in prior to and during lyophilization. For example, hydrochloric acid, or other acids, at concentrations of from about 0.001 N to about 0.1 N, from about 0.005 N to about 0.1 N, from about 0.01 N to about 0.1 N, from about 0.05 N to about 0.1 N, from about 0.001 N to about 0.05 N, from about 0.001 N to about 0.01 N, or from about 0.01 N to about 0.05 N can be used as the storage solvent for the lyophilized, solubilized collagen matrix composition. Other acids can be used as the storage solvent including acetic acid, formic acid, citric acid, lactic acid, sulfuric acid, ethanoic acid, carbonic acid, nitric acid, or phosphoric acid, and these acids can be used at any of the above-described concentrations. In one illustrative embodiment, the lyophilizate can be stored (i.e., lyophilized in) an acid, such as acetic acid, at a concentration of from about 0.001 M to about 0.5 M or from about 0.01 M to about 0.5 M. In another embodiment, the lyophilizate can be stored in water with a pH of about 6 or below. In other illustrative embodiments, lyoprotectants, cryoprotectants, lyophilization accelerators, or crystallizing excipients (e.g., ethanol, isopropanol, mannitol, trehalose, maltose, sucrose, tert-butanol, and Tween 20), or combinations thereof, and the like can be present during lyophilization.

In one embodiment, the sterilized, solubilized collagen composition can be dialyzed against 0.01 N HCl, for example, prior to lyophilization to remove the sterilization solution and so that the solubilized extracellular matrix composition is in a 0.01 N HCl solution as a storage solvent. Alternatively, the solubilized extracellular matrix composition can be dialyzed against acetic acid as the storage solvent, for example, prior to lyophilization and can be lyophilized in acetic acid and redissolved in HCl or water.

If the solubilized extracellular matrix composition is lyophilized, the resulting lyophilizate can be redissolved in any solution, but may be redissolved in an acidic solution or water. The lyophilizate can be redissolved in, for example, acetic acid, hydrochloric acid, formic acid, citric acid, lactic acid, sulfuric acid, ethanoic acid, carbonic acid, nitric acid, or phosphoric acid, at any of the above-described concentrations, or can be redissolved in water. In one illustrative embodiment the lyophilizate is redissolved in 0.01 N HCl. For use in producing engineered matrices that can be injected in vivo or used for other purposes in vitro, the redissolved lyophilizate can be subjected to varying conditions (e.g., pH, phosphate concentration, temperature, buffer composition, ionic strength, and composition and concentration of solubilized extracellular matrix composition components (dry weight/ml)) that result in polymerization to form engineered extracellular matrices for specific tissue graft applications.

Accordingly, in one illustrative embodiment of the method described herein, a solubilized collagen composition is prepared by enzymatically treating the source extracellular matrix material with 0.1% (w/v) pepsin in 0.01 N HCl to initially solubilized the extracellular matrix material, centrifuging the enzymatically treated composition at 12,000 rpm for 20 minutes at 4° C. to remove insoluble components, fractionating the soluble fraction by dialysis against a 0.01 N HCl solution, and then polymerizing the dialyzed fraction.

In another illustrative embodiment, the method does not involve a fractionation step. In this embodiment, the source extracellular matrix material is enzymatically treated with 0.1% (w/v) pepsin in a 0.01 N hydrochloric acid solution to produce a solubilized collagen composition, the solubilized composition is then centrifuged to remove insoluble components, and then the solubilized fraction is polymerized.

In another illustrative embodiment, a solubilized collagen composition is prepared by grinding source vertebrate submucosa into a powder and enzymatically digesting the powderized submucosa with 0.1% w/v pepsin and solubilizing in 0.01 N HCl for one to three days at 4° C. Following digestion and solubilization, the solubilized components of the solubilized submucosa composition are separated from the insoluble components by centrifugation at 12,000 rpm at 4° C. for 20 minutes. The supernatant, comprising the soluble components, is recovered and the pellet containing insoluble components is discarded. The supernatant is then fractionated by dialyzing the solubilized submucosa composition against 0.01 N HCl. In one embodiment, the solubilized submucosa composition is dialyzed against several changes of 0.01 N hydrochloric acid at 4° C. using dialysis membranes having a molecular weight cut-off of 3500. Thus, the solubilized submucosa composition is fractionated to remove components having a molecular weight of less than about 3500. Alternatively, dialysis tubing or membranes having a different molecular weight cut-off can be used. The fractionated solubilized submucosa composition is then polymerized to produce the collagen based matrices of the present invention.

In accordance with another illustrative embodiment, a solubilized collagen composition is prepared by grinding vertebrate submucosa into a powder and digesting the powderized submucosa composition with 0.1% w/v pepsin and solubilizing in 0.01 N hydrochloric acid for one to three days at 4° C. The solubilized components are then separated from the insoluble components, for example, by centrifugation at 12,000 rpm at 4° C. for 20 minutes. The supernatant, comprising the soluble components, is recovered and the pellet containing insoluble components is discarded. The non-fractionated solubilized submucosa composition is then polymerized.

The present invention encompasses the formation of a solubilized collagen composition from a complex extracellular matrix material without purification of the matrix components. However, the components of the naturally occurring extracellular matrices can be partially purified and the partially purified composition can be used in accordance with the methods described herein to prepare a solubilized collagen composition. Purification methods for extracellular matrix components are known to those skilled in the art and are described in detail in U.S. Pat. No. 6,375,989, incorporated herein by reference. In accordance with one embodiment the solubilized collagen composition includes purified type I collagen or type I and type III collagen as the only protein constituents of the composition.

The solubilized collagen composition can be polymerized under different conditions to produce a collagen based matrix having the desired microstructures and mechanical properties. Polymerization of purified type I collagen solutions at different concentrations of collagen affected fibril density while maintaining a relatively constant fibril diameter. In addition, both fibril length and diameter are affected by altering the pH of the polymerization reaction.

Additional conditions can be varied during the polymerization reaction to provide engineered purified collagen matrices that have the desired properties. In illustrative embodiments, the conditions that can be varied include pH, phosphate concentration, temperature, buffer composition, ionic strength, the extracellular matrix components in the solubilized extracellular matrix composition, and the concentration of solubilized extracellular matrix composition components (dry weight/ml). These conditions result in polymerization of the extracellular matrix components to form engineered extracellular matrices with desired compositional, microstructural, and mechanical characteristics. Illustratively, these compositional, microstructural, and mechanical characteristics can include fibril length, fibril diameter, number of fibril-fibril connections, fibril density, fibril organization, matrix composition, 3-dimensional shape or form, viscoelastic, tensile, or compressive behavior, shear (e.g., failure stress, failure strain, and modulus), permeability, swelling, hydration properties (e.g., rate and swelling), and in vivo tissue remodeling and bulking properties, and desired in vitro cell responses. The matrices described herein have desirable biocompatibility, vascularization, remodeling, and bulking properties, among other desirable properties.

In various illustrative embodiments, qualitative and quantitative microstructural characteristics of the engineered matrices can be determined by environmental or cryostage scanning electron microscopy, transmission electron microscopy, confocal microscopy, second harmonic generation multi-photon microscopy. In another embodiment, polymerization kinetics may be determined by spectrophotometry or time-lapse confocal reflection microscopy. In another embodiment, tensile, compressive and viscoelastic properties can be determined by rheometry or uniaxial tensile testing. In another embodiment, a rat subcutaneous injection model can be used to determine remodeling and bulking properties. All of these methods are known in the art or are further described in Examples 5-7 or are described in Roeder et al., *J. Biomech. Eng.* vol. 124, pp. 214-222 (2002) and in Pizzo et al., *J. Appl. Physiol.*, vol. 98, pp. 1-13 (2004), incorporated herein by reference.

In accordance with one embodiment, the solubilized collagen composition is polymerized at a final total collagen concentration of about 1 to about 40 mg/ml, and in one embodiment about 1 to about 30 mg/ml, in another embodiment about 2 to about 25 mg/ml and in another embodiment about 5 to about 15 mg/ml. In one embodiment the final total collagen is selected from a range of about 0.25 to about 5.0 mg/ml, or in another embodiment the final total collagen concentration is selected from the range of about 0.5 to about 4.0 mg/ml, and in another embodiment the final total collagen concentration is selected from the range of about 1.0 to about 3.0 mg/ml, and in another embodiment the final total collagen concentration is about 0.3, 0.5, 1.0, 2.0 or 3.0 mg/ml. In other embodiments, the components of the solubilized extracellular matrix composition are polymerized at final concentrations (dry weight/ml) of about 0.25 to about 10 mg/ml, about 0.25 to about 20 mg/ml, about 0.25 to about 30 mg/ml, about 0.25 to about 40 mg/ml, about 0.25 to about 50 mg/ml, about 0.25 to about 60 mg/ml, or about 0.25 to about 80 mg/ml.

In various illustrative embodiments, the total collagen comprising the solubilized collagen composition comprises type I and type III collagen, wherein the percent range of the type III collagen and type I collagen is selected from about 17-33% and about 66-83%, respectively, to achieve various collagen type I/III ratios. Examples of percentage ranges of type III collagen and type I collagen, respectively that may be used in the matrices include 17% and 83%; 20% and 80%; 25% and 75%; 30% and 70%; and 33% and 66%, respectively. In various illustrative embodiments, the type I collagen to type III collagen ratio may be in the range of about 6:1 to about 1:1. Examples of the type I collagen to type III collagen ratios that may be used in the matrices include 6:1, 5:1, 4:1, 3:1, 2:1, 1.5:1, and 1:1.

In various illustrative embodiments, at least 3 ug/ml of type I collagen is combined with at least 0.5 ug/ml of type III collagen to obtain a total amount of collagen. Examples of the amount of type I collagen combined with type III collagen, respectively, that may be used in the matrices include 3 ug/ml and 0.5 ug/ml; 1500 ug/ml and 250 ug/ml; 1500 ug/ml and 500 ug/ml; 1500 ug/ml and 750 ug/ml; and 1500 ug/ml and 1500 ug/ml.

In various illustrative embodiments, the conditions for combining type I collagen and type III collagen can be the same as those described above for the method of decreasing stiffness of an extracellular matrix composition.

Illustratively, the matrix compositions produced by the methods described herein can be combined, prior to, during, or after polymerization, with stem cells or progenitor cells, to further enhance the repair or replacement of diseased or damaged tissues. Examples of progenitor cells include those that give rise to blood cells, fibroblasts, endothelial cells, epithelial cells, smooth muscle cells, skeletal muscle cells, cardiac muscle cells, multi-potential progenitor cells, pericytes, and osteogenic cells. The population of progenitor cells can be selected based on the cell type of the intended tissue to be repaired. For example, if skin is to be repaired, the population of progenitor cells will give rise to non-keratinized epithelial cells or if cardiac tissue is to be repaired, the progenitor cells can produce cardiac muscle cells. The matrix composition can also be seeded with autogenous cells isolated from the patient to be treated. In an alternative embodiment the cells may be xenogeneic or allogeneic in nature.

In any of the embodiments described above using purified collagen, the purified collagen can be sterilized after purification. In yet other embodiments, the collagen that is purified can be sterilized before or during the purification process. In other embodiments, purified collagen can be sterilized before polymerization or the matrix can be sterilized after polymerization.

It has been reported that the use of progenitor or stem cells to treat damaged tissues (including for example treating myocardial infarction followed by heart failure) has demonstrated early evidence of potential utility. However, recent data, has revealed three key issues that significantly limit successful delivery of reparative cells to tissues. These are 1.) inefficient and inconsistent local retention of cells acutely following injection into tissues [Hou et al., 2005, Circulation, 112: 1150-6]; 2.) limited survival of cells over time following injection into tissues [Rehman et al., 2004, Circulation 109: 1292-8]; and 3.) lack of a suitable cellular microenvironment to modulate differentiation into the desired tissue types (e.g., either vascular structures or myocytes in the context of tissue remodeling in response to ischemic insult) [Reinlib and Field, 2000, Circulation101: E182-E187].

In accordance with one embodiment a novel cell delivery strategy is provided that involves the suspension of cells in a liquid-phase, injectable solubilized collagen composition that polymerizes in situ to form a three-dimensional (3D) matrix. The 3D matrix is designed to both entrap cells and provide them with an "instructive" microenvironment which promotes cell survival and modulates their fate. It is anticipated that the introduction of cells in the presence of a comparatively viscous medium (i.e., the solubilized collagen composition, which will subsequently assemble in situ shortly after post-injection) will enhance the cells local retention. Furthermore, as noted in Examples 12-15, the components of the 3D matrix and their microstructural organization play an important role in determining cell fate with respect to survival, proliferation, and differentiation. Interestingly, recent data shows that a nanofiber microenvironment formed intramyocardially following injection of a peptide (8-16 amino acids long) hydrogel (of which the biological signaling capacity and degradation properties have yet to be elucidated) resulted in formation of a nanofiber microenvironment that promoted endogenous cell recruitment [Davis et al., 2005 Circulation 111:442-50]. Furthermore, co-culture of endothelial cells with cardiomyocytes within the peptide hydrogel in vitro dramatically decreased apoptosis and necrosis of cardiomyocytes [Narmaneva et al., 2004 Circulation 110: 962-968].

As reported herein, the biophysical signals provided by a 3D self-assembled collagen microenvironment can be used to direct the proliferation and differentiation capacity of multi-potential, bone marrow-derived stem cells. For example, 3D purified collagen matrices characterized by a relatively high fibril density and stiffness supported an increase in clonal growth and enhanced osteogenesis (bone formation). Collectively, these results demonstrate the ability to engineer injectable, self-assembling 3D purified collagen matrices in which the composition, microstructure, and mechanical properties are defined and systematically varied with discrete outcomes. In general, the biophysical features of the 3D matrix, in addition to cellular signaling modalities consisting of soluble factors and cell-cell interactions, are determinants of cell fate and represent a new target for therapeutic manipulation.

In accordance with one embodiment a method of enhancing the repair of damaged, diseased or congenital defective tissues is provided. The method comprises the steps of suspending a population of cells within a solubilized collagen composition, inducing the polymerization of the solubilized collagen composition, and injecting the composition into warm blooded species. Typically, the composition is injected into a mammalian species, including a human for example, and in one embodiment the cells represent autologous. In an alternative embodiment the cells may be xenogeneic or allogeneic cells. The injected solubilized collagen composition polymerizes in vivo to form a 3D matrix with the population of cells embedded within the collagen matrix. In one embodiment the population of cells comprise stem cells. In one embodiment the soluble collagen composition comprises purified type I collagen, glucose, and calcium chloride. In one embodiment a 3D purified collagen matrix is provided comprising collagen fibrils at a fibril area fraction of about 12% to about 25% (area of fibril to total area) that comprises glucose and $CaCl_2$. In one embodiment the solubilized collagen composition comprises about 0.05 mg/ml to about 5 mg/ml total purified collagen (either type I alone or a combination of type I and type III collagen) about 1.11 mM to about 277.5 mM glucose and about 0.2 mM to about 4.0 mM $CaCl_2$. Applicants have discovered that the inclusion of glucose and $CaCl_2$ within the interstitial fluid of the 3D matrices enhances the survival and functioning of cells seeded within the 3D matrix.

In one embodiment the solubilized collagen composition comprises about 0.1 mg/ml to about 3 mg/ml total purified collagen (either type I alone or a combination of type I and type III collagen) in about 0.05 to about 0.005N HCl (and in one embodiment about 0.01N HCl), about 0.07M to about 0.28M NaCl (and in one embodiment about 0.137M NaCl), about 1.3 to about 4.5 mM KCl (and in one embodiment about 2.7 mM KCl), about 4.0 to about 16 mM $Na_2HPO_4$ (and in one embodiment about 8.1 mM $Na_2HPO_4$), about 0.7 to about 3.0 mM $KH_2PO_4$ (and in one embodiment about 1.5 mM $KH_2PO_4$), about 0.25 to about 1.0 mM $MgCl_2$ (and in one embodiment about 0.5 mM $MgCl_2$), about 2.8 mM to about 166 mM glucose, (and in one embodiment about 5 mM glucose). Polymerization of the solubilized collagen composition is induced by the addition of a neutralizing solution such as NaOH. For example a NaOH solution can be added to a final concentration of 0.01N NaOH. The cells are then added to the composition after the addition of neutralizing solution. In accordance with one embodiment a calcium chloride solution is also added to the solubilized collagen composition. In this embodiment, calcium chloride is added to bring the final concentration of $CaCl_2$ in the solubilized collagen composition to about 0.4 mM to about 2.0 mM $CaCl_2$ (and in one embodiment about 0.9 mM $CaCl_2$). The composition is then allowed to polymerize either in vitro or in vivo to form a 3D matrix comprised of collagen fibrils wherein the cells are embedded within the 3D matrix. In illustrative embodiments the polymerization reaction is conducted in a buffered solution using any biologically compatible buffer system known to those skilled in the art. For example the buffer may be selected from the group consisting of phosphate buffer saline (PBS), Tris (hydroxymethyl) aminomethane Hydrochloride (Tris-HCl), 3-(N-Morpholino) Propanesulfonic Acid (MOPS), piperazine-n,n'-bis(2-ethanesulfonic acid) (PIPES), [n-(2-Acetamido)]-2-Aminoethanesulfonic Acid (ACES), N-[2-hydroxyethyl]piperazine-N'-[2-ethanesulfonic acid] (HEPES) and 1,3-bis[tris(Hydroxymethyl)methylamino]propane (Bis Tris Propane). In one embodiment the buffer is PBS, Tris or MOPS and in one embodiment the buffer system is PBS, and more particularly 10×PBS. In accordance with one embodiment the 10×PBS buffer at pH 7.4 comprises the following ingredients:

1.37M NaCl
0.027M KCl
0.081M $Na_2HPO_4$
0.015M $KH_2PO_4$
5 mM $MgCl_2$
55.5 mM glucose To create 10×PBS buffers of different pH, the ratio of $Na_2HPO_4$ and $KH_2PO_4$ is varied. Ionic strength may be adjusted as an independent variable by varying the molarity of NaCl only.

The polymerization of the solubilized collagen composition is conducted at a pH selected from the range of about 6.0 to about 9.0, and in one embodiment polymerization is conducted at a pH selected from the range of about 5.0 to about 11.0 and in one embodiment about 6.0 to about 9.0, and in one embodiment polymerization is conducted at a pH selected from the range of about 6.5 to about 8.5, in another embodiment polymerization of the solubilized collagen composition is conducted at a pH selected from the range of about 7.0 to about 8.0, and in another embodiment polymerization of the solubilized collagen composition is conducted at a pH selected from the range of about 7.3 to about 7.4.

The ionic strength of the buffered solution is also regulated. In accordance with one embodiment the ionic strength of the solubilized collagen composition is selected from a range of about 0.05 to about 1.5 M, in another embodiment the ionic strength is selected from a range of about 0.10 to about 0.90 M, in another embodiment the ionic strength is selected from a range of about 0.14 to about 0.30 M and in another embodiment the ionic strength is selected from a range of about 0.14 to about 0.17 M.

In still other illustrative embodiments, the polymerization is conducted at temperatures selected from the range of about 0° C. to about 60° C. In other embodiments, polymerization is conducted at temperatures above 20° C., and typically the polymerization is conducted at a temperature selected from the range of about 20° C. to about 40° C., and more typically the temperature is selected from the range of about 30° C. to about 40° C. In one embodiment the polymerization is conducted at about 37° C.

In yet other embodiments, the phosphate concentration is varied. For example, in one embodiment, the phosphate concentration is selected from a range of about 0.005 M to about 0.5 M. In another illustrative embodiment, the phosphate concentration is selected from a range of about 0.01 M to about 0.2 M. In another embodiment, the phosphate concentration is selected from a range of about 0.01 M to about 0.1 M. In another illustrative embodiment, the phosphate concentration is selected from a range of about 0.01 M to about 0.03 M. In other illustrative embodiments, the solubilized collagen composition can be polymerized by, for example, dialysis against a solution under any of the above-described conditions (e.g., dialysis against PBS at pH 7.4), extrusion or coextrusion of submucosa formulations into a desired buffer, including the buffers described above, or wet-spinning to form strands of extracellular matrix material. In one embodiment the strands can be formed by extrusion of a solubilized collagen composition through a needle and can be air-dried to form threads.

In one embodiment the strands can be formed by extrusion through a needle and can be air-dried to form fibers or threads of various dimensions. The syringe can be adapted with needles or tubing to control the dimensions (e.g., diameter) of the fibers or threads. In one embodiment, the extrusion process involves polymerization of the solubilized extracellular matrix composition followed by extrusion into a bath containing water, a buffer, or an organic solvent (e.g., ethanol). In another embodiment, the extrusion process involves coextrusion of the solubilized extracellular matrix composition with a polymerization buffer (e.g., the buffer such as Tris or phosphate buffers at various concentrations can be varied to control pH and ionic strength). In yet another embodiment, the extrusion process involves extrusion of the solubilized extracellular matrix composition into a polymerization bath (e.g., the buffer such as Tris or phosphate buffers at various concentrations can be varied to control pH and ionic strength). The bath conditions affect polymerization time and properties of the fibers or threads, such as mechanical integrity of the fibers or threads, fiber dimensions, and the like. In one embodiment the extrusion of a solubilized collagen composition through a needle is used a method to control orientation of polymerized fibrils within the fibers. In one embodiment, the fibers can be air-dried to create materials that can be crosslinked or woven into three dimensional meshes or mats that can serve as a substrate, or a component of a substrate, for culturing cells. In various illustrative embodiments, engineered extracellular matrices can be polymerized from the solubilized extracellular matrix composition at any step in the above-described methods. For example, the engineered matrices can be polymerized from the solubilized extracellular matrix composition after the solubilization step or after the separation step, the filtration step, or the lyophilization and rehydration steps, if the separation step, the filtration step, and/or the lyophilization and rehydration steps are performed.

The engineered matrices can be combined, prior to, during, or after polymerization, with nutrients, including minerals, amino acids, pharmaceutical agents, sugars, peptides, proteins, vitamins (such as ascorbic acid), or glycoproteins that facilitate cellular proliferation, such as laminin and fibronectin, or growth factors such as epidermal growth factor, platelet-derived growth factor, transforming growth factor beta, or fibroblast growth factor, and glucocorticoids such as dexamethasone. In other illustrative embodiments, fibrillogenesis modulators, such as alcohols, glycerol, glucose, or polyhydroxylated compounds can be added prior to or during polymerization. In accordance with one embodiment, cells can be added to the solubilized extracellular matrix composition as the last step prior to the polymerization or after polymerization of the matrix. In another illustrative embodiment, particulate extracellular matrix compositions can be added to the solubilized extracellular matrix composition and can enhance in vivo bulking capacity. In other illustrative embodiments, cross-linking agents, such as carbodiimides, aldehydes, lysloxidase, N-hydroxysuccinimide esters, imidoesters, hydrazides, and maleimides, and the like can be added before, during, or after polymerization.

Hyaluronic acid (HA) is a glycosaminoglycan found naturally within the extracellular matrix. This mucopolysaccharide is made up of a repetitive sequence of two modified simple sugars, glucuronic acid and N-acetyl glucosamine. HA molecules are negatively charged and typically high in molecular weight (long in size). The size and charged nature of this molecule allow it to bind water to produce a high viscosity gel. When hyaluronic acid is added to soluble collagen compositions and the solubilized collagen compositions are allowed to polymerize, it appears that only subtle changes occur to the fibrillar microstructure of the resultant 3D matrix. On the other hand, increasing the hyaluronic acid content significantly affects the viscous fluid phase of the extracellular matrix, providing it with distinct mechanical behavior. Furthermore, the addition of hyaluronic acid to engineered matrices was found to modulate the manner by which cells remodel and contract the matrix. Accordingly, HA content represents a further variable of the present engineered 3D matrices that can be manipulated to provide an optimal microenvironment for cells cultured within the matrices.

In accordance with one embodiment the engineered purified collagen based matrices of the present invention can be used as cell culture substrates that more accurately mimic the substrates that various cells contact in vivo. Accordingly, collagenous based matrices can be designed for specific cell types to mimic their native environment. In this manner stem cells or progenitor cells can be cultured in vitro without altering the fundamental cell behavior (e.g., cell proliferation, growth, maturation, differentiation, migration, adhesion, gene expression, apoptosis and other cell behaviors) of the cells. In another embodiment, the engineered purified collagen based matrices of the present invention can be used to expand or differentiate a cell population, such a stem cell population (including pluripotent or unipotent cells), primary cells, progenitor cells or other eukaryotic cells by seeding the cells on, or within, the collagen based matrix and culturing the cells in vitro for a predetermined length of time under conditions conducive for that cell type's proliferation (i.e., appropriate nutrients, temperature, pH, etc.). In accordance with one embodiment cells are added to the solubilized collagen composition as the last step prior to the polymerization of the solubilized collagen composition. The engineered purified collagen based matrices of the present invention can be combined with nutrients, including minerals, pharmaceutical agents, amino acids, sugars, peptides, proteins, vitamins (such as ascorbic acid), or glycoproteins that facilitate cellular proliferation, such as laminin and fibronectin and growth factors such as epidermal growth factor, platelet-derived growth factor, transforming growth factor beta, or fibroblast growth factor, and glucocorticoids such as dexamethasone.

In one example of an embodiment comprising a collagen based matrix seeded with living cells, a sterilized engineered purified collagen based matrix may be seeded with living cells and packaged in an appropriate medium for the cell type used. For example, a cell culture medium comprising Dulbecco's Modified Eagles Medium (DMEM) can be used with standard additives such as non-essential amino acids, glucose, ascorbic acid, sodium pyruvate, fungicides, antibiotics, etc., in concentrations deemed appropriate for cell type, shipping conditions, etc.

The cell seeded engineered purified collagen based matrices of the present invention can be used simply for culturing cells in vitro, or the composition can be implanted or injected as a tissue graft construct to enhance the repair of damaged or diseased tissue. In one embodiment an improved tissue graft construct is provided wherein the construct comprises a 3D purified collagen based matrix and a population of cells. The 3D purified collagen based matrix is formed from a solubilized collagen composition wherein the solubilized composition is formed by contacting a source of purified collagen with an acid selected from the group consisting of hydrochloric acid, acetic acid, formic acid, sulfuric acid, ethanoic acid, carbonic acid, nitric acid, or phosphoric acid. The solubilized collagen composition is then polymerized as described above to form the 3D purified collagen based matrix.

Cells, and in one embodiment stem cells, are combined with the collagen based matrix at a low density and can be either added to the solubilized collagen composition prior to polymerization, or after formation of the collagen based matrix. This initial seeded population of cells can be expanded by incubating the composition under conditions suitable for replication of the seeded cells. Accordingly, cell seeded 3D purified collagen based matrices of the present invention comprise a population of cells that consists of, or are the progeny of, eukaryotic stem cells initially added to the composition at a low density. In one embodiment a tissue graft construct is prepared comprising the 3D purified collagen based matrices of the present invention that have been seeded with a low density of cells, wherein the cells are cultured within the matrix to expand and/or differentiate the seeded population of cells prior to implantation of the graft construct in a host. In one embodiment the cells, and more particularly stem cells, are initially seeded within the 3D purified collagen matrix at a final concentration of about 10 to about $10^8$ cells per milliliter, and in one embodiment at a final concentration of less than $10^5$ cells per milliliter.

For most cells, cell survival during in vitro culture is known to decrease as the concentration/density at which the cells are initially seeded onto a substrate. Applicants have discovered that using an engineered purified collagen based matrix and seeding stem cells at very low densities, clonal populations of stem cells can be isolated in a substantially pure form. Typically the isolation of non-embryonic stem cells results in the isolation of cells that may differentiate along different cell lineage pathways. In accordance with one embodiment of the present invention culturing conditions can be selected wherein a decreased seeding density of viable pluripotent or multipotent stem cells within an engineered purified collagen based matrix leads to clonal growth of cells representing a single cell lineage. Such cells can be isolated and transferred to a second engineered purified collagen based matrix and conditions can be altered to enhance the proliferation of the isolated clonal population of cells. Estimates of optimal cell densities for clonal growth range from about 10 cells/ml to about $10^3$ cells/ml and depend upon the specific seeding efficiencies.

In accordance with one embodiment a method of isolating clonal populations of individual stem cells is provided. The method comprises the steps of contacting a source of collagen with hydrochloric acid to prepare a solubilized collagen composition. The solubilized collagen composition is then polymerized to form an engineered purified collagen based matrix. The stem cells are seeded on or within the engineered purified collagen based matrix at a low density that maintains the functionality of the stem cells but allows for the isolation of clonal populations of cells. In accordance with one embodiment the solubilized collagen composition is prepared having a type I collagen concentration selected from the range of about 1.0 to 3.0 mg/ml, and a pH of about 6.5 to about 7.0, wherein the solubilized collagen composition further comprises glucose and calcium chloride. In one embodiment stem cells are seeded at a concentration selected from the range of from about 10 to about $10^3$ cells per milliliter. In one embodiment the source of collagen used to prepare the solubilized collagen composition comprises a purified preparation of type I collagen that has been dissolved in a hydrochloric acid solution. In an alternative embodiment the source of collagen comprises a hydrochloric acid solubilized fraction of a naturally occurring extracellular matrix, such as a submucosal matrix. In one embodiment the solubilized collagen composition is prepared from vertebrate intestinal submucosa. The hydrochloric acid solution used to prepared the solubilized collagen composition can be from about 0.005 N to about 0.1 N, from about 0.01 N to about 0.1 N, from about 0.05 N to about 0.1 N, from about 0.001 N to about 0.05 N, about 0.001 N to about 0.01 N, or from about 0.01 N to about 0.05 N HCl.

In any of the embodiments described in this application, the solubilized collagen composition (i.e., purified collagen or extracellular matrix components) can be polymerized at final concentrations of collagen (dry weight/ml) of about 5 to about 10 mg/ml, about 5 to about 30 mg/ml, about 5 to about 50 mg/ml, about 5 to about 100 mg/ml, about 20 to about 50 mg/ml, about 20 to about 60 mg/ml, or about 20 to about 100 mg/ml. Illustratively, the three-dimensional matrices may contain fibrils with specific characteristics, including, but not limited to, a fibril area fraction (defined as the percent area of the total area occupied by fibrils in a cross-sectional surface of the matrix; i.e., fibril density) of about 7% to about 26%, about 20% to about 30%, about 20% to about 50%, about 20% to about 70%, about 20% to about 100%, about 30% to about 50%, about 30% to about 70%, or about 30% to about 100%. In further illustrative embodiments, the three-dimensional matrices have an elastic or linear modulus (defined by the slope of the linear region of the stress-strain curve obtained using conventional mechanical testing protocols; i.e., stiffness) of about 0.5 kPa to about 40 kPa, about 30 kPa to 100 kPa, about 30 kPa to about 1000 kPa, about 30 kPa to about 10000 kPa, about 30 kPa to about 70000 kPa, about 100 kPa to 1000 kPa, about 100 kPa to about 10000 kPa, or about 100 kPa to about 70000 kPa.

In accordance with one embodiment a kit is provided for preparing 3D matrices that have been optimized for a particular cell that is to be seeded within the formed 3D matrix. The kit is provided with purified individual components that can be combined to form a solubilized collagen composition that upon polymerization forms a 3D matrix comprised of collagen fibrils that presents an optimal microenvironment for a population of cells. Typically the population of cells represent cells provided separately from the kit, but in one embodiment the cells may also constitute a component of the kit. In one embodiment the cells are mammalian cells, including human cells, and in a further embodiment the cells are stem or progenitor cells. In accordance with one embodiment a kit is provided comprising a solubilized collagen composition and a polymerization composition. In a further embodiment the solubilized collagen composition comprises purified type I collagen as the sole collagen component. In another embodiment the solubilized collagen composition comprises purified type I collagen and type III collagen as the sole collagen components.

In one embodiment the kit comprises separate vessels, each containing one of the following components: purified type I collagen, a phosphate buffer solution, a glucose solution, a calcium chloride solution and a basic neutralizing solution. In one embodiment the purified type I collagen of the kit is provided in a lyophilized form and the kit is further provided with a solution of HCl (or other dilute acid including for example, acetic acid, formic acid, lactic acid, citric acid, sulfuric acid, ethanoic acid, carbonic acid, nitric acid, or phosphoric acid) for resuspending the lyophilized collagen. In one embodiment the kit is provided with a solution comprising a solubilized collagen composition, and in a further embodiment the solubilized collagen composition comprises a solubilized extracellular matrix composition. In one embodiment the kit comprises a phosphate buffer solution, a glucose solution, a calcium chloride solution, and acid solution, a basic neutralizing solution, a vessel comprising purified type I collagen, and a vessel comprising purified type III collagen. In one embodiment the polymerization composition comprises a phosphate buffer that has a pH of about 7.2 to about 7.6 and the acid solution is an HCl solution comprising about 0.05N to about 0.005N HCl, and in one embodiment the acid solution is about 0.01N HCl. In one embodiment the glucose solution has a concentration selected from the range of about 0.2% to about 5% w/v glucose, or about 0.5% to about 3% w/v glucose, and in one embodiment the glucose solution is about 1% w/v glucose. In one embodiment the $CaCl_2$ solution has a concentration selected from the range of about 2 mM to about 40.0 mM $CaCl_2$, or about 0.2 mM to about 4.0 mM $CaCl_2$, or about 0.2 to about 2 mM $CaCl_2$. In one embodiment the kit is provided with a 10×PBS buffer having a pH of about pH 7.4, and comprising about 1.37M NaCl, about 0.027M KCl, about 0.081M $Na_2HPO_4$, about 0.015M $KH_2PO_4$, about 5 mM $MgCl_2$ and about 1% w/v glucose.

The kit can further be provided with instructional materials describing methods for mixing the kit reagents to prepare 3D matrices. In particular, the instructions materials provide information regarding the final concentrations and relative proportions of the matrix components that give optimal microenvironmental conditions including fibril microstructure and mechanical properties for a particular cell type or for a particular desired result (i.e., clonal expansion of cells, differentiation, etc.).

The following examples illustrate specific embodiments in further detail. These examples are provided for illustrative purposes only and should not be construed as limiting the invention or the inventive concept in any way.

EXAMPLE 1

Preparation of Lyophilized, Bioactive ECM Compositions from Fractionated Submucosa Hydrolysates Small intestinal submucosa is harvested and prepared from freshly euthanized pigs as previously disclosed in U.S. Pat. No. 4,956,178. Intestinal submucosa is powderized under liquid nitrogen and stored at −80° C. prior to use. Digestion and solubilization of the material is performed by adding 5 grams of powdered tissue to each 100 ml of solution containing 0.1% w/v pepsin in 0.01 N hydrochloric acid and incubating for 72 hours at 4° C. Following the incubation period, the resulting solubilized composition is centrifuged at 12,000 rpm for 20 minutes at 4° C. and the insoluble pellet is discarded. The supernatant is dialyzed against at least ten changes of 0.01 N hydrochloric acid at 4° C. (MWCO 3500) over a period of at least four days. The solubilized fractionated composition is then sterilized by dialyzing against 0.18% peracetic acid/4.8% ethyl alcohol for about two hours. Dialysis of the composition is continued for at least two more hours, with additional changes of sterile 0.01 N hydrochloric acid per day, to eliminate the peracetic acid. The contents of the dialysis bags are then lyophilized to dryness and stored.

EXAMPLE 2

Preparation of Lyophilized, Bioactive ECM Compositions from Non-Fractionated Submucosa Hydrolysates Small intestinal submucosa was harvested and prepared from freshly euthanized pigs as previously disclosed in U.S. Pat. No. 4,956,178. Intestinal submucosa was powderized under liquid nitrogen and stored at −80° C. prior to use. Partial digestion of the material was performed by adding 5 g powdered tissue to each 100 ml solution containing 0.1% w/v pepsin in 0.01M hydrochloric acid and digesting for 72 hours at 4° C. Following partial digestion, the suspension was centrifuged at 12,000 rpm for 20 minutes at 4° C. and the insoluble pellet discarded. The supernatant was lyophilized to dryness.

EXAMPLE 3

Preparation of Reconstituted, Bioactive ECM Compositions

Immediately prior to use, lyophilized material from Example 2, consisting of a mixture of extracellular matrix components, was reconstituted in 0.01 N HCl. To polymerize the soluble extracellular matrix components into a 3-dimensional matrix, reconstituted extracellular matrix solutions were diluted and brought to a particular pH, ionic strength, and phosphate concentration by the addition of a phosphate buffer and concentrated HCl and NaOH solutions. Polymerization of neutralized solutions was then induced by raising the temperature from 4° C. to 37° C. Various polymerization buffers (including, e.g., phosphate buffers) were used and the pH of the polymerization reaction was controlled by varying the ratios of mono- and dibasic phosphate salts. Ionic strength was varied based on sodium chloride concentration.

Type I collagen prepared from calf skin was obtained from Sigma-Aldrich Corporation, St. Louis, Mo., and dissolved in and dialyzed extensively against 0.01 M hydrochloric acid (HCl) to achieve desired concentrations. Interstitial ECM was prepared from porcine small intestinal submucosa (SIS). SIS was powdered under liquid nitrogen and the powder stirred (5% w/v) into 0.01 N hydrochloric acid containing 0.1% (w/v) pepsin for 72 h at 4° C. The suspension was centrifuged at 12,000×g for 20 min at 4° C. to remove undissolved tissue particulate and lyophilized to dryness. Immediately prior to experimental use, the lyophilized material was redissolved in 0.01 N HCl to achieve desired collagen concentrations. To polymerize the soluble collagen or interstitial ECM components into a 3D matrix, each solution was diluted and brought to the specified pH, ionic strength, and phosphate concentration by the addition of a polymerization composition and concentrated HCl and NaOH solutions. Polymerization of neutralized solutions was induced by raising the temperature from 4° C. to 37° C. Various polymerization compositions were used to make final solutions with the properties shown in Table 2.

TABLE 2

| Collagen formulations | | | | SIS formulations | | | |
|---|---|---|---|---|---|---|---|
| pH | I | [$P_i$] | [C] | pH | I | [$P_i$] | [C] |
| Series 1 | | | | | | | |
| 6.5 | 0.16 | 0.01 | 1 mg/ml | 6.5 | 0.16 | 0.01 | 1 mg/ml |
| 7.0 | 0.16 | 0.01 | 1 mg/ml | 7.0 | 0.16 | 0.01 | 1 mg/ml |
| 7.4 | 0.17 | 0.01 | 1 mg/ml | 7.4 | 0.17 | 0.01 | 1 mg/ml |
| 8.0 | 0.17 | 0.01 | 1 mg/ml | 8.0 | 0.17 | 0.01 | 1 mg/ml |
| 8.5 | 0.17 | 0.01 | 1 mg/ml | 8.5 | 0.17 | 0.01 | 1 mg/ml |
| 9.0 | 0.17 | 0.01 | 1 mg/ml | 9.0 | 0.17 | 0.01 | 1 mg/ml |
| Series 2 | | | | | | | |
| 7.4 | 0.06 | 0.02 | 1 mg/ml | 7.4 | 0.06 | 0.02 | 1 mg/ml |
| 7.4 | 0.10 | 0.02 | 1 mg/ml | 7.4 | 0.30 | 0.02 | 1 mg/ml |
| 7.4 | 0.15 | 0.02 | 1 mg/ml | 7.4 | 0.60 | 0.02 | 1 mg/ml |
| 7.4 | 0.20 | 0.02 | 1 mg/ml | 7.4 | 0.90 | 0.02 | 1 mg/ml |
| 7.4 | 0.25 | 0.02 | 1 mg/ml | 7.4 | 1.20 | 0.02 | 1 mg/ml |
| | | | | 7.4 | 1.50 | 0.02 | 1 mg/ml |
| Series 3 | | | | | | | |
| 7.4 | 0.15 | 0.00 | 1 mg/ml | 7.4 | 0.3 | 0.00 | 1 mg/ml |
| 7.4 | 0.15 | 0.01 | 1 mg/ml | 7.4 | 0.3 | 0.02 | 1 mg/ml |
| 7.4 | 0.15 | 0.02 | 1 mg/ml | 7.4 | 0.3 | 0.04 | 1 mg/ml |
| 7.4 | 0.15 | 0.03 | 1 mg/ml | 7.4 | 0.3 | 0.06 | 1 mg/ml |
| 7.4 | 0.15 | 0.04 | 1 mg/ml | 7.4 | 0.3 | 0.08 | 1 mg/ml |
| 7.4 | 0.15 | 0.05 | 1 mg/ml | 7.4 | 0.3 | 0.11 | 1 mg/ml |

Table 2: Engineered ECMs representing purified type I collagen or a complex mixture of interstitial ECM components (SIS) were prepared at varied pH (series 1), ionic strength (series 2), and phosphate concentration (series 3).
[C] represents collagen concentration in mg/ml,
[$P_i$] represents phosphate concentration in M, and
I represents ionic strength in M.

Representative data showing the results of varying the polymerization temperature, buffer system, pH (using either a phosphate or tris buffer), ionic strength, phosphate concentration or concentration of ECM material, on stiffness (elastic modulus) of the formed 3D matrix is presented in FIGS. 1A-1G. In summary, as the polymerization temperature is increased from 4° C. up to 37° C., the polymerization rate and the stiffness of the formed 3D matrix increases. The effect of a temperature gradient profile on the microstructural composition of the 3D matrix was also investigated. Polymerizing the matrix using a temperature ramp from about 4° C. to 37° C. over 30 minutes was compared to matrices formed using a step increase in temperature to 37° C. and incubated at that temperature for 30 minutes. The data revealed that fibrils formed using a temperature ramp are longer in length and have decreased fibril density compared to matrices formed using a single step increase in temperature. As the pH of the polymerizing composition is increased, from about 7.0 up to about pH 9.2, the polymerization rate and the stiffness of the formed 3D matrix increases. Buffer selection was found to play a role in determining the mechanical properties of the 3D matrix, and more particularly tris based buffers reduced stiffness more than phosphate based buffers. Regarding ionic strength, peak stiffness coincides with maximum polymerization time at an ionic strength of about 0.3 M. As phosphate concentration is increased, stiffness decreases, however the concentration of phosphate in a 1×PBS solution does not have a substantial effect on stiffness. As collagen content is increased the stiffness of the matrix is increased.

EXAMPLE 4

Three-Dimensional Imaging of Engineered ECM's by Confocal Reflection Microscopy

Solutions of type I collagen or interstitial ECM components were polymerized in a Lab-Tek chambered coverglass and imaged using a BioRad Radiance 2100 MP Rainbow confocal/multiphoton microscope using a 60×1.4 NA oil immersion lens. Optical settings were established and optimized for matrices after polymerization was complete. Samples were illuminated with 488 nm laser light and the reflected light detected with a photomultiplier tube (PMT) using a blue reflection filter. A z step of 0.2 μm was used to optically section the samples. Because the resolution of the z axis is less than that of the x-y plane, the sampling along the z axis may be different from that of the x-y. Images were collected in the range of 10-25 μm from the upper surface of the coverglass.

EXAMPLE 5

Quantification of Fibril Properties from Three Dimensional Images

Quantification of the fibril diameter distribution within engineered extracellular matrices was conducted based upon two- and three-dimensional image sets obtained via electron and confocal microscopy techniques using methods described within Brightman et al., Biopolymers 54:222-234, 2000. More recently, a Matlab program with a graphical user interface was written for measurement of fibril diameters from these images. For three-dimensional confocal images, depth attenuation was corrected by normalizing against a fitted logarithmic curve, after which images were binarized into white and black pixels using a threshold value. Three rectangles were outlined in the x-y plane across each fibril, with one axis aligned with the fibril. Average fibril diameter in each rectangle was calculated as the total white area divided by the rectangle's length. The average diameter of each fibril was taken to be the average of the three measurements, and the average diameter in a given matrix was calculated as an average of all measurements.

Length of fibril per volume was estimated by dividing the total white volume of an image by the average cross-sectional area of fibrils in that image. Due to distortion in the z-plane, the fibril cross-sections in the image could not be assumed circular and calculated from diameter. Rather, the average cross-sectional area was found by expanding the rectangles described above into three-dimensional boxes. The cross-sectional area of a fibril in was found by dividing the total white volume contained in the box by the length of the box's axis aligned with the fibril.

A Matlab program has also been developed to determine fibril density from two- and three-dimensional images. This method involves thresholding and binarizing the image data to discriminate fibrils from the background. The surface area or volume representing fibrils is then quantified and normalized to the surface area or volume of the image.

EXAMPLE 6

Spectrophotometry of Extracellular Matrix Polymerization

The time-course of polymerization was monitored in a Lambda 35 UV-VIS spectrophotometer (Perkin-Elmer) equipped with a temperature-controlled, 8-position cell changer as described previously by Brightman et al., 2000.

EXAMPLE 7

Rheometric Measurements of Extracellular Matrices

Mechanical properties of the matrices were measured using a TA Instruments AR-2000 rheometer. Neutralized collagen or SIS was placed on the peltier temperature-controlled lower plate at 6° C., and the 40-mm parallel-plate geometry was lowered to a 1-mm gap. The temperature was then raised to 37° C. as oscillation measurements were made every 30 seconds at 1 Hz and 5% strain. After polymerization was complete, an oscillation frequency sweep was made at 5% strain, from 0.1 to 3 Hz. A shear creep test was then conducted with a shear stress of 1 Pa for 1000 seconds.

EXAMPLE 8

Preparation of Reconstituted Bioactive Extracellular Matrices

Small intestinal submucosa was harvested and prepared from freshly euthanized pigs as previously disclosed in U.S. Pat. No. 4,956,178. Intestinal submucosa was powderized under liquid nitrogen and stored at −80° C. prior to use. Digestion and solubilization of the material was performed by adding 5 grams of powdered tissue to each 100 ml of solution containing 0.1% pepsin in 0.01 N hydrochloric acid and incubating with stirring for 72 hours at 4° C. Following the incubation period, the solubilized composition was centrifuged at 12,000 rpm for 20 minutes at 4° C. and the insoluble pellet was discarded. The supernatant was dialyzed extensively against 0.01 N HCl at 4° C. in dialysis tubing with a 3500 MWCO (Spectrum Medical Industries). Polymerization of the solubilized extracellular matrix composition was achieved by dialysis against PBS, pH 7.4, at 4° C. for about 48 hours. The polymerized construct was then dialyzed against several changes of water at room temperature and was then lyophilized to dryness.

The polymerized construct had significant mechanical integrity and, upon rehydration, had tissue-like consistency and properties. In one assay, glycerol was added prior to polymerization by dialysis and matrices with increased mechanical integrity and increased fibril length resulted.

EXAMPLE 9

Preparation of Extracellular Matrix Threads

Small intestinal submucosa was harvested and prepared from freshly euthanized pigs as previously disclosed in U.S.

Pat. No. 4,956,178. Intestinal submucosa was powderized under liquid nitrogen and stored at −80° C. prior to use. Digestion and solubilization of the material was performed by adding 5 grams of powdered tissue to each 100 ml of solution containing 0.1% w/v pepsin in 0.01 N hydrochloric acid and incubating for 72 hours at 4° C. Following the incubation period, the solubilized composition was centrifuged at 12,000 rpm for 20 minutes at 4° C. and the insoluble pellet was discarded.

The solubilized extracellular matrix composition (at 4° C.) was placed in a syringe with a needle and was slowly injected into a PBS solution at 40° C. The solubilized extracellular matrix composition immediately formed a filament with the diameter of the needle. If a blunt-tipped needle is used, straight filaments can be formed while coiled filaments can be formed with a bevel-tipped needle. Such filaments can be used as resorbable sutures.

EXAMPLE 10

Lyophilization and Reconstitution of Solubilized Extracellular Matrix Compositions Frozen small intestinal submucosa powder that had been prepared by cryogenic milling was centrifuged at 3000×g for 15 minutes and the excess fluid was decanted. The powder (5% weight/volume) was digested and solubilized in 0.01 N HCl containing 0.1% weight/volume pepsin for approximately 72 hours at 4° C. The solubilized extracellular matrix composition was then centrifuged at 16,000×g for 30 minutes at 4° C. to remove the insoluble material. Aliquots of the solubilized extracellular matrix composition were created and hydrochloric acid (12.1 N) was added to create a range of concentrations from 0.01 to 0.5 N HCl.

Portions of the solubilized extracellular matrix composition were dialyzed (MWCO 3500) extensively against water and 0.01 M acetic acid to determine the effects of these media on the lyophilization product. Aliquots of the solubilized extracellular matrix composition in 0.01 M acetic acid were created and glacial acetic acid (17.4 M) was added to create a range of concentrations from 0.01 to 0.5 M acetic acid. The solubilized extracellular matrix compositions were frozen using a dry ice/ethanol bath and lyophilized to dryness. The lyophilized preparations were observed, weighed, and dissolved at 5 mg/ml in either 0.01 N HCl or water. The dissolution and polymerization properties were then evaluated. The results are shown in Tables 2-6.

TABLE 3

Gross appearance of solubilized extracellular matrix compositions following lyophilization at various hydrochloric acid concentrations.

| [HCl] (N) | Appearance |
|---|---|
| 0.01 | Light, fluffy, homogenous, foam-like sheet; white to off-white in color; pliable |
| 0.05 | Slightly wrinkled and contracted, some inhomogeneities in appearance noted, slight brown tint, pliable to slightly friable in consistency |
| 0.10 | Wrinkled, collapsed in appearance; inhomogeneities noted, some regional "melting" noted; significant brown tint; friable |
| 0.25 | Wrinkled, collapsed in appearance; increased inhomogeneities noted, increased areas of regional "melting" noted; significant brown tint; friable |
| 0.50 | Significant collapse and shrinkage of specimen, dark brown coloration throughout; dark brown in color; friable |

TABLE 4

Dissolution properties of solubilized extracellular matrix compositions following lyophilization at various hydrochloric acid concentrations.

| [HCl] (N) Reconstitution Medium | Reconstitution Properties | |
|---|---|---|
| | H₂O | 0.01N HCl |
| 0.01 | Completely dissolved in 20-30 minutes, pH 4 | Completely dissolved in 20-30 minutes, pH 2 |
| 0.05 | Majority dissolved in 2 hours; slight particulate noted, pH 3-4 | Majority dissolved in 40 minutes; very slight particulate noted, pH 2 |
| 0.1 | Incomplete dissolution | Incomplete dissolution |
| 0.25 | Incomplete dissolution | Incomplete dissolution |
| 0.50 | Incomplete dissolution | Incomplete dissolution |

TABLE 5

Polymerization properties of solubilized extracellular matrix compositions following lyophilization at various hydrochloric acid concentrations.

| [HCl] (N) Reconstitution Medium | Polymerization Properties | |
|---|---|---|
| | H₂O | 0.01N HCl |
| 0.01 | Polymerized within 20-30 minutes | Polymerized within 10-20 minutes |
| 0.05 | Weak polymerization noted at 45 minutes; significant lag time in polymerization | Polymerized within 20-30 minutes |
| 0.1 | *No Polymerization | *No Polymerization |
| 0.25 | *No Polymerization | *No Polymerization |
| 0.50 | *No Polymerization | *No Polymerization |

TABLE 6

Dissolution properties of solubilized extracellular matrix compositions following lyophilization at various acetic acid concentrations.

| [Acetic Acid] (M) | Reconstitution Properties | |
|---|---|---|
| | Reconstitution in H₂O | Reconstitution in 0.01N HCl |
| 0.01 | Completely dissolved in 90 minutes, pH 5 | Completely dissolved in 90 minutes, pH 1-2 |
| 0.05 | Near complete dissolution after 90 minutes; small particulate remained, pH 5 | Completely dissolved in 90 minutes, pH 1-2 |
| 0.1 | Completely dissolved in 90 minutes, pH 5 | Near complete dissolution in 90 minutes; small particulate, pH 1-2 |
| 0.25 | Completely dissolved in 90 minutes, pH 5 | Completely dissolved in 90 minutes, pH 1-2 |
| 0.50 | Near complete dissolution after 90 minutes; small particulate remained, pH 5 | Completely dissolved in 90 minutes, pH 1-2 |

TABLE 7

Polymerization properties of solubilized extracellular matrix compositions following lyophilization at various acetic acid concentrations.

| [Acetic Acid] (M) Reconstitution Medium | Polymerization Properties | |
|---|---|---|
| | H₂O | 0.01N HCl |
| 0.01 | Polymerized within 5-10 minutes | Polymerized within 5-10 minutes |
| 0.05 | Polymerized within 5-10 minutes | Polymerized within 5-10 minutes |
| 0.1 | Polymerized within 5-10 minutes | Polymerized within 5-10 minutes |
| 0.25 | Polymerized within 5-10 minutes | Polymerized within 5-10 minutes |
| 0.50 | Polymerized within 5-10 minutes | Polymerized within 5-10 minutes |

These results show that lyophilization in HCl and reconstitution of solubilized extracellular matrix compositions in 0.01 N HCl to 0.05 N HCl or in water maintains the capacity of the components of the compositions to polymerize. The results also show that lyophilization in acetic acid maintains the capacity of the components of the compositions to polymerize when the composition is polymerized in water or HCl. The solubility rate is lyophilization from 0.01 N HCl>lyophilization from 0.01 M acetic acid≥lyophilization from water.

EXAMPLE 11

Preparation of Solubilized Sis Composition

This procedure outlines a standard technique for the preparation of SIS solution.
1. Dissolution: of SIS powder in acetic acid with Pepsin
    1.1. Preparation of acetic acid with pepsin
        1.1.1. Prepare the desired volume of 0.5 M acetic acid (typically 1 L; this requires 28.7 mL of 17.4 M glacial acetic acid).
        1.1.2. Add the desired mass of pepsin to achieve a 0.1% w/v solution (typically 1 g, if 1 L of acetic acid is used).
        1.1.3. Place the jar containing acetic acid and pepsin on a stir plate and begin mixing.
    1.2. Preparation of centrifuged SIS powder
        1.2.1. Place SIS powder in 50 mL centrifuge tubes.
        1.2.2. Centrifuge SIS powder at 3000×g for 15 minutes.
        1.2.3. Open centrifuge tubes, pour off and dispose of supernate.
        1.2.4. Remove pellets from tubes. Measure out the desired mass to achieve a 5% w/v solution (typically 50 g, if 1 L of acetic acid was used). Previously prepared and frozen material may be used, and excess centrifuged material may be frozen for later use.
    1.3. Add centrifuged SIS pellet material to acetic acid/pepsin solution.
    1.4. Cover and allow it to stir for 72 hours at 4° C.
2. Centrifugation of dissolved SIS
    2.1. When removed from stirring, the SIS/pepsin solution should appear viscous and somewhat uniform. Pour SIS/pepsin solution into centrifuge jars. Balance jars as necessary.
    2.2. This mixture should be centrifuged at 16,000×g for 30 minutes at 4° C. Refer to the operators manual or SOP for instructions on using the centrifuge. If using the Beckman model J2-21, use the JIO head at a speed of 9500 rpm.
    2.3. Remove jars of SIS from centrifuge. Pour the supernate into a clean jar. Be careful not to disturb the pellet, and stop pouring if the SIS begins to appear more white and creamy (this is pellet material).
3. Dialysis of SIS in water and hydrochloric acid
    3.1. Prepare dialysis tubing as follows:
        3.1.1. Use dialysis tubing with MWCO 3500, diameter 29 1 mll. Handle dialysis tubing with gloves, and take care not to allow it to contact foreign surfaces, as it may easily be damaged.
        3.1.2. Cut dialysis tubing to the necessary length. (typically, 3 sections of about 45 cm).
        3.1.3. Wet tubing in millipore water, and leave tubing in the water until each piece is needed.
        3.1.4. Do the following with each length of tubing:
            3.1.4.1. Place a clip near one end of the tubing.
            3.1.4.2. Holding the tubing to avoid contact with foreign surfaces, use a pipette to fill the tubing with SIS solution. Each piece of tubing should receive roughly the same volume of SIS (for example, if three lengths of tubing are used, measure one third of the total volume into each).
            3.1.4.3. Place a clip on the open end of the dialysis tubing. Avoid leaving slack. The tube should be full and taut.
            3.1.4.4. Place the filled dialysis tubing in a container of 0.01 M HCL with a stir bar.
            3.1.4.5. Repeat the above steps to fill all lengths of tubing.
        3.1.5. Leave containers to stir at 4° C.
    3.2. Details regarding changing the dialysis in 0.01 M HCl are given below.
        3.2.1. The 0.01 M HCl in the dialysis containers must be changed several times. This should be done as follows:
        3.2.2. After changing the 0.01 M HCl, another change should not be done for at least two hours.
        3.2.3. Change the 0.01 M HCl at least 10 times, over a period of at least four days. This assumes a ratio of 200 mL SIS to 6 L of 0.01 M HCl. If a higher ratio is used, more changes may be necessary.
        3.2.4. When changing 0.01 M HCl, do not leave dialysis bags exposed in the air or on the counter. Use tongs or forceps to move a dialysis bag directly from one container to another. (It is okay to have multiple dialysis bags in one container.) Dump the first container in the sink, then refill it with millipore water. The dialysis bags can now be placed in the newly filled container while the other container or containers are changed.
4. Sterilization of SIS
    4.1. Place dialysis bags of SIS in a solution of 0.18% Peracetic acid/4.8% Ethanol. Leave to stir for two hours (more time may be necessary).
    4.2. Translocate dialysis bags to 0.01 M HCl, and continue dialysis as before. Continue for at least 2 days, changing HCl at least 3 times daily.
    4.3. When dialysis is complete, dialysis tubing filled with SIS should be removed from the HCl.
    4.4. Remove the clips. Cut open one end of the dialysis tubing and pour SIS into a clean jar.
    4.5. SIS should be refrigerated until use.

5. Lyophilization of SIS
  5.1. Operating the Vertis Freezemobile
    5.1.1. Make sure the condenser is free of any water. (The condenser is the metal cylinder which opens on the front of the lyophilizer.) Ensure that the black rubber collection tubing attached to the bottom of the condenser is plugged. This can be accessed by opening the grate on the front of the lyophilizer.
    5.1.2. Close the door of the condenser, the top of the manifold, and all sample ports. If the door of the condenser or the top of the manifold are not forming a good seal apply a small amount of vacuum grease to the rubber contact surfaces.
    5.1.3. Turn on the "Refrigerate" switch. The indicator on the front of the lyophilizer will show a light beside "Condenser" and beneath "On." The light beneath "OK" will not illuminate until the condenser is cooled. The condenser temperature is indicated when the digital readout displays "C1."
    5.1.4. When the "condenser" indicator light under "OK" is illuminated, on the "Vacuum" switch. The indicator will show a light beside "Condenser" and beneath "On." The light beneath "OK" will not turn on until the chamber is sufficiently evacuated. The chamber pressure is indicated when the digital readout displays "V 1."
    5.1.5. The rollers can be used for freezing a coat of material on the inside surface of a jar. To use the rollers, first ensure that the drain tube is plugged. (This can be accessed through the door on the right side of the front of the lyophilizer.) Using 100% Ethanol, fill the roller tank to a level several millimeters above the top of the rollers. Under-filling will cause ineffective cooling while over-filling will allow ethanol to leak into the jars. The temperature of ethanol bath is indicated when the digital readout displays "T1." This bath is cooled when the "Refrigerate" switch is turned on. The "Rollers" switch controls the turning of the rollers, and may be switched off when no jar is on the rollers.
  5.2. Lyophilizing SIS
    5.2.1. Lyophilization jars, glass lids, and rubber gaskets should be cleaned with ethanol. Allow ethanol to evaporate completely before use. Mid-size jars, lids, and gaskets (3-inch diameter) should be used to fit into the roller if using the Virtis Freezemobile Jar lyophilization.
    5.2.2. Pipette 75 mL of SIS solution into the lyophilization jar. Place gasket and lid on jar.
    5.2.3. Seal the jar by covering the openings with parafilm. Note the small hole on the neck of the lid, which must be covered.
    5.2.4. Place the jar of SIS on the lyophilizer rollers for a minimum of 2 hours.
    5.2.5. Alternatively, the jar may be placed in a freezer until all material is solid. In a −80° C. freezer, this takes about 30 minutes.
    5.2.6. Prepare a spigot on the lyophilizer by inserting a glass cock with the tapered end out. The tapered end of the cock should be coated with vacuum grease.
    5.2.7. Remove the jar of SIS from the rollers (or freezer). Place springs on the hooks to hold the jar and lid together. Remove the parafilm and place the neck of the lid of the jar over the cock. Rotate the jar so that the holes in the lid and the cock do not align. The spigot can be rotated so that the jar rests on the top surface of the lyophilizer.
    5.2.8. Turn the valve switch so that it points toward the jar of S1S.
    5.2.9. More jars may be added to freeze-dry simultaneously, but add jars one or two at a time. Wait until the vacuum pressure falls to a reasonable range (e.g., 200 millitorr) to ensure that the last jar is sealed before adding subsequent jars.
    5.2.10. Leave the jars under vacuum for at least 24 hours.
    5.2.11. After lyophilization is complete, turn the switch On the spigot to point away from the jar. This will allow air into the jar.
    5.2.12. Remove the jar from the cock.
    5.2.13. Llyophilized material is not immediately used, it should be stored in a dry environment. Use a large, sealable container with Dri-Rite or another desiccant, and place containers of lyophilized material therein.
6. Rehydration of lyophilized SIS
  6.1. Place lyophilized SIS into a tube or jar.
  6.2. Add the desired quantity of liquid (typically 0.01 N HCl) to the container of SIS.
  6.3. Mixing may be accelerated by shaking, stirring, etc. Store container under refrigeration until dissolution of SIS is complete.

Sterilization of Solubilized Sis by Dialysis Against Peracetic Acid Containing Solution 1. Dialyze solubilized SIS against a large reservoir containing 0.18% peracetic acid/4.8% ethanol in water. Dialysis time may vary depending upon peracetic acid concentration, dialysis membrane molecular weight cut off, temperature, etc.
2. Transfer dialysis bags aseptically to reservoirs containing 0.01 N HCl. Dialyze extensively to reduce concentration of residual peracetic acid.
3. When dialysis is complete, dialysis tubing filled with solubilized SIS should be removed from the dialysis tank aseptically.
4. Remove dialysis clips and pour or pipette solubilized SIS into a sterile jar.
5. The disinfected solubilized SIS should be stored at 4° C. until use.

Sterilization of Sis by Direct Addition of Peracetic Acid to Sis Solution

1. Add 100% Ethanol and 32 wt % peracetic acid to solubilized SIS to create a solution with final concentration of 0.18% peracetic acid/4.8% ethanol. Stir well and leave for two hours.
2. Place solubilized SIS in aseptic dialysis bags. Dialyze against sterile solution of 0.01 N HCl.
3. When dialysis is complete, dialysis tubing filled with solubilized SIS should be removed from the dialysis tank aseptically.
4. Remove dialysis clips and pour or pipette solubilized SIS into a sterile jar.
5. The disinfected solubilized SIS should be stored at 4° C. until use.

EXAMPLE 12

Engineered ECM Compositions Regulate Cell Behavior

The three-dimensional (3D) extracellular matrix (ECM) of tissues in vivo represents a complex array of macromolecules that serves to provide biochemical and biophysical microenvironmental cues to resident cells. However, the exact role of any one biophysical feature or molecular component within the ECM in regulating cellular behavior has been difficult to elucidate due to the inherent interdependence of ECM compositional, structural, and mechanical properties. Recently, applicants have established that the 3D microstructural composition of fibrils within engineered ECMs created from purified type I collagen regulates cell-matrix adhesion, matrix remodeling, and proliferation properties of fibroblasts. It is further anticipated that altering the ratios of collagen types I and III within engineered ECMs would affect the hierarchical assembly of fibrils, and therefore the ECM signaling capacity.

Engineered ECMs were created with altered ratios of collagen types III and I ranging from 1:6 to 1:2. Application of confocal and scanning electron microscopy showed that ECMs prepared with increasing amounts of type III collagen possessed an increasing number of small diameter fibrils. Furthermore, these microstructural changes translated into alteration of matrix mechanical properties. Finally, results showed a biphasic response for fibroblast proliferation, morphology, and matrix remodeling.

EXAMPLE 13

Engineered ECM Compositions Regulate Stem Cell Differentiation

A multipotential mesenchymal stem cell line (D1) derived from mouse bone-marrow stroma was obtained from American Type Culture Collection (ATCC). D1 cells were propagated in Dulbecco's modified Eagle medium containing 4.5 g/L glucose, 110 mg/L sodium pyruvate, 100 U/ml penicillin, 100 µg/ml streptomycin, and 10% fetal bovine serum (FBS) within a humidified atmosphere of 5% carbon dioxide at 37° C. Three-dimensional collagen ECMs were prepared by dissolving native, acid-solubilized type I collagen from calf skin (Sigma Chemical Co, St. Louis, Mo.) in 0.01 N hydrochloric acid to achieve desired concentrations. As a final purification step the isolated collagen obtained from Sigma Chemical was dialyzed against an acidic solution having a low ionic strength (0.01 N HCl) for 1-2 days, using dialysis tubing or a membrane having a molecular weight cut-off selected from a range of about 3,500 to about 12,000 daltons. For sterile preparations of collagen, the purified collagen solution was layered onto a volume of chloroform. After incubation for 18 hours at 4° C., the collagen solution layer was carefully removed so as not to include the collagen-chloroform interface layer.

To produce 3D purified collagen matrices with microstructures of varied collagen fibril dimensions (e.g., length, diameter, density), collagen solutions were polymerized under different conditions. Specifically, to create collagen matrices consisting of collagen fibrils at increasing densities, collagen solutions were polymerized at final collagen concentrations of 1.0 to 3.0 mg/ml. The polymerization composition comprised a 10× phosphate buffered saline (PBS) with an ionic strength of 0.14 N and a pH of 7.4. The specific formulation of the 10× phosphate buffer is as follows:

10×PBS, pH 7.4
1.37M NaCl
0.027M KCl
0.081M $Na_2HPO_4$
0.015M $KH_2PO_4$
5 mM $MgCl_2$
1% w/v glucose To create 10×PBS buffers of different pH, the ratio of $Na_2HPO_4$ and $KH_2PO_4$ is varied. Ionic strength can be adjusted as an independent variable by varying the molarity of NaCl only. To create the 3D matrix comprising cells suspended within 3D matrix microenvironment the following components were mixed together:

1 ml solubilized collagen (e.g., type I collagen) in 0.01N HCl
150 ul 10×PBS, pH 7.4
150 ul 0.1N NaOH
100 ul 13.57 mM $CaCl_2$
100 ul 0.01 N HCl
Final Volume 1.5 ml.

The composition is mixed well after each additional component is added. The composition is then combined with a cell pellet of known cell number to create desired cell density; mixed well; and allowed to polymerize. The resulting polymerized 3D matrix has a final concentration of glucose and $CaCl_2$ of about 5.55 mM glucose and about 0.9046 mM $CaCl_2$.

To create collagen matrices consisting of collagen fibrils that varied in length and width, collagen solutions were polymerized at a pH selected from the range of 6.5-8.5. D1 cells were harvested in complete medium, collected by centrifugation, and added as the last component before polymerization. Tissue constructs were prepared at a relatively low cell density of $5 \times 10^4$ cells/ml. Previous studies by applicants have shown that this cell density is suitable for maintaining cell viability, minimizing cell-cell interaction, and allowing the study of the dynamic relationship between an individual cell and its surrounding ECM.

Polymerization of tissue constructs was conducted in 24-well culture plates maintained in a humidified environment at 37° C. Immediately after polymerization (20 minutes or less), complete medium was added and the tissue constructs were cultured for 48 hours at 37° C. in a humidified environment consisting of 5% $CO_2$ in air. After 48 hours, each of the constructs comprising D1 cells seeded within a specific ECM microstructure were cultured under 3 different conditions:

1) complete medium no supplements
2) complete medium plus $10^{-7}$ M dexamethasone
3) complete medium plus 50 µg/ml ascorbic acid For comparison purposes, parallel experiments were conducted on D1 cells grown in a standard 2D format on tissue-culture plastic. Cell behavior and morphology were monitored throughout the duration of the experiment using standard brightfield microscopy. After 24 days in culture, tissue constructs were histochemically stained with alcian blue, oil red 0, and alizirin red as indicators of chondrogenesis, adipogenesis, and osteogenesis.

Results:

The results of this experiment revealed the following:

1) multipotential stem cells seeded within engineered ECMs proliferated at rates that were dependent upon microstructural composition of the engineered ECM and the media composition;

2) time-dependent patterns of cellular condensation and aggregation exhibited by multipotential stem cells were dependent upon microstructural composition of the engineered ECM and the media composition;

3) time-dependent differentiation of multipotential stem cells seeded within engineered ECMs was dependent upon microstructural composition of the engineered ECM and the media composition;

4) maintenance of precursor or multipotential cells in an undifferentiated state in vitro was dependent upon microstructural composition of the engineered ECMs and the media composition;

5) patterns of cellular proliferation/differentiation for cells grown within 3D were different from those observed for cells grown in 2D on tissue culture plastic; and 6) Decreasing the cell density of viable multipotential stem cells within engineered ECMs led to clonal growth of a large population of cells representing a single cell lineage. Estimates of optimal cell densities for clonal growth range from about 10 cells/ml to about $10^3$ cells/ml and depend upon the specific seeding efficiencies. For most cells, cell survival is known to decrease with seeding density.

EXAMPLE 14

Engineered ECM Compositions Regulate Unipotential Stem Cell Differentiation

A unipotential stem (precursor) cell line (L1) derived from mouse and representing pre-adipocytes was obtained from American Type Culture Collection (ATCC). L1 cells were propagated in Dulbecco's modified Eagle medium containing 4.5 g/L glucose, 110 mg/L sodium pyruvate, 100 U/ml penicillin, 100 µg/ml streptomycin, and 10% fetal bovine serum (FBS) within a humidified atmosphere of 5% carbon dioxide at 37° C. To enhance cell viability, cells representing passage numbers greater than 5 were maintained in complete media in which the penicillin and streptomycin were reduced to 25 U/ml and 25 µg/ml, respectively.

Preparation of tissue constructs representing L1 cells seeded within 3D engineered ECMs of different microstructural compositions was carried out as described in Example 13. Immediately after polymerization (20 minutes or less), complete medium was added and the tissue constructs were cultured for 48 hours at 37° C. in a humidified environment consisting of 5% $CO_2$ in air. After 48 hours, each of the constructs comprising L1 cells seeded within a specific ECM microstructure were cultured under 3 different conditions:

1) complete medium no supplements; medium changed every 2 days thereafter;

2) complete medium no supplements and post differentiation medium treatment every 2 days thereafter; and 3) differentiation medium and post differentiation medium treatment every 2 days thereafter The differentiation medium consists of DMEM supplemented with 10% FBS, 25 U/ml penicillin, 25 µg/ml streptomycin, 115 µg/ml methyl-isobutyl xanthine, 10 µg/ml insulin, and $5 \times 10^{-7}$ M dexamethasone. The post differentiation medium consisted of DMEM supplemented with 10% FBS, 25 U/ml penicillin, 25 µg/ml streptomycin, and 10 µg/ml insulin. For comparison purposes, parallel experiments were conducted on L1 cells grown in a standard 2D format on tissue-culture plastic. Cell behavior and morphology were monitored throughout the duration of the experiment using standard brightfield microscopy.

Results:

The results of this experiment revealed the following:

1) unipotential stem (precursor) cells seeded within engineered ECMs proliferated at rates that were dependent upon microstructural composition of the engineered ECM and the media composition;

2) time-dependent patterns of cellular condensation and aggregation exhibited by unipotential stem cells were dependent upon microstructural composition of the engineered ECM and the media composition;

3) time-dependent differentiation of unipotential stem cells into mature adipocytes seeded within engineered ECMs was dependent upon microstructural composition of the engineered ECM and the media composition;

4) maintenance of precursor cells in an undifferentiated state in vitro was dependent upon microstructural composition of the engineered ECMs and the media composition; and 5) patterns of cellular proliferation/differentiation for cells grown within 3D were different from those observed for cells grown in 2D on tissue culture plastic.

EXAMPLE 15

Effect of Fibril Microstructure and Mechanical Properties of 3D ECM on Cultured Stem Cells Multi-potential stem cells derived from the bone marrow of mice (D1s; ATCC) were suspended at $5 \times 10^4$ cells/ml within purified type I collagen solutions (Sigma Chemical Co.) at varying collagen concentrations ranging from 1.5-3.6 mg/ml using the procedures described in Example 13. Tissue constructs consisting of D1 cells entrapped within a 3D ECM were formed by inducing self-assembly (polymerization) at pH 7.4, 137 mM NaCl, and 37° C. For this specific example, an increase in collagen concentration as a self-assembly parameter, was used to generate a 3D ECM microenvironment in which the density of the resultant fibrils and stiffness (linear or elastic modulus) of the matrix were systematically increased. The 3D constructs and resident cells were maintained in one of three different media formulations (Table 8) at 37° C. in a humidified environment consisting of 5% $CO_2$ in oxygen for periods of time up to 4 weeks. Basal medium consisted of Dulbecco's modified Eagle's medium supplemented with 4 mM L-glutamine, 4.5 g/L glucose, 1.5 g/L sodium bicarbonate, 1 mM sodium pyruvate, 10% fetal bovine serum, 100 U/ml penicillin, and 100 µg/ml streptomycin. For comparison purposes, D1 cells also were cultured in a parallel fashion in the standard 2D format on the surface of tissue culture plastic.

TABLE 8

Medium formulations used to culture D1 cells

| Medium Designation | Medium Formulation |
|---|---|
| A | Basal medium supplemented with 1 µM dexamethasone, 0.5 mM isobutylmethylxanthine, 1 µg/ml insulin |
| B | Basal medium supplemented with 0.1 µM dexamethasone, 8 µg/ml ascorbic acid, 5 mM β-glycerophosphate |
| C | Basal medium with no additives |

After various periods of time, the proliferative and differentiation status of the cells were determined qualitatively or quantitatively. Qualitative evaluation of cell number and morphology was conducted several times a week using light microscopy. Real-time RT-PCR was used to quantify and compare the expression levels of CFBA1 (runx2), LPL (lipoprotein lipase), and procollagen II as indicators of osteogenesis (bone formation), adipogenesis (fat formation), and chondrogenesis (cartilage formation), respectively. Histochemical stains, including alkaline phosphatase and oil red 0, were applied to whole mount or cryosectioned samples to detect osteogenic and adipogenic activity, respectively. In some cases immunohistochemical staining was used to corroborate results.

Cells grown in basal culture medium with no additives (medium formulation C) on standard tissue culture plastic (A) and within 3D ECM microenvironments of controlled fibril density and stiffness showed distinct growth patterns and morphologies. Results showed as the fibril density and stiffness of the 3D ECM microenvironment increased, the proliferative capacity of the cells decreased. The dependence of D1 proliferation on the stiffness of the 3D ECM microenvironment was noted for all media formulations studied. More specifically, D1 cells grown on plastic or within the low stiffness 3D ECM microenvironment showed an increased number of spindle-shaped cells. Within 2 weeks the cells on plastic reached confluence and formed a sheet of cuboidal shaped cells. On the other hand, spindle-shaped cells were evident within the low stiffness ECM even after 4 weeks of culture. These cells appeared to remain undifferentiated and populated the ECM uniformly. Growth patterns indicative of isolated clonogenic events were higher in frequency within ECMs of increased stiffness.

The observed differences in the growth patterns and morphologies adopted by cells grown in the 2D and 3D microenvironments suggested that the multi-potential cells were being directed down distinct differentiation patterns. Limited directed differentiation appeared to occur for cells grown on plastic or within the low stiffness ECMs (1.5 mg/ml). Interestingly, D1 cells grown within 3D ECMs of high stiffness (3.4 mg/ml) formed regional aggregates of cells indicative of osteogenesis and/or skeletal myogenesis. Osteogenesis but not myogenesis events were also observed with engineered ECMs of moderate stiffness (3 mg/ml). The biochemical composition of the media also could be varied to enhance the differentiation of cells down a specific pathway or to maintain cells in a relatively undifferentiated state. Specifically, cells grown in medium formulation A demonstrated a high frequency of adipogenesis on plastic and within 3D ECMs of low fibril density and stiffness (1.5 mg/ml). As the fibril density and stiffness of the 3D ECM microenvironment increased, adipogenesis events decreased and osteogenesis increased. Medium formulation B appeared to support differentiation of D1 cells into fat (adipogenesis) and (bone) osteogenesis on plastic. Limited areas of osteogenesis and adipogenesis were noted amongst a large number of spindle-shaped cells for D1 cells grown within ECMs of low stiffness under these same medium conditions. As the stiffness of the 3D ECM increased, cells more uniformly developed regional areas of osteogenesis and myogenesis-like events. A 2D projection of one confocal image revealed cells organized or fused to form a multi-cellular structure reminiscent of a myotube. These events were limited to 3D ECM microenvironments of high stiffness (3.4 mg/ml and greater). While these myotube-like events were noted in all three medium formulations, they appeared to occur more frequently in medium formulations B and C. The cells of the myotube-like structure were stained immunohistochemically for F-actin to demonstrate the fusion of and connectivity of the actin cytoskeleton between individual cells.

Real-time RT-PCR confirmed that biophysical features of the 3D ECM microenvironment (e.g., fibril density and ECM stiffness) could be modulated to regulate stem cell growth and differentiation. The differences in gene expression patterns for D1 cells grown for two weeks on tissue culture plastic (Plastic) and within 3D engineered ECMs prepared at low (1.5 mg/ml), moderate (3.0 mg/ml), and high fibril density and stiffness (3.6 mg/ml) were analyzed. Again, cells subjected to each of these 2D and 3D culture formats were maintained in one of three different media formulations (Table 8).

The tissue specific genes CBFA1 (runx2), LPL (lipoprotein lipase), and Pro Col II (procollagen II) were selected as indicators of osteogenesis, adipogenesis, and chondrogenesis, respectively. Results showed that cells grown for 2 weeks on 2D plastic in the basal medium (no additives) remain relatively undifferentiated, more specifically, limited expression of the osteogenic, adipogenic, and chondrogenic indicators. On the other hand, D1 cells show an increase in LPL (adipogenesis) when cultured on plastic in the presence of Medium A or Medium B. The expression of LPL correlates well with the observed fat cell morphology developed within the cultures. Interestingly, the gene expression patterns developed by cells grown within a 3D ECM microenvironment were dramatically different from those observed for cells grown on plastic. Specifically, the expression of CBFA1, indicative of osteogenesis, could be enhanced by growing the cells within 3D ECMs of increased stiffness or Medium B. Again, the increased expression of CFBA1 correlated well with cell morphologies and histochemical staining. Interestingly, chondrogenesis events as indicated by high procollagen II expression appeared to be enhanced within D1 cells cultured in 3D ECMs of high stiffness.

The starting cell density was also a critical determinant of the stem cell fate within the 3D culture formats studied. Clonal growth and cell differentiation events were favored by increasing the ECM stiffness and/or by decreasing the starting cell density within a given 3D ECM format. Adipogenesis was favored by decreasing the ECM stiffness and/or by increasing the cell density. Interestingly, adipogenesis was observed within high stiffness 3D ECMs only when the cell seeding density approached $1 \times 10^6$ cells/ml and above.

EXAMPLE 16

Cell Culture

Low passage neonatal human dermal fibroblasts (NHDFs) were obtained from Cambrex Bioproducts (Walkersville, Md.). NHDFs were propagated in fibroblast basal medium supplemented with human recombinant fibroblast growth factor, insulin, gentamicin, amphotericin-B, and fetal bovine serum (FBS) according to manufacturer's recommendations. Cells were grown and maintained in a humidified atmosphere of 5% $CO_2$ at 37° C. Cells representing a limited passage number of 20 or less were used for all experiments.

EXAMPLE 17

Preparation of 3D Engineered ECMs and 3D Tissue Constructs

Purified type I and type III collagens, that were solubilized from bovine dermis and human placenta, respectively, were obtained from Sigma Chemical Company (St. Louis, Mo.). Three-dimensional engineered ECMs were prepared at a constant collagen type I concentration of 1.5 mg/ml and type III collagen concentrations of either 0, 0.25, 0.50, and 0.75 mg/ml (Table 9) using the general procedures described in Example 13. The polymerization buffer consisted of 10× phosphate buffered saline (PBS) with an ionic strength of 0.14 M and a pH of 7.4. All 3D engineered ECMs and tissue constructs were polymerized in vitro within a humidified environment at 37° C. To determine the cellular signaling capacity of each 3D ECM microenvironment, 3D tissue constructs were formed by first harvesting NHDFs in complete media and then adding the cells as the last component to the collagen solutions prior to polymerization. Tissue constructs were prepared at a relatively low cell density of $5 \times 10^4$ cells/ml in order to minimize cell-cell interactions. Immediately after polymerization (20 minutes or less), complete medium was added and the tissue constructs were maintained at 37° C. in a humidified environment consisting of 5% $CO_2$ in air.

TABLE 9

Summary of formulations for 3D engineered ECMs prepared with varied ratios of collagen types I and III.

| Type I Collagen (mg/ml) | Type III Collagen (mg/ml) | Total Collagen (mg/ml) | Collagen Type I/III Ratio | Type III Collagen (% of Total) |
|---|---|---|---|---|
| 1.5 | 0 | 1.50 | 0 | 0 |
| 1.5 | 0.25 | 1.75 | 6:1 | 14.3% |
| 1.5 | 0.50 | 2.00 | 3:1 | 25.0% |
| 1.5 | 0.75 | 2.25 | 2:1 | 33.3% |

EXAMPLE 18

Preparation of Two-Dimensional (2D) ECM Surface Coatings

To prepare 2D surfaces coated with the different ECM compositions, solutions containing collagen type I (1.5 mg/ml) and varying concentrations of collagen type III (0, 0.25, 0.5, and 0.75 mg/ml) were aliquoted (300 µl/well) into tissue culture plates (24-well) and air-dried within a laminar flow hood for approximately 18 hours. Well plates containing 2D ECM surface coatings were equilibrated with PBS, pH 7.4, prior to seeding the NHDFs at a density of $2.5 \times 10^4$ cells/well. Complete medium was added and the NHDFs on the surface of the 2D ECM coatings were maintained at 37° C. in a humidified environment consisting of 5% $CO_2$ in air.

EXAMPLE 17

Qualitative and Quantitative Analysis of 3D ECM Microstructural Composition

Two quantitative parameters describing the 3D ECM microstructural composition, fibril area fraction (a 2D approximation of 3D fibril density) and fibril diameter, were determined based upon confocal reflection and scanning electron microscopy (SEM) images. Prior to microstructural analysis, engineered 3D ECM constructs were polymerized within four-well Lab-Tek coverglass chambers (Nalge Nunc International, Rochester, N.Y.) and placed within a humidified environment at 37° C. where they were maintained for approximately 15 hours. For measurements of fibril area fraction, the confocal microscope was used to obtain high resolution, 3D, reflection images of the component collagen fibrils within each ECM (Brightman at al., Biopolymers 54: 222-234, 2000; Voytik-Harbin et al., Methods Cell Biol 63: 583-597, 2001). Three images (at least 10 µm in thickness) were taken at random locations within each of 2 specimens representing a given 3D ECM composition. The confocal image stacks were then read into Matlab (The Mathworks, Natick, Mass.), and 2D projections, representing 21 z-sections, of each image were created and a threshold chosen for binarization. Using a built-in function in Matlab, the area occupied by collagen fibrils (white pixels) was calculated, converted to $\mu m^2$ based upon the pixel sizes, and normalized to the total image area.

Fibril diameter measurements were made by applying Imaris 4.0 (Bitplane Inc., Saint Paul, Minn.) to both confocal reflection and SEM images of engineered ECM constructs. For SEM imaging, engineered ECM constructs were fixed in 3% glutaraldehyde in 0.1M cacodylate at pH 7.4, dehydrated with ethanol, and critical point dried. Samples were sputter-coated with gold/palladium prior to imaging. Duplicate samples were imaged in a JEOL (Peabody, Mass.) JSM-840 SEM using 5 kV accelerating voltage and a magnification of 3,000×. Digital images were captured using 1280×960 resolution and 160 second dwell time. From each image obtained from duplicate samples, forty fibrils were chosen at random (10 fibrils per quadrant). Five lines were drawn perpendicular to the long axis of each fibril using the measurement tool in Imaris (Brightman at al., Biopolymers 54: 222-234, 2000). The average number of pixels representing the fibril diameter was then converted into µm based upon the known pixel size.

EXAMPLE 18

Measurement of Tensile Mechanical Properties of 3D Engineered ECMs

Specimens for mechanical testing were prepared by polymerizing each soluble ECM formulation in a "dog bone" shaped mold as described previously (Roeder et al., J Biomech Eng, 124: 214-222, 2002). In brief, the mold consisted of a glass slide and a piece of flexible silicone gasket. The gauge section of the mold measured 10 mm long, 4 mm wide, and approximately 1.5 mm thick. Neutralized ECM solution was added to each mold and allowed to polymerize at 37° C. in a humidified environment where they were maintained for 18-20 hours prior to tensile loading. Polypropylene mesh was embedded in the ends of each 3D ECM construct to facilitate clamping for mechanical loading. Low-magnification, 4D images (x, y, z, and time) of each ECM construct during uniaxial tensile loading were acquired using an integrated mechanical loading-stereomicroscope set-up. This set-up involved interfacing a modified (Roeder et al., J Biomech Eng, 124: 214-222, 2002.) Minimat 2000 miniature materials tester (Rheometric Scientific, Inc., Piscataway, N.J.) with a Stemi 2000-C Stereomicroscope (Carl Zeiss MicroImaging; Thornwood, N.Y.) mounted with a DFC480 high-resolution color digital camera (Leica Microsystems, Cambridge, UK). Strategically placed right-angle prisms (Edmund Industrial Optics, Barrington, N.H.) were used to monitor changes in specimen thickness (z-direction) throughout the loading process. The image field was positioned to include the clamp that was attached to the load cell in order to provide a "fixed" frame of reference throughout the loading process. Each ECM construct was loaded uniaxially at an extension rate of 1 mm/min (corresponding to a strain rate of $\dot\epsilon \approx 0.04$/min) until failure. Images were collected at a rate of 0.1 frames/sec to provide sequential images at 0.64% strain intervals. Changes in the width (x-direction) and thickness (z-direction) dimensions of the specimen's gauge section were measured directly from low-magnification digital camera images representing the width and thickness of the specimen and used to calculate cross-sectional area. The mechanical behavior of each specimen, including engineering stress ($\sigma_e$), true stress ($\sigma_t$), and applied strain ($\epsilon_{ap}$) were calculated from load-displacement recordings provided by the Mini-mat. Applied strain was calculated by simplifying the Lagrangian strain definition (Malvern, Introduction to the Mechanics of a Continuous Medium. Upper Saddle River, N.J.: Prentice-Hall, 1969) for a simple stretch λ (new length divided by original length) as indicated below $$\epsilon_{ap} = 1/2(\lambda^2 - 1) \qquad (1)$$

Engineering stress was calculated as $$\sigma_e = \frac{F}{A_o} \quad (2)$$

where, F was the force recorded by the Minimat and $A_o$ was the initial cross-sectional area (width×thickness) within the center of the specimen (Callister et al., *Materials Science and Engineering: An Introduction*. 3rd edition. New York, N.Y.: John Wiley & Sons, 1994). For calculation of true stress, the actual cross-sectional area of each specimen at a specific load was imaged, quantified, and substituted for $A_o$ in the engineering stress equation above. From the resulting stress-strain relationships ultimate strength (maximum stress achieved during tensile loading), failure strain (strain at which specimen fails), and linear or elastic modulus (stiffness; slope of linear region of stress-strain curve) were determined.

EXAMPLE 19

Multi-Dimensional Confocal Imaging of Cell-ECM Interactions

All multi-dimensional imaging was performed on a Bio-Rad Radiance 2100 MP Rainbow (Bio-Rad, Hemel Hempstead, England) multi-photon/confocal system adapted to a TE2000 (Nikon, Tokyo, Japan) inverted microscope with a heated stage set at 37° C. (ALA Scientific Instruments, Westbury, N.Y.). A custom-designed environmental chamber was adapted to the microscope to provide tissue constructs with a sterile environment of 5% $CO_2$ in humidified air (Pizzo et al., *J Appl Physiol* 98: 1909-1921, 2005). For each of the engineered ECMs studied, at least 5 individual cells were repeatedly monitored during the first 5 hours following construct polymerization. During the collection of time-lapse images, the confocal microscope was used in a reflection (back-scattered light) mode to obtain image stacks of an individual cell and the component collagen fibrils of its surrounding ECM as described previously (Brightman et al., *Biopolymers* 54: 222-234, 2000; Voytik-Harbin et al., *Methods Cell Biol* 63: 583-597, 2001). Images were collected at 30-minute intervals and a z-step of 0.5 µm to minimize exposure of the tissue constructs to radiation from the confocal microscope laser.

EXAMPLE 20

3D Cell Morphometric Analysis

Three-dimensional confocal images used for qualitative and quantitative analyses of NHDF morphology were collected using the confocal microscope in a combination reflection-epifluorescence mode (Voytik-Harbin et al., *Methods Cell Biol* 63: 583-597, 2001; Voytik-Harbin et al., *Microsc Microanal* 9: 74-85, 2003). Immediately following the 6-hr time-lapse imaging, tissue constructs were stained with the vital dye, Cell Tracker Green (Molecular Probes, Eugene, Oreg.), to facilitate discrimination of the cell from the surrounding collagen ECM. The processed image stack was used to determine fundamental morphological parameters including number of cytoplasmic projections, cell volume, 3D cell surface area, length, width, and height as described previously (Pizzo et al., *J Appl Physiol* 98: 1909-1921, 2005). Since each cell had a relatively unique orientation within the 3D matrix, these morphological parameters were defined based on a cellular coordinate system. Morphological evaluation was conducted on a total of 10 to 23 cells for each of the 3D ECM compositions studied.

EXAMPLE 21

Determination of 3D Average Local Principal Strains and Points of Maximum Local Principal Strain Consecutive time-lapse confocal reflection images representing the time-dependent deformation to the collagen fibril microstructure induced by an individual resident cell provided the basis for quantification of local ECM remodeling in terms of 3D displacements and strains. Strains were quantified using an incremental digital volume correlation (IDVC) algorithm developed previously by our laboratory (Roeder et al., *J Biomech Eng* 126: 699-708, 2004). To determine 3D average local principal strains within the surrounding ECM induced by an individual cell, first the 15×15×3 grid of displacements (174.2×174.2×24 µm³ total volume) from the IDVC algorithm were converted into 3D strains with x, y, and z directions based on the confocal coordinate system. The strains in the entire volume were then averaged in each of the three confocal directions to give a 3×3 symmetric matrix of average strains, $\epsilon_{avg}$, such that $$\varepsilon_{avg} = \begin{bmatrix} \varepsilon_{xx} & \varepsilon_{xy} & \varepsilon_{xz} \\ \varepsilon_{xy} & \varepsilon_{yy} & \varepsilon_{yz} \\ \varepsilon_{xz} & \varepsilon_{yz} & \varepsilon_{zz} \end{bmatrix} \quad (3)$$

where $\epsilon_{ij}$ are average strains in the confocal coordinate system directions. This average strain matrix in Equation (3) was then solved using eigenvector analysis (Strang et al., *Linear Algebra and Its Applications*. 3rd edition. San Diego, Calif.: Academic Press, 1988) to determine 3 average principal strains ($E_1$, $E_2$, $E_3$) and associated directions such that, $$\varepsilon_{avg} \cdot [V] = [V] \cdot \begin{bmatrix} E_1 & 0 & 0 \\ 0 & E_2 & 0 \\ 0 & 0 & E_3 \end{bmatrix} \quad (4)$$

where [V] is a 3×3 matrix such that the column vectors ($V_1$, $V_2$, $V_3$) are the directions of the principal strains given by $$[V]=[V_1 V_2 V_3] \quad (5)$$

Therefore, the deformation induced by each cell had a unique set of average principal strains and directions in 3D.

Another analysis was performed to determine on a finer scale where the maximum local principal strains within the 3D ECM occurred in relationship to the cell. This analysis involved determination of local principal strains $E_1$, $E_2$, and $E_3$, each with unique principal direction, at each of the 15×15×3 grid points. The maximum compressive $E_1$, $E_2$, and $E_3$ were then identified within the image volume. The location of each maximum compressive principal strain was known in terms of its IDVC grid location and also in µm. The distance from these three-maximum principal strain locations to the center of the cell body in 3D could then be determined using simple vector relationships. The locations of the maximum compressive principal strains did not necessarily occur at the same grid locations for each cell.

EXAMPLE 22

Labeling and Visualization of Actin Cytoskeleton within 3D Engineered Tissue Constructs Tissue constructs formed by seeding NHDFs within specific 3D ECM formulations during polymerization were prepared in four-well Lab-Tek coverglass chambers (Nalge Nunc International, Rochester, N.Y.) for visualization of the F-actin cytoskeleton. At specified timepoints, constructs were fixed and permeabilized with a solution containing 0.1% Triton 100x and 3% paraformaldehyde, post-fixed in 3% paraformaldehyde, and treated with 1% bovine serum albumin to minimize non-specific binding. The constructs were then stained overnight at 4° C. with Alexa Fluor 488 Phalloidin (Molecular Probes, Eugene, Oreg.) and rinsed. Three-dimensional images of the F-actin distribution within an individual cell as well as its surrounding ECM were collected simultaneously using confocal microscopy in a combined epifluorescence and reflection mode. When necessary, images were deconvolved using AutoDeblur (Autoquant Imaging, Inc., Watervliet, N.Y.).

EXAMPLE 23

Qualitative and Quantitative Determination of Cell Proliferation

Quantification of NHDF proliferation and its dependency on the 3D ECM microenvironment involved preparing 3D tissue constructs within 24-well tissue-culture plates using an alamarBlue-based proliferation assay as described previously (Pizzo et al., *J Appl Physiol* 98: 1909-1921, 2005; Voytik-Harbin et al., *In Vitro Cell Dev Biol Anim* 34: 239-246, 1998). For comparison purposes, the proliferative capacity of NHDF was also determined for an equivalent number of cells seeded directly onto the plastic surface of a well-plate as well as 2D plastic surfaces coated with different ECM compositions consisting of type I collagen in the presence of varying amounts of type III collagen. At time points representing 24 and 48 hours after construct polymerization and/or cell seeding, each well and tissue construct was examined microscopically to observe the viability, number, and morphology of the cells. The medium from each well then was replaced with fresh medium containing the metabolic indicator dye alamar-Blue (10% v/v; BioSource International, Inc., Camarillo, Calif.). Twenty-four hours later, dye reduction was monitored spectrofluorometrically using a FluoroCount Microplate Fluorometer (Packard Instruments, Meriden, Conn.) with excitation and emission wavelengths of 560 nm and 590 nm, respectively. Background fluorescence measurements were determined from wells containing only dye reagent in culture medium. Maximum levels of relative fluorescence were determined from alamarBlue solutions that were autoclaved to induce complete dye reduction. The mean and the standard deviation values for all fluorescence measurements were calculated and subsequently normalized with respect to the background and maximum fluorescence readings. All experiments were performed in triplicate and repeated at least three times. When relevant, statistical analyses were performed using Matlab and included an analysis of variance (ANOVA). The Tukey-Kramer method for multiple comparisons ($p<0.05$) was then applied. The two-tailed t-test ($\alpha=0.05$) was applied for pairwise comparisons.

EXAMPLE 24

Three-Dimensional Microstructural Composition of Engineered ECMs Depends upon Collagen Type I/III Ratio This study utilized the application of confocal microscopy in a reflection mode and SEM facilitated microstructural analysis from both 2D and 3D perspectives as well as at two different limits of resolution. SEM provided high-resolution (approximately 10 nm) 2D images of ECM microarchitecture after specimens had been critical point dried. On the other hand, confocal reflection microscopy allowed visualization of the 3D microstructural organization of component collagen fibrils within engineered ECMs in their fully hydrated or native state; however the resolution obtained with confocal imaging is approximately 200 nm, twenty times less than that obtained with SEM.

Figure 2A:
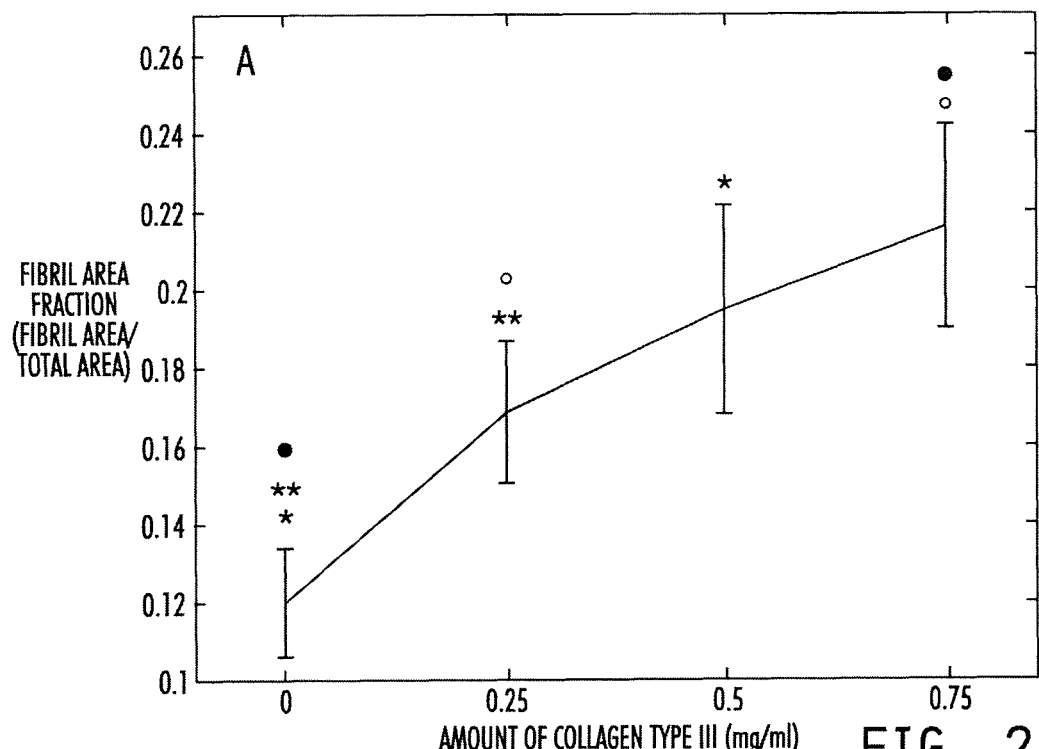
FIGS. 2A & 2B represent a series of graphs showing the quantification of fibril area fraction (FIG. 2A) and fibril diameter distribution (FIG. 2B) based upon confocal and SEM images, respectively. All fibril area fraction relationships showing statistically significant differences ($p<0.05$) are indicated with symbols (*, **, ●, ○).
Figure 2B:
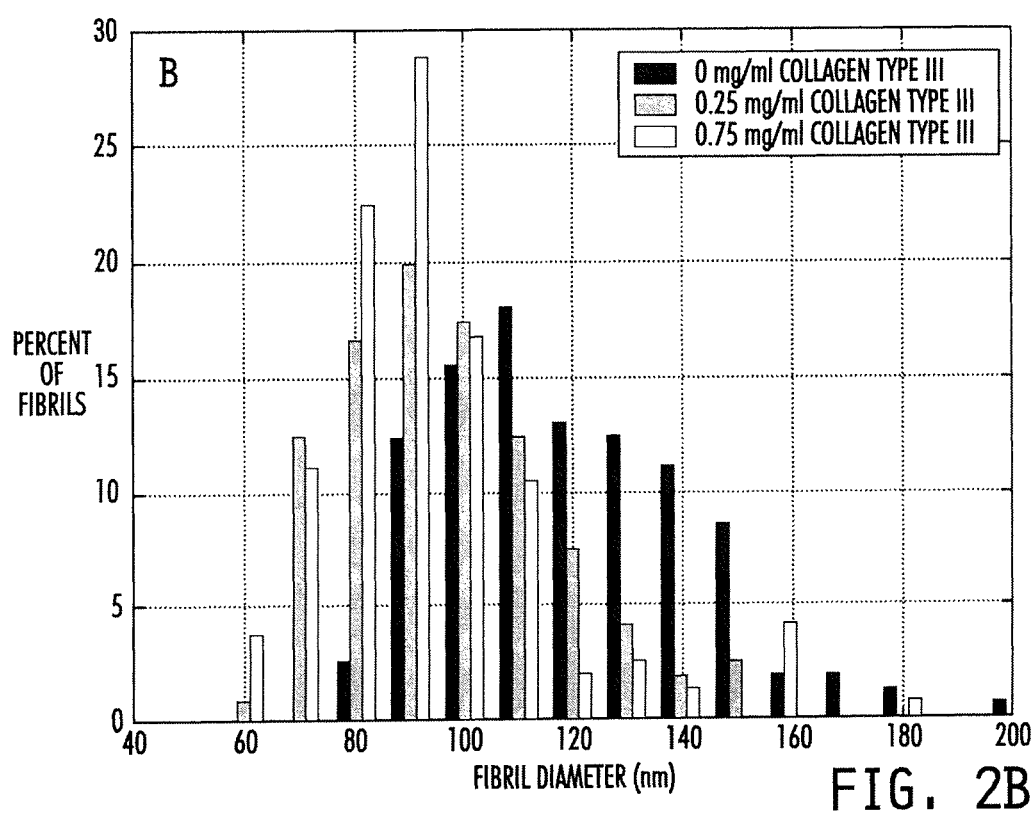

Both confocal and SEM images showed that ECMs prepared with increased amounts of type III collagen possessed an increased number or density of collagen fibrils. The fibril area fraction (FIG. 2A) was quantified from confocal reflection images and showed a nearly linear increase with type III collagen over the range studied. Engineered ECMs prepared from type I collagen alone had a fibril area fraction of 12.0±1.4% compared to 21.5±2.6% for those formed in the presence of the highest concentration (0.75 mg/ml) of type III collagen. In addition to this effect on fibril density, increased levels of type III collagen resulted in a downward shift in the fibril diameter distribution (Table 10) and (FIG. 2B). The mean fibril diameter as determined from SEM images for ECMs prepared with type I collagen alone was 115.2±23.2 µm. The mean fibril diameter showed a significant ($p<0.05$) decrease to 94.8±23.0 µm and 87.0±17.0 µm for ECMs in which collagen III was added at levels of 0.25 mg/ml and 0.75 mg/ml, respectively. In general, fibril diameter measurements made from confocal reflection images corroborated SEM results; however, fibril diameter values obtained from confocal images were greater than those obtained using SEM (Table 10) since confocal imaging was conducted on unprocessed, fully hydrated specimens. It should be noted that fibril diameter measurements made using confocal reflection imaging were considered somewhat less accurate and less precise since fibril diameters were near the limit of resolution for this imaging technique.

TABLE 10

Collagen fibril diameter measurement data for 3D engineered ECMs prepared from type I collagen in the absence and presence of type III collagen as determined from scanning electron (SEM) and confocal reflection (CRM) images.

| Fibril Diameter | Type I Collagen (1.5 mg/ml) | | Type I Collagen (1.5 mg/ml) + Type III Collagen (0.75 mg/ml) | |
|---|---|---|---|---|
| (nm) | SEM | CRM | SEM | CRM |
| Mean ± SD | 115.16 ± 23.18 | 412.63 ± 76.35 | 87.04 ± 17.00 | 384.60 ± 71.96 |
| Median | 112 | 408 | 86 | 378 |
| Range | 78-194 | 200-664 | 56-176 | 236-628 |

EXAMPLE 25

Mechanical Properties of Engineered ECMs Depend Upon Collagen Type I/III Ratio Previously, we showed that engineered ECMs prepared at increasing concentrations of type I collagen featured an increase in fibril density but no significant change in fibril diameter (Roeder et al., *J Biomech Eng*, 124: 214-222, 2002). Furthermore, this change in ECM microstructure, specifically an increase in collagen fibril density, was found to be positively correlated with ECM tensile strength and stiffness (linear or elastic modulus (Roeder et al., *J Biomech Eng*, 124: 214-222, 2002)). Traditionally, mechanical properties for collagen-based matrices have been calculated based upon engineering stress (Osborne et al., *Med Biol Eng Comput* 36: 129-134, 1998; Ozerdem et al., *J Biomech Eng* 117: 397-401, 1995; Roeder et al., *J Biomech Eng*, 124: 214-222, 2002), which assumes no change in specimen cross-sectional area during mechanical loading. However, since it is known that our engineered ECMs exhibit Poisson's ratios on the order of 2 to 4 (Roeder et al., *J Biomech Eng*, 124: 214-222, 2002; Voytik-Harbin et al., *Microsc Microanal* 9: 74-85, 2003), true stress was calculated to account for the significant reduction in cross-sectional area experienced by the scaffolds during testing. Since our experimental set-up facilitated the continuous monitoring of changes in specimen cross-sectional area during tensile loading, true stress calculated parameters were considered to most accurately reflect mechanical behavior of the ECMs.

ECMs engineered from type I collagen in the presence of type III collagen over the range of 0 to 0.75 mg/ml (type III collagen content of 0 to 33.3%) showed biphasic responses in terms of true stress calculated parameters ultimate strength and stiffness. The mean ultimate strength obtained for ECMs prepared from 1.5 mg/ml type I collagen alone was 136.7±49.9 kPa. Addition of collagen III resulted in significant reductions in ultimate strength, with 66.7±4.2 kPa ($p=0.0016$) and 75.1±22.7 kPa ($p=0.0085$) values being measured for ECMs prepared at collagen III levels of 0.25 mg/ml and 0.75 mg/ml, respectively. The linear or elastic modulus (stiffness), as determined from the linear region of the stress-strain curve, also showed reductions of 32% ($p=0.0002$) at the 0.25 mg/ml collagen III level and 18% ($p=0.189$) at the 0.75 mg/ml collagen III level compared to those where no collagen III was added. A decline in failure strain with increasing type III collagen content was noted. Specifically, failure strain values decreased significantly from 62.2±12.2% when no collagen III was added to 53.3±1.4% ($p=0.048$) and 43.0±5.9% ($p=0.002$) when the type III collagen content was 0.25 mg/ml and 0.75 mg/ml, respectively. Finally, increasing the type I collagen content from 1.5 to 3 mg/ml increased ECM ultimate strength and stiffness, confirming previous findings (Roeder et al., *J Biomech Eng*, 124: 214-222, 2002). ECMs prepared at 3 mg/ml type I collagen had ultimate strength and stiffness values that were 2.2 and 3.5 times, respectively, those obtained for ECM prepared at 1.5 mg/ml type I collagen.

EXAMPLE 26

3D Cell Morphology Depends Upon Collagen Type I/III Ratio

The ability of cells to sense and respond to changes in the 3D ECM microenvironment that resulted from the addition of type III collagen initially was assessed by determining and comparing 3D cell morphology and cell-induced ECM remodeling (deformation and reorganization of component collagen fibrils). Three-dimensional morphometric analyses for cells seeded within the different ECM microenvironments were conducted at 6 and 12 hours following tissue construct formation. ECM remodeling by individual cells was repeatedly monitored during a 5 to 6 hour time window shortly after construct formation.

Notable differences in 3D cell morphometric parameters were detected at both 6 and 12 hours as the cells probed and adapted to their extracellular microenvironment.

One of the more prominent differences noted at 6 hours was that cells seeded within engineered ECMs prepared at the lowest type III collagen content (0.25 mg/ml) took on a rounded morphology with multiple short projections. This cell morphology contrasted that observed within ECMs prepared with 0.5 mg/ml and 0.75 mg/ml type III collagen. At these higher collagen III levels a large percentage of cells took on a more spindle-shaped cell body with fewer but prominent lengthy projections. Cells seeded within ECMs prepared from type I collagen alone took on a more spindle, bipolar shape and possessed the fewest (on average 2 to 4) but longest projections at the 6-hour time point.

Figure 3A:
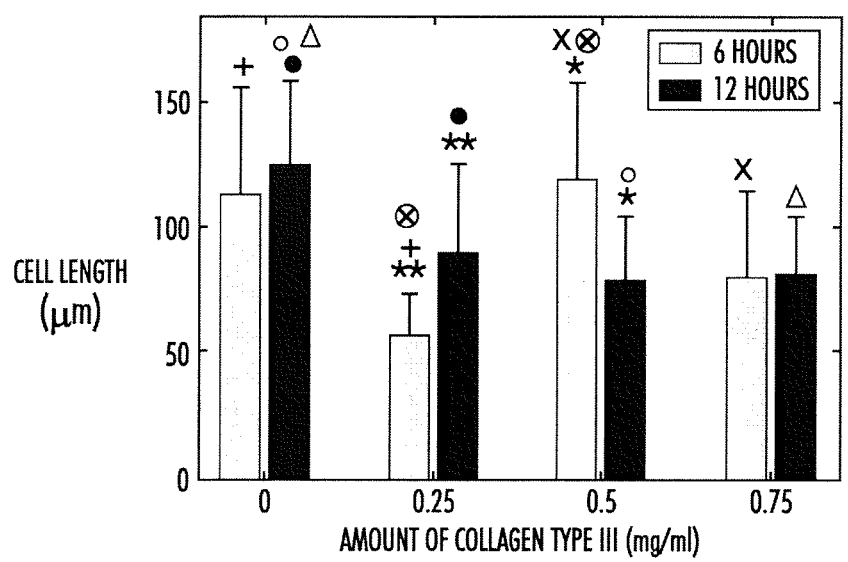
FIGS. 3A-3D represent a series of graphs showing cell length (FIG. 3A), length/width ratio (FIG. 3B), width (FIG. 3C), and surface area (FIG. 3D) determined and compared for neonatal human dermal fibroblasts (NHDFs) seeded within 3D ECMs prepared with 1.5 mg/ml type I collagen, and a type III collagen content that varied from 0 to 0.75 mg/ml. Results represent the means and standard deviations for n 23 cells analyzed for each ECM formulation at a given time point. All groups showing statistically significant differences ($p<0.05$) are marked with the same symbol.
Figure 3B:
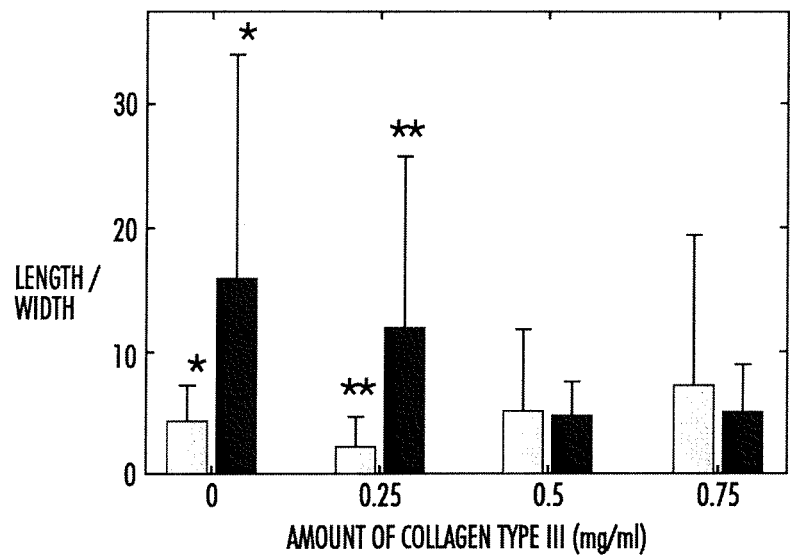
Figure 3C:
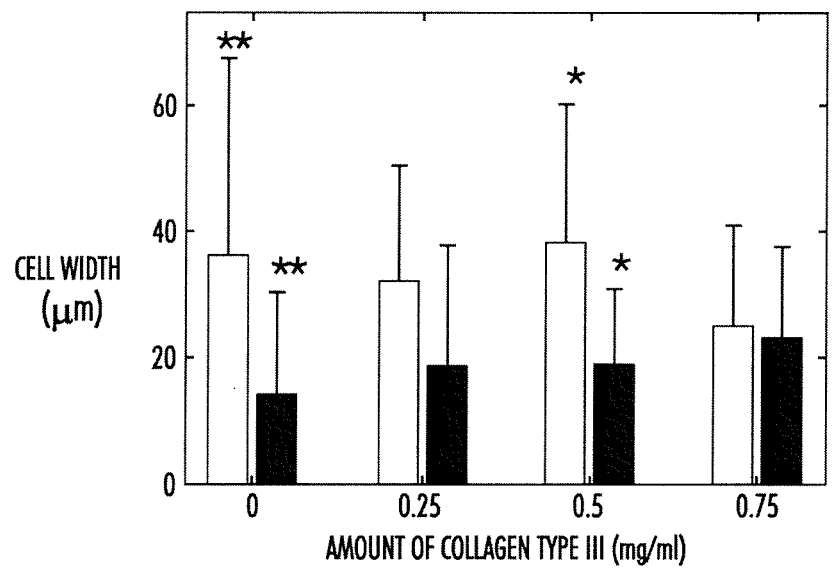
Figure 3D:
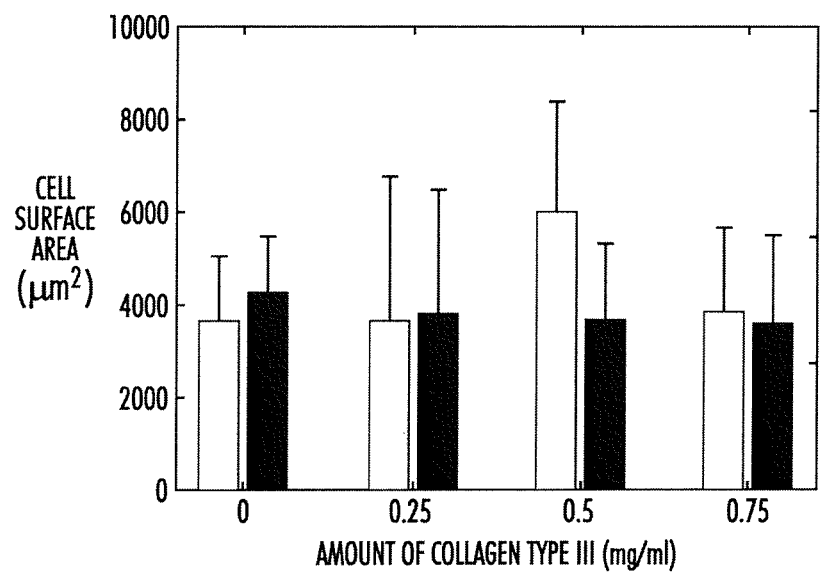
Figure 4A:
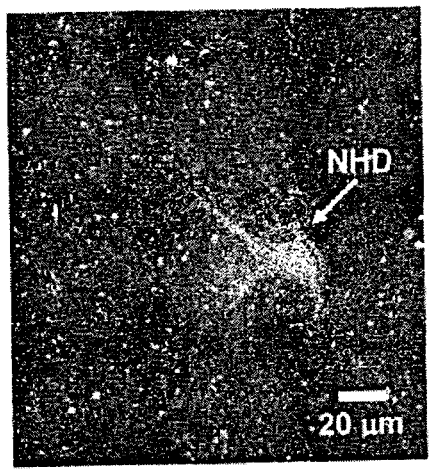
FIGS. 4A-4D represent a series of images depicting cell contractility and matrix remodeling by individual NHDFs resident within type I collagen (1.5 mg/ml) ECMs prepared with type III collagen concentrations of 0.25 mg/ml (FIGS. 4A and 4B) and 0.75 mg/ml (FIGS. 4C and 4D).
Figure 4B:
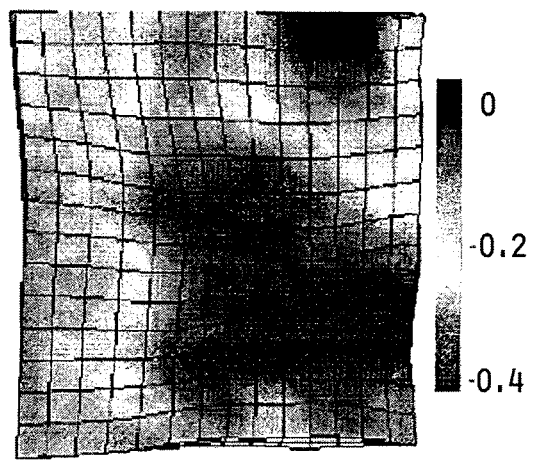
Figure 4C:
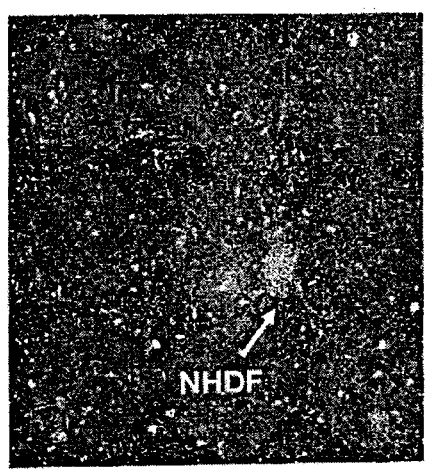
Figure 4D:
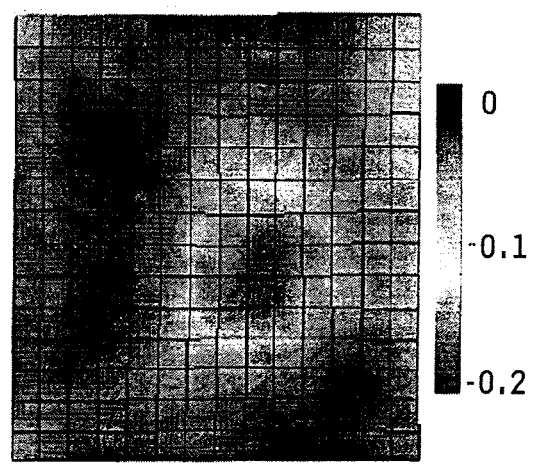

By 12 hours, the morphological differences that resulted from the various ECM microenvironments were subtler, largely owing to varying levels of ECM remodeling induced by cells at this time. At 12 hours, cells seeded within all ECM formulations appeared relatively spindle, bipolar-shaped. However, qualitative and morphometric analyses indicated that as the type III collagen content increased within the ECM, cells showed a statistically significant decrease in length ($p<0.05$), a subtle increase in width, and a decline in the length-to-width ratio as indicated (FIG. 3A-C). Based upon both qualitative and quantitative 3D morphology data, it appeared that cells grown in ECMs containing type III collagen took on a more contracted cell state. Despite the observed changes in cell shape, no significant differences were noted in 3D cell surface area (FIG. 3D) or cell volume at either time point. Consistent with previous studies (Pizzo et al., *J Appl Physiol* 98: 1909-1921, 2005), a larger proportion of cells grown within ECMs of higher total collagen content possessed an increased number of cytoplasmic projections at both 6- and 12-hour time points; however, this effect on projection number was less obvious when the collagen content was altered by adding type III collagen rather than type I collagen. Collectively these results demonstrate that cells adapt their shape, including the number and length of their projections, in response to ECMs that vary in collagen type I/III ratio. Furthermore, the morphological differences between cells appeared to be related to stiffness properties of the ECM.

EXAMPLE 27

Collagen Type I/III Ratio of 3D Microenvironment Affects Contractile State of the Cell and ECM Remodeling The collagen type I/III ratio also affected the ability of individual cells to deform and reorganize the component collagen fibrils of their surrounding ECM. Repeated monitoring of interactions between a cell and its surrounding collagen fibrils within a live tissue construct by confocal reflection microscopy provided a means of visualizing and quantifying this response over a 5 to 6 hour time window.

An IDVC algorithm (Roeder et al., *J Biomech Eng* 126: 699-708, 2004) was applied to consecutive confocal image stacks and used to determine 3D displacements and strains as they occurred locally to a given cell and adjacent collagen fibrils. Data generated from this algorithm provided the basis for 1) quantification of volumetric strain induced by a single cell within a tissue construct; 2) a detailed analysis of average local principal strains for each imaged volume; and 3) determination of magnitudes and locations for points within the image volume where maximum principal strains, $E_1$, $E_2$, and $E_3$, occurred. This data was then compiled and used to compare the mechanical status of a large number of individual cells grown within the different ECM formulations.

Figure 5:
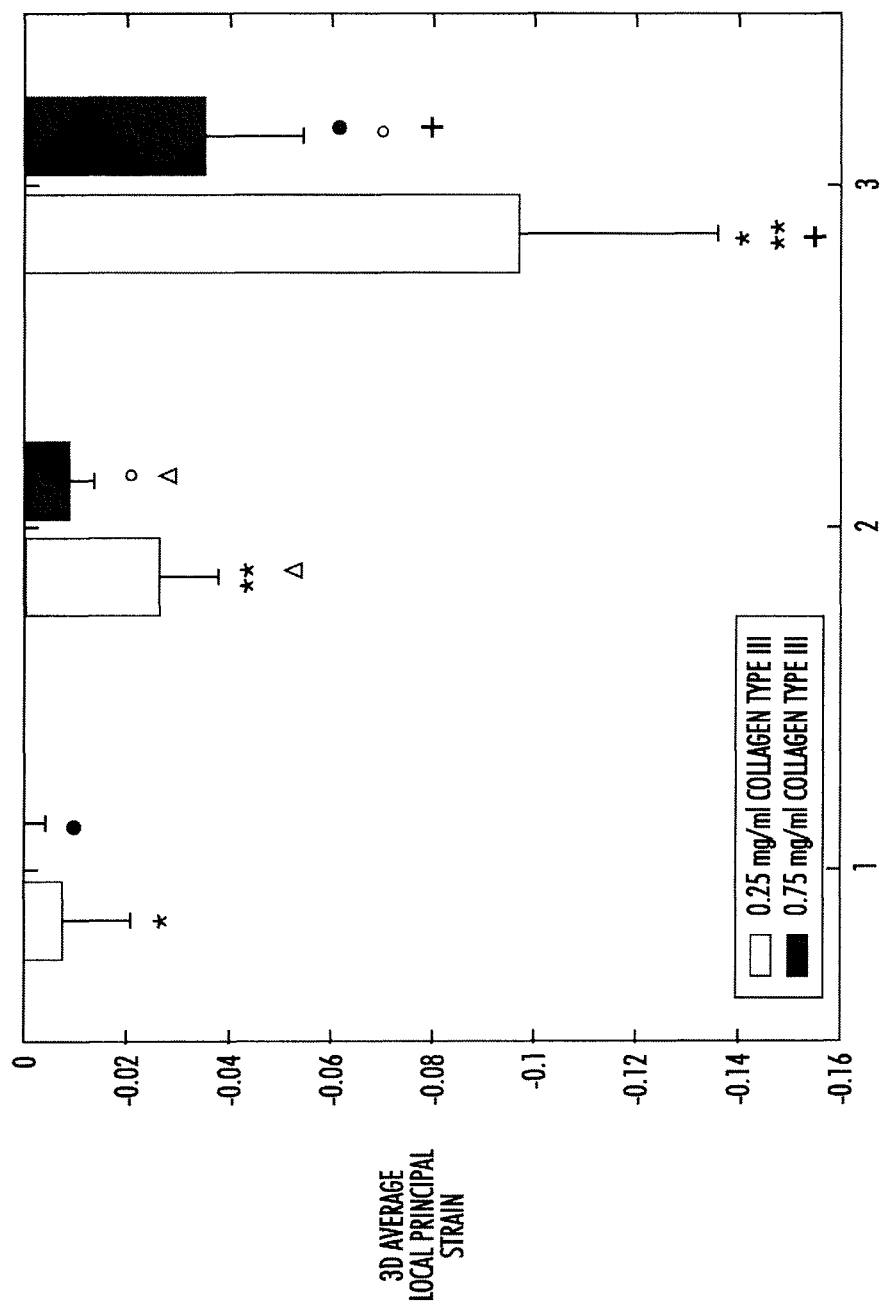
FIG. 5 represents a graph depicting contractility and matrix remodeling within engineered ECMs. NHDFs were grown within engineered ECMs in which the type I collagen concentration was kept constant at 1.5 mg/ml and the amount of type III collagen was either 0.25 mg/ml or 0.75 mg/ml. Average local 3D principal strains for a single cell and its surrounding ECM were quantified 5 hours post-polymerization ($5 \leq n \leq 6$). Negative strain values indicate compressive deformations. All relationships showing statistically significant differences ($p<0.05$) are indicated with symbols (*, **, ●, ○, +).
Figure 6:
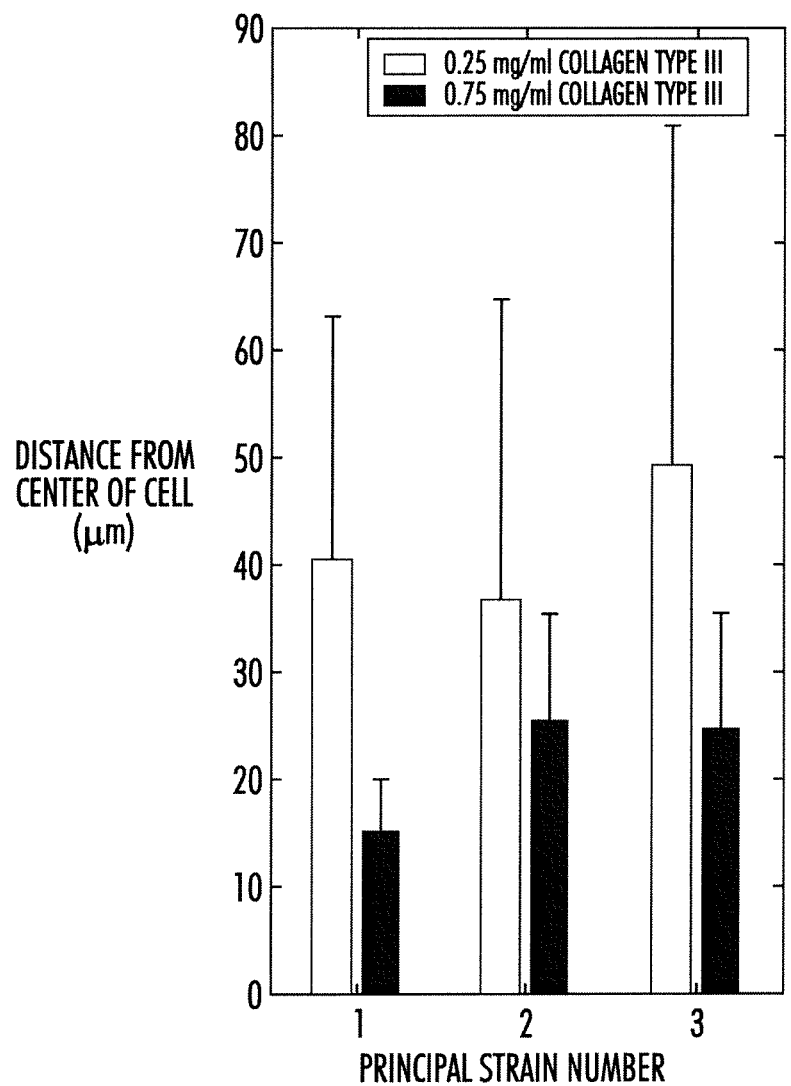
FIG. 6 represents a graph showing that points of maximum local deformation or strain induced within a 3D tissue construct, by low passage neonatal human dermal fibroblasts, occurred at distances further from the cell than for engineered ECMS prepared with lower amounts of type III collagen. NHDFs were grown within engineered ECMs in which the type I collagen concentration was kept constant at 1.5 mg/ml and the amount of type III collagen was either 0.25 mg/ml or 0.75 mg/ml.

Results showed that cells grown in ECMs containing type III collagen were less able to contract and remodel the surrounding matrix as the type III collagen content increased or type I/III ratio decreased. Qualitative perspectives and corresponding volumetric strain data obtained for representative cells grown within type I collagen ECMs prepared with low (0.25 mg/ml) and high (0.75 mg/ml) type III collagen concentrations are shown (FIG. 4). Comparison of average local principal strains induced by cells grown within the different ECM formulations indicated that cells grown at low type III collagen levels (0.25 mg/ml) induced higher strain (approximately 3 to 3.5 greater) in each of the three principal directions compared to those grown at high type III collagen levels (0.75 mg/ml) and these differences were significant for E2 and E3 ($p<0.05$; FIG. 4). However, it is important to note that type III collagen containing ECMs with total collagen contents of 1.75 mg/ml to 2.25 mg/ml were characterized by 3D average local principal strain levels that were about 2 to 3 times greater than ECMs prepared of type I collagen alone and a total collagen content of 1 mg/ml. Analysis of the locations and magnitudes for points of maximum principal strain in the 1-, 2-, and 3-direction revealed that cells grown within engineered ECMs of type III collagen content of 0.25 mg/ml induced strain values that were approximately twice that exerted by cells grown within ECMs containing 0.75 mg/ml type III collagen (FIG. 5). Furthermore, in general, points of maximum principal strain for all three directions occurred at distances further from the center of the cell (FIG. 6) when grown in ECMs at the low versus high type III collagen content. Specifically, maximum principal strains were observed at distances of 40-50 μm from the center of the cell for ECMs containing 0.25 mg/ml type III collagen. However, cells within ECMs prepared with a type III collagen content of 0.75 mg/ml generated maximum principal strains at distances of only 15-25 μm from the center of the cell. Although the addition of type III collagen enabled cells to induce large principal strains within their ECMs, the distance at which maximum principal strain occurred was considerably less than that found for ECMs prepared at low levels of type I collagen alone (FIG. 6). More specifically, ECMs prepared at 1 mg/ml type I collagen yielded, on average, points of maximum principal strain for 1-, 2-, and 3-directions at distances of 48 μm, 45 μm, and 52 μm from the center of the cell, respectively. It was also noted that the locations of the maximum principal strain were often associated with and occurred along major cell projections, especially for cells grown at the high collagen type I/III ratios. Furthermore, fibril deformation patterns were dependent upon the collagen type I/III ratio. Remodeling of ECMs containing type III collagen was characterized by fibril condensation around the cell periphery. On the other hand, ECMs prepared from type I collagen alone showed regional areas of fibril alignment. The difference in ECM remodeling, as indicated by both qualitative fibril deformation and quantified strains suggested differences in mechanical properties between fibrils formed from homotypic type I and heterotypic type I/III fibrils.

Based collectively on the observed effects of type III collagen on ECM microstructure/mechanical properties as well as differences in the 3D cell morphology and cell-induced ECM remodeling within these matrices, it was hypothesized that varying the collagen type I/III ratio within the ECM microenvironment modulated the contractile state of resident cells. To test this hypothesis, cells were seeded within the 3D ECM microenvironments and the organization of cytoskeletal actin was visualized using confocal microscopy 6 hours post polymerization. Results showed prominent actin stress fiber formation for cells within ECMs containing collagen III. Well-organized actin bundles (stress fibers) were even observed within ECMs containing the highest collagen III concentration, 0.75 mg/ml, despite the high total collagen content and fibril density. Cells containing a few scattered actin filaments were observed in ECMs prepared from type I collagen alone, but only at low collagen concentrations of 1.5 mg/ml and below. Cells with diffuse actin staining patterns were noted within ECMs prepared at collagen I levels greater than 1.5 mg/ml. Diffuse actin staining patterns were observed for cells grown in engineered ECMs representing type I collagen ECMs prepared at concentrations of 1 mg/ml and 3 mg/ml. A few organized actin bundles were noted in engineered ECMs created from 1 mg/ml type I collagen and a large number of organized actin bundles running parallel along the major cytoplasmic projections or long axis of cells grown within engineered type I collagen ECMs formed in the presence of 0.75 mg/ml type III collagen. Collectively, results showed that stress fiber formation, which is indicative of the contractile state of the cell, was positively related to cell-induced local ECM remodeling and strain and inversely related to ECM stiffness.

EXAMPLE 28

Figure 7A:
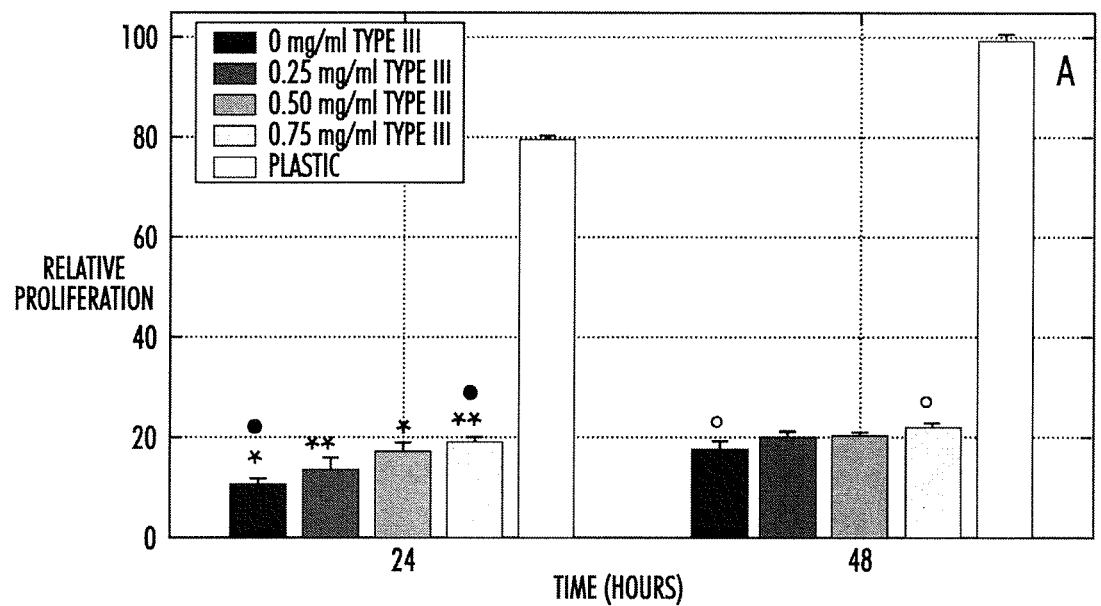
FIGS. 7A & 7B represent a series of graphs depicting data regarding the proliferation of low passage human dermal fibroblasts when grown within a 3D ECM format consisting of type I collagen ECMs prepared within increasing amounts of type III collagen (see FIG. 7A). NHDFs exposed to 2D ECM surface coatings representing the same biochemical compositions and collagen type I/III ratios showed no significant changes in proliferative response (see FIG. 7B). Selected relationships showing statistically significant differences ($p<0.05$) are indicated with symbols (*, **, ●, ○).

Collagen Type I/III Ratio within 3D Engineered ECMs but not 2D ECM Surface Coatings Modulates Cellular Proliferation To determine the effect of the collagen type I/III ratio on the fundamental proliferative behavior of cells, NHDFs were seeded within the different ECM formulations. For comparison purposes, parallel studies were conducted in which fibroblasts were seeded onto tissue culture plastic. The number of living cells present at 24 and 48 hours following cell seeding was quantified indirectly using the metabolic indicator dye alamarBlue and confirmed qualitatively. Consistent with previous studies (Pizzo et al., *J Appl Physiol* 98: 1909-1921, 2005), cells grown within a 3D ECM microenvironment proliferated at decreased rates compared to those grown in a 2D format on tissue culture plastic (FIG. 7A). Fibroblast proliferation was enhanced in ECMs with increased type III collagen content (FIG. 7A). Since the type I collagen content was kept constant, increasing the amount of type III collagen also increased the overall collagen content. Although the total number of cells within all ECM formulations increased between 24 and 48 hours, the total number of fibroblasts was greatest for ECMs prepared with the highest type III collagen concentration for both time points. When type III collagen was added at levels below 0.25 mg/ml, in the range of 0.02 mg/ml to 0.10 mg/ml, the proliferative capacity of the resident cells was lower than that obtained for 1.5 mg/ml type I collagen alone.

Figure 7B:
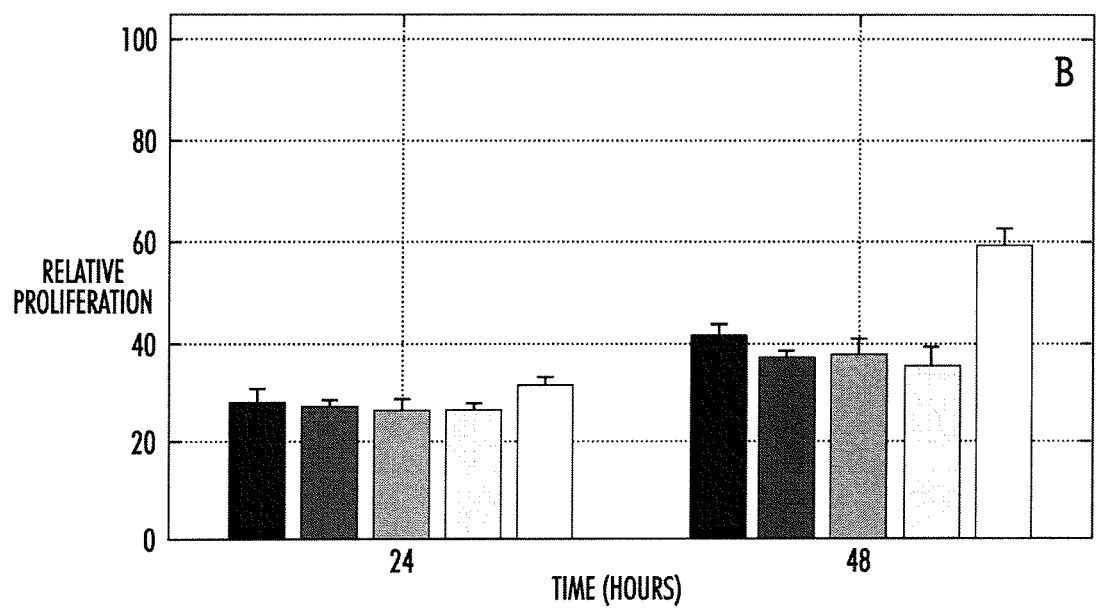

Since the addition of type III collagen affected not only microstructural-mechanical properties but also the macromolecular composition of the engineered ECMs, it was uncertain if changes in NHDF proliferation were a result of differences in biophysical or biochemical signals (cues) inherent in the 3D ECM microenvironments. To isolate the biochemical and biophysical variables, traditional experimental methods involving creation of 2D ECM surface coatings consisting of varied collagen I/III ratios to evaluate cell-ECM interactions were applied. NHDF were seeded onto the ECM-coated surfaces and proliferation monitored. No significant difference was observed in cell proliferation due to type III collagen content at either the 24- or 48-hour time points (FIG. 7B). All coatings showed a significant increase (p<0.05) in cell number between the 24- and 48-hour time points. And at the 48-hour time point, cells seeded on plastic showed significantly greater proliferation than those seeded on any of the ECM coated surfaces (p<0.05).

EXAMPLE 29

Comparison of Structure-Function of Engineered ECM Formulations

Various engineered ECM formulations were compared to analyze three-dimensional microstructure-mechanical properties, including fibril area fraction, fibril diameter, and stiffness of the engineered ECM (Table 11). The various engineered ECM formulations were also compared in regards to ECM contraction, morphology, and cell proliferation (Table 11).

TABLE 11

Comparison of Structure-Function of Engineered ECM Formulations

| | Engineered ECM Formulation | | | |
|---|---|---|---|---|
| | 1.0 mg/ml Type I | 1.5 mg/ml Type I | 3 mg/ml Type I | 1.5 mg/ml Type I + 0.75 mg/ml Type III |
| 3D ECM Microstructure-Mechanical Properties | | | | |
| Fibril Area Fraction (Density) | + | ++ | +++ | +++ |
| Fibril Diameter | ++ | ++ | ++ | + |
| Stiffness | + | ++ | +++ | + |
| Cellular Response: ECM Contraction/Morphology/Proliferation | | | | |
| ECM Contraction | +++ | ++ | + | ++/+++ |
| Distance | +++ | +++ | ++ | + |
| Number of projections | + | ++ | +++ | + |
| Length of projections | Medium-Long | Medium-Long | Medium-Long | Short |
| Morphology | Long-Spindle | Long-Spindle | Stellate | Short-Spindle |
| Cytoskeletal Actin | Stress-fibers | Stress-fibers | Diffuse | Stress-fibers |
| Proliferation | ++ | ++ | + | +++ |

EXAMPLE 30

Recent studies have demonstrated that human adipose-derived stem cells (ASC) derived from adult human adipose tissue secrete bioactive levels of multiple angiogenic and antiapoptotic growth factors including granulocyte-macrophage colony stimulating factor (GM-CSF), VEGF, hepatocyte growth factor (HGF), bFGF, and transforming growth factor-$\beta$ (TGF-$\beta$), and are able to enhance blood flow and minimize death of ischemic muscle tissue [Rehman et al., 2004, Circulation 109: 1292-8]. These results are important because they indicate that autologous delivery of ASC, which are readily available from liposuction under local anesthesia, may be a novel and uniquely feasible therapeutic option to enhance angiogenesis and tissue rescue in ischemia. However, quantitative analysis of cell delivery has documented that the majority of peripheral blood mononuclear cells or ASC injected via intramyocardial, intracoronary, and interstitial retrograde coronary venous (IRV) in an ischemic swine model are not retained in the heart immediately following delivery and that the processes of delivery were highly inconsistent. In addition, examination of ASC surviving 1 week following intramuscular injection showed reduction of cell numbers to 25% of the injected cells over this period, suggesting limited cell survival [Rehman et al., 2004, Circulation 109: 1292-8]; this is further corroborated in the myocardial system by survival of approximately 20% or less of initially retained mesenchymal stem cells over 4 weeks post-injection.

The survival, proliferation, and differentiation properties of human APC and EPC cells implanted within three dimensional matrices will be investigated using both standard cell culture media or by suspension in any of the formulations of "ready-to-assemble" components of self-assembling 3D matrix microenvironments, in which the microstructure, composition, and mechanical properties are quantified and systematically varied. The delivery efficiency and subsequent engraftment (cell survival and differentiation) of human ASC or endothelial progenitor cells derived from human cord blood (EPC) implanted within an animal model of hindlimb muscle ischemia will also be investigated. More particularly, cells will be delivered with or without injectable 3D matrix microenvironments in which the "instructive" or signaling properties are controlled and systematically varied.

Methods:

A series of in vitro experiments will be conducted to determine the effect of specific biophysical features of a cell's 3D ECM microenvironment on the fundamental behavior of human adipose-derived stem cells (ASC) and highly proliferative endothelial progenitor cells derived from human cord blood (EPC). ASC will be harvested from human adipose tissue as described previously [Rehman et al., 2004, Circulation 109: 1292-8]. Cultures of endothelial progenitor cells will be obtained from umbilical veins using established procedures [Ingram et al., 2004, Blood 104:2752-2760]. 3D ECM microenvironments in which specific biophysical features including fibril density, length, and width and stiffness are systematically varied will be created from purified collagen as described previously [Pizzo et al., 2005, J. App. Phys. 98:1909-1921; Roeder et al., 2002 J. Biomech Eng. 124: 214-22213,17]. In addition, 3D microenvironments in which composition is systematically varied by including ECM molecules such as type III collagen, hyaluronic acid, VEGF, bFGF will also be investigated. These molecules were chosen based upon their known role in neovascularization and cardiac muscle development. In all cases, cells will be added as the last component of the solubilized collagen matrix and the suspension will be injected over 30 seconds through a 25 Ga needle (paralleling intramuscular injection for in vivo systems) into a well plate and polymerized at 37° C. Immediately following polymerization (less than 30 minutes), complete medium will be added to all constructs.

For these studies, cell seeding densities ranging between $1\times10^5$ to $1\times10^7$ cells/ml will be evaluated. Fundamental cell behaviors including survival, morphology, proliferation, and differentiation will be determined using techniques established previously [Pizzo et al., 2005, J. App. Phys. 98:1909-1921]. In some cases, cells will be prelabeled with Cell-Tracker dyes or transfected with GFP and analyzed in 3- or 4-dimensions using confocal microscopy in a combination reflection-fluorescence mode. Outcomes will be compared to those from control "deliveries" in which cells are injected into media within culture plates, parallel to the situation for cell injection into a tissue environment in the absence of a solubilized, self-assembling matrix.

In addition to the in vitro culturing of cells within the 3D microenvironments, the 3D cell containing matrices will be implanted via injection into either normal or ischemic muscle in vivo, using the hindlimb model of muscle ischemia that the March lab has established and published in the preliminary findings concerning adipose stem cells [Rehman et al., 2004, Circulation 109: 1292-8]. Briefly, nude mice are employed so that cells of human origin can be studied in the absence of xenogeneic barriers. The ilio-femoral artery is surgically ligated and excised as described previously, in the left hindlimb only. The right hindlimb thus serves as a non-ischemic control. The musculature of the distal legs (e.g., tibialis anterior) then can be used as a well-demarcated delivery site for 100 µl injections into normal (right) and ischemic (left) muscle, that are performed under direct visualization. Injections of precisely defined numbers of ASC or EPC will be conducted 1 day following the surgical induction of ischemia in mice, with groups of 5 animals for each condition to be evaluated. The conditions will include control injections in saline (the previous standard) or in soluble self-assembling matrices. The cells will be labeled with GFP to permit enumeration by subsequent flow cytometry following muscle dissociation, as well as microscopic evaluation of the anatomy of engraftment and differentiation in selected mice. Mice injected will be sacrificed at either 3 hours post-injection, to quantify the number of cells retained acutely following delivery; and at 2 weeks post-injection, to determine precisely the cell survival over time following the injection. Cells will be counted by flow cytometry with the addition of fluorescent particles to permit precise volumetric enumeration. A total of 60 mice will be used in this study (e.g., 2 cell types×3 ECMs×5 animals/group×2 timepoints). The key endpoints will be quantitation of cell retention, and subsequent survival and engraftment into muscle or vasculature in the normal and ischemic muscles.

EXAMPLE 31

Effect of Hyaluronic Acid Content in 3D Matrices on Cell Behavior

Materials and Methods
Cell Culture.

Low passage neonatal human dermal fibroblasts (NHDFs), growth media, and passing solutions were obtained from Cambrex Bioproducts (Walkersville, Md.). NHDF were propagated in fibroblast basal medium supplemented with human recombinant fibroblast growth factor, insulin, gentamicin, amphotericin B, and FBS according to manufacturer's recommendation. Cells were maintained in a humidified atmosphere of 5% $CO_2$ at 37° C. and cell passage numbers representing 15 or less were used for all experiments.
Engineered 3D Tissue Constructs.

To investigate the effect of hyaluronic acid (HA) on ECM assembly and signaling, type I collagen matrices with varied HA concentrations were prepared. Native (acid solubilized) type I collagen prepared from calf skin (Sigma) and hyaluronic acid prepared from bovine vitreous humor (Sigma) were each dissolved in 0.01 N hydrochloric acid (HCl) to achieve desired concentrations. Dissolved collagen was sterilized by exposure to chloroform overnight at 4° C. Three-dimensional engineered ECMs were prepared similar to those described in Example 13 at a constant collagen type I concentration (2 mg/ml) and hyaluronic acid concentrations of between 0 and 1.0 mg/ml. The polymerization buffer consisted of 10× phosphate buffered saline (PBS) with an ionic strength of 0.14 M and a pH of 7.4. All 3D engineered ECMs and tissue constructs were polymerized in vitro within a humidified environment at 37° C. To determine the cellular signaling capacity of each 3D microenvironment, 3D tissue constructs were formed by first harvesting NHDFs in complete media and then adding the cells ($5 \times 10^4$ cells/ml) as the last component to the collagen solutions prior to polymerization. Immediately following polymerization complete media was added and the constructs were maintained in a humidified atmosphere of 5% $CO_2$ in air at 37° C.

Qualitative and Quantitative Analysis of 3D ECM Microstructure

Two quantitative parameters describing the 3D fibril microstructural composition of the ECM, fibril area fraction (a 2D approximation of 3D fibril density) and fibril diameter, were determined based upon confocal reflection and scanning electron microscopy (SEM) images. Prior to microstructural analysis, engineered 3D ECM constructs were polymerized within four-well Lab-Tek coverglass chambers (Nalge Nunc International, Rochester, N.Y.) and placed within a humidified environment at 37° C. where they were maintained for approximately 15 hours. For measurements of fibril area fraction, the confocal microscope was used to obtain high resolution, 3D, reflection images of the component collagen fibrils within each ECM. Three images (at least 10 µm in thickness) were taken at random locations within specimens representing a given 3D ECM composition. The confocal image stacks were then read into Matlab (The Mathworks, Natick, Mass.), and 2D projections of each image were created and a threshold chosen for binarization. Using a built-in function in Matlab, the area occupied by collagen fibrils (white pixels) was calculated, converted to µm2 based upon the pixel sizes, and normalized to the total image area.

Fibril diameter measurements were made by applying Imaris 4.0 (Bitplane Inc., Saint Paul, Minn.) to both confocal reflection and SEM images of engineered ECM constructs. For SEM imaging, engineered ECM constructs were fixed in 3% glutaraldehyde in 0.1M cacodylate at pH 7.4, dehydrated with ethanol, and critical point dried. Samples were sputter-coated with gold/palladium prior to imaging. Samples were imaged in at least duplicate with a JEOL (Peabody, Mass.) JSM-840 SEM. From each image obtained, twenty fibrils were chosen at random (5 fibrils per quadrant). Five lines were drawn perpendicular to the long axis of each fibril using the measurement tool in Imaris. The average number of pixels representing the fibril diameter was then converted into µm based upon the known pixel size.

Dynamic Mechanical Testing of 3D Engineered ECMs

Mechanical properties of the engineered ECMs were measured using a TA Instruments (New Castle, Del.) AR-2000 rheometer. Soluble ECM preparations were adjusted to specific polymerization conditions and placed on the peltier temperature-controlled lower plate at 22° C., and the 40-mm parallel-plate geometry was lowered to a 1-mm gap. The temperature was then raised to 37° C. to initiate polymerization. The peltier heated plate required about 1 minute to stabilize at 37° C. Measurements of storage modulus G' and loss modulus G" of the polymerizing material under controlled-strain oscillatory shear were made every 30 seconds under oscillation at 1 Hz and 0.1% strain for a proscribed time. This strain was sufficiently small to ensure that it did not affect the kinetics of polymerization. Two hours and thirty minutes after polymerization, a shear creep test was conducted with a shear stress of 1 Pa for 120 seconds. Creep data was interpreted with a standard four-element Voigt spring dashpot model. Next a frequency sweep of controlled-strain oscillatory shear was made at 0.1% strain, from 0.01 to 20 Hz. Following the frequency sweep, a continuous shear stress ramp from 0.1 to 10.0 Pa over 2 minutes was applied. Finally, the specimen was subjected to unconfined compression at a rate of 10 μm/sec.

Qualitative and Quantitative Determination of Cell Proliferation

Quantification of NHDF proliferation and its dependency on the 3D ECM microenvironment involved preparing 3D tissue constructs within 24-well tissue-culture plates. For comparison purposes, the proliferative capacity of NHDF was also determined for an equivalent number of cells seeded directly onto the surface of tissue culture plastic. At time-points representing 24 and 48 hours after construct polymerization and/or cell seeding, each well and tissue construct was examined microscopically to observe the viability, number, and morphology of the cells. The medium from each well then was replaced with fresh medium containing the metabolic indicator dye alamarBlue (10% v/v; BioSource International, Inc., Camarillo, Calif.). Approximately 18 hours later, dye reduction was monitored spectrofluorometrically using a FluoroCount Microplate Fluorometer (Packard Instruments, Meriden, Conn.) with excitation and emission wavelengths of 560 nm and 590 nm, respectively. Background fluorescence measurements were determined from wells containing only dye reagent in culture medium. Maximum levels of relative fluorescence were determined from alamarBlue solutions that were autoclaved to induce complete dye reduction. The mean and the standard deviation values for all fluorescence measurements were calculated and subsequently normalized with respect to the background and maximum fluorescence readings.

Time-Lapse Imaging of Cell-ECM Interactions

Tissue constructs representing NHDFs seeded at $5 \times 10^4$ cells/ml within 3D engineered ECMs with defined microstructural and biochemical compositions were evaluated using time-lapse confocal microscopy. Beginning 1 hour after polymerization, 2 to 3 cells were repeatedly monitored using the confocal microscope in a reflection (back-scattered light) mode to obtain image stacks of the individual cell and its surrounding matrix as described previously (Voytik-Harbin, et al., Microscopy and Microanalysis, 9:74-85, 2003). Images were collected at 30-minute intervals and a z-step of 0.5 mm to minimize exposure of the tissue constructs to radiation from the argon laser.

Determination of Volumetric Strain

Consecutive confocal reflection images representing temporal deformation induced by a resident cell on its surrounding ECM microstructure provided the basis for the quantification of local displacements and strains in 3D. Within each image, subvolumes of 32×32×20 pixels in the x, y, and z directions, respectively, were established. Each subvolume represented a group of voxels centered around a given point at which displacement values were sought. Each image subvolume provided a unique 3D voxel intensity pattern that allowed correlation pattern matching between consecutive images using an incremental digital volume correlation (IDVC) algorithm developed previously by our laboratory (Roeder et al., *J. Biomech. Eng.* vol. 124, pp. 214-222 (2002)). The IDVC algorithm provided strain-state data, including principal strains and their associated directions, for all grid point locations. Grid points were established in 512'512-pixel images that were 32 pixels apart in both x- and y-directions, with 24-pixel spacing in the z-direction. Principal strains determined for the length ($E_L$), width ($E_W$), and height ($E_H$) directions were used to calculate volumetric strain ($E_V$) based upon the following formula:

$$E_V = E_H + E_W + E_L + (E_W \cdot E_H) + (E_L \cdot E_H) + (E_L \cdot E_W) + (E_L \cdot E_W \cdot E_H).$$

Determination of 3D Cell Morphology

Prior to imaging at either 6 or 12 hours after construct polymerization, tissue constructs were stained with the vital dye Cell Tracker Green (Molecular Probes, Eugene, Oreg.) to facilitate discrimination of the cell from the surrounding collagen ECM. Confocal image stacks were then collected in a combined reflection-epifluorescence mode for determination of cell morphology and fibril microstructural organization.

Results

Fibril diameter distribution was measured, as determined from scanning electron microscopy images, for engineered matrices prepared from type I collagen in the presence of varied amounts of hyaluronic acid. Over the range of hyaluronic acid concentrations tested, no significant difference was observed in mean fibril diameter. Mean fibril diameter measurements were 80.8±18.3 72.2±13.0 and 72.1±11.8 μm (±standard deviation) for engineered matrices prepared from 2 mg/ml type I collagen containing 0, 0.5 mg/ml, and 1.0 mg/ml hyaluronic acid, respectively. Interestingly, it did appear that the variation (standard deviation) of fibril diameter measurement decreased with increasing hyaluronic acid content. No observable or quantitative differences in fibril area fraction measurements were determined for the engineered matrices prepared with and without hyaluronic acid.

While hyaluronic acid did not dramatically effect the fibril microstructure of engineered matrices, the polymerization rate was found to decrease with increasing hyaluronic acid content as indicated by a decreased slope of the G' versus time plot. Furthermore, as the hyaluronic acid content increased, the engineered matrices showed an increase in compliance and an increase in their compressive stiffness, respectively. These results demonstrate that the 3D fibril microstructure as well as the viscous fluid component provide critical determinants of the overall mechanical properties of the engineered ECMs.

Studies comparing the cell response to 3D ECM microenvironments prepared with various hyaluronic acid content have shown no significant difference in the proliferation properties of neonatal human dermal fibroblasts. However, analysis of cell morphology and matrix contraction (remodeling) by cells indicate that hyaluronic acid alters the mechanics of cell-ECM interactions. Analyses of the magnitude and spatial distribution of local, 3D strain induced by a resident cell within an engineered matrix microenvironment revealed that the addition of hyaluronic acid reduces the ability of fibroblasts to effectively contract and induce alignment of surrounding collagen fibrils. In other words, the extent of fibril deformation and realignment (remodeling) by cells is decreased and more uniformly distributed around the cell in the presence of increased concentrations of hyaluronic acid.

Results of these studies show that while the addition of hyaluronic acid does not dramatically affect the 3D fibril microstructure of the resultant engineered matrices, it does affect the mechanical properties, likely by changing the properties of the viscous fluid component. Furthermore, systematic variation of the viscous fluid component as a specific design criteria for 3D engineered matrices does affect the mechanisms by which resident cells mechanically manipulate (contract) or remodel their ECM microenvironment.

What is claimed is:

1. A tissue graft composition, said composition comprising
   a synthetic collagen-based matrix comprising collagen fibrils, wherein the matrix has an elastic or linear modulus of about 0.5 kPa to about 40 kPa; and
   a population of mesenchymal stem cells,
   wherein the matrix is prepared by a process comprising the step of controlling the elastic or linear modulus to make the stem cells adipogenic or osteogenic.

2. The composition of claim 1 wherein the step of controlling the elastic or linear modulus makes the stem cells adipogenic.

3. The composition of claim 1 wherein the step of controlling the elastic or linear modulus makes the stem cells osteogenic.

4. The composition of claim 2 wherein the matrix is a purified collagen matrix.

5. The composition of claim 3 wherein the matrix is a purified collagen matrix.

6. The composition of claim 2 wherein the collagen is enzymatically digested.

7. The composition of claim 6 wherein the collagen is protease digested.

8. The composition of claim 3 wherein the collagen is enzymatically digested.

9. The composition of claim 8 wherein the collagen is protease digested.

10. The composition of claim 2 wherein the collagen is not enzymatically digested.

11. The composition of claim 3 wherein the collagen is not enzymatically digested.

12. The composition of claim 2 wherein the collagen is solubilized collagen.

13. The composition of claim 3 wherein the collagen is solubilized collagen.

14. The composition of claim 2 wherein the fibril area fraction of the matrix is about 7% to about 26%.

15. The composition of claim 3 wherein the fibril area fraction of the matrix is about 7% to about 26%.

16. The composition of claim 2 wherein the matrix is sterile.

17. The composition of claim 3 wherein the matrix is sterile.

18. The composition of claim 2 wherein the composition further comprises a glycoprotein, a proteoglycan, or a glycosaminoglycan.

19. The composition of claim 3 wherein the composition further comprises a glycoprotein, a proteoglycan, or a glycosaminoglycan.

20. The composition of claim 2 wherein the composition further comprises a cell culture medium and wherein the cells are at a density of less than $5 \times 10^4$ cells per milliliter of the medium.

21. The composition of claim 3 wherein the composition further comprises a cell culture medium and wherein the cells are at a density of less than $5 \times 10^4$ cells per milliliter of the medium.

22. The composition of claim 2 wherein the composition further comprises a sterile package.

23. The composition of claim 3 wherein the composition further comprises a sterile package.

24. The composition of claim 1 wherein the matrix has an elastic or linear modulus of about 0.5 kPa to about 24 kPa.

25. The composition of claim 1 wherein the matrix has an elastic or linear modulus of about 25 kPa to about 40 kPa.

* * * * *